(12) United States Patent
Tasker et al.

(10) Patent No.: US 9,346,801 B2
(45) Date of Patent: May 24, 2016

(54) SUBSTITUTED 7-OXO-PYRIDO[2,3-D]PYRIMIDINES AND METHODS OF USE

(71) Applicant: AMGEN INC., Thousand Oaks, CA (US)

(72) Inventors: Andrew Tasker, Simi Valley, CA (US); Ryan Wurz, Newbury Park, CA (US); Liping H. Pettus, Thousand Oaks, CA (US); Bradley J. Herberich, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 163 days.

(21) Appl. No.: 14/190,400

(22) Filed: Feb. 26, 2014

(65) Prior Publication Data

US 2014/0249131 A1 Sep. 4, 2014

Related U.S. Application Data

(60) Provisional application No. 61/771,582, filed on Mar. 1, 2013.

(51) Int. Cl.
*C07D 487/02* (2006.01)
*C07D 471/04* (2006.01)

(52) U.S. Cl.
CPC .................. *C07D 471/04* (2013.01)

(58) Field of Classification Search
CPC .................................................. C07D 487/02
See application file for complete search history.

(56) References Cited

U.S. PATENT DOCUMENTS

| | | |
|---|---|---|
| 2005/0009849 A1 | 1/2005 | Veach et al. |
| 2011/0201594 A1 | 8/2011 | Murthi et al. |

FOREIGN PATENT DOCUMENTS

| | | |
|---|---|---|
| CN | 103012399 A | 4/2013 |
| WO | 2009/158571 A1 | 12/2009 |
| WO | 2010/129053 A2 | 11/2010 |
| WO | 2012061299 A1 | 5/2012 |
| WO | 2012158843 A2 | 11/2012 |
| WO | 2012167415 A1 | 12/2012 |
| WO | 2013/170671 A1 | 11/2013 |

OTHER PUBLICATIONS

Database WPI, Week 201381, Thomson Scientific, London, GB; AN 2013-N70141, XP002723179.
Database WPI, Week 201381, Thomson Scientific, London, GB; AN 2013-V12286, XP002723180.

*Primary Examiner* — Michael Barker
*Assistant Examiner* — Karen Cheng
(74) *Attorney, Agent, or Firm* — G. Prabhakar Reddy

(57) ABSTRACT

The invention encompasses compounds, analogs, prodrugs and pharmaceutically acceptable salts thereof, pharmaceutical compositions, uses and methods for prophylaxis and treatment of cancer.

21 Claims, No Drawings

SUBSTITUTED 7-OXO-PYRIDO[2,3-D]PYRIMIDINES AND METHODS OF USE

RELATED APPLICATIONS

This application claims the benefit of U.S. Provisional Patent Application No. 61/771,582, filed on Mar. 1, 2013, which is hereby incorporated herein by reference in its entirety.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins which play a central role in the regulation of a wide variety of cellular processes, maintaining control over cellular function. A partial list of such kinases includes abl, Atk, bcr-abl, Blk, Brk, Btk, c-kit, c-met, c-src, CDK1, CDK2, CDK3, CDK4, CDK5, CDK6, CDK7, CDK8, CDK9, CDK10, cRafl, CSF1R, CSK, EGFR, ErbB2, ErbB3, ErbB4, Erk, Fak, fcs, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

The ErbB receptor family belongs to the subclass I receptor tyrosine kinase superfamily and includes four distinct receptors including epidermal growth factor receptor (EGFR or ErbB 1). Erb132 (HER22 or p185neu). Erb133 (HER3), and Erb134 (HER4 or rvro2). Over 60% of all solid tumors overexpress at least one of these proteins or their ligands.

EGFR or ErbB1 has been implicated in human malignancy. Overexpression of EGFR is commonly found in breast, lung, head and neck, bladder tumors. Monoclonal antibodies directed against the EGFR, or its ligands TGF-alpha and EGF have been evaluated as therapeutic agents in the treatment of such malignancies. The reversible inhibitors Tarceva (erlotinib) and Iressa (gefitinib) currently are first-line therapy for non-small cell lung cancer patients with activating mutations. Activating mutations in the tyrosine kinase domain of EGFR have been identified in patients with non-small cell lung cancer (Lin, N. U.; Winer, E. P., Breast Cancer Res 6: 204-210, 2004). The most common activating mutations are L858R and delE746-A750. Another mutant, T790M, has been detected in at least half of such clinically resistant patients. Moreover, T790M may also be pre-existing, there may be an independent, oncogenic role for the T790M mutation. In addition, germline EGFR T790M mutations are linked with certain familial lung cancers.

Current drugs in development, including second generation covalent inhibitors, such as BIBW2992, HKI-272 and PF-0299804, are effective against the T790M resistance mutation but exhibit dose-limiting toxicities due to concurrent inhibition of WT EGFR. Accordingly, there remains a need to find mutant-selective EGFR kinase inhibitors useful as therapeutic agents.

The compounds of the current invention have not been described for the treatment of cancer.

SUMMARY OF THE INVENTION

The present invention comprises a new class of 7-oxo-pyrido[2,3-d]pyrimidines useful in the treatment of diseases, such as EGFR mutant-mediated diseases, for example cancer. Accordingly, the invention also comprises pharmaceutical compositions comprising the compounds, methods for the treatment of EGFR mutant-mediated diseases and other maladies, such as treatment of solid tumors, for example breast, lung, head and neck, bladder cancers, using the compounds and compositions of the invention, and intermediates and processes useful for the preparation of the compounds of the invention.

The compounds of the invention are represented by the following general structure:

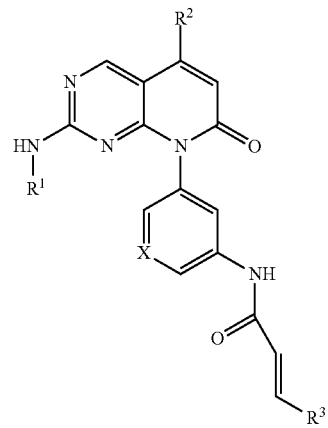

and a pharmaceutically acceptable salt thereof; wherein X; $R^1$; $R^2$; and $R^3$ are defined below.

The foregoing merely summarizes certain aspects of the invention and is not intended, nor should it be construed, as limiting the invention in any way. All patents, patent applications and other publications recited herein are hereby incorporated by reference in their entirety.

DESCRIPTION OF THE INVENTION

One aspect of the current invention relates to compounds having the general structure of formula 1:

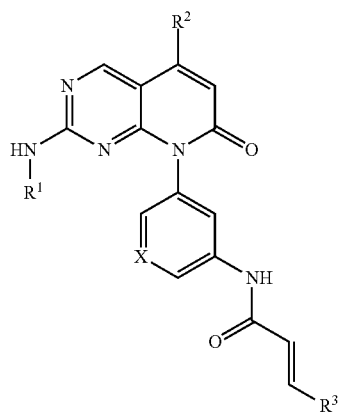

I wherein $R^1$ is

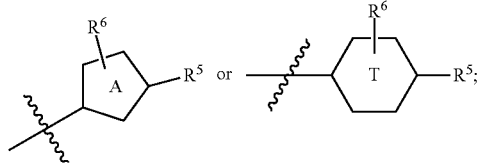

wherein Ring A is 5 membered heteroaryl;
wherein Ring T is phenyl or 6 membered heteroaryl;
wherein $R^2$ is H, F, Cl or methyl;
wherein $R^3$ is H, $C_1$-$C_6$ alkyl or $C_1$-$C_6$ dialkylamino-$C_1$-$C_6$ alkyl;
wherein $R^5$ is unsubstituted or substituted 5-6 membered saturated heterocyclyl or substituted 4-7 membered heterocyclylamino;
wherein $R^6$ is H, $C_1$-$C_6$ alkoxy, $C_1$-$C_6$ haloalkoxy or halo; and
wherein X is CH or N;
provided $R^5$ is not 4-morpholinyl;
and pharmaceutically acceptable salts thereof.

In another embodiment, the group X is CH.
In another embodiment, the group $R^3$ is H.
In another embodiment, the group $R^2$ is H or methyl.
In another embodiment, the group $R^2$ is methyl.
In another embodiment, the group $R^1$ is substituted phenyl.
In another embodiment, $R^1$ is substituted pyridyl or substituted pyrimidinyl.
In another embodiment, $R^5$ is optionally substituted piperazinyl, optionally substituted piperidinyl, optionally substituted pyrrolidinyl, optionally substituted diazepanyl, or optionally substituted azetidinylamino; wherein the piperazinyl, piperidinyl, pyrrolidinyl, diazepanyl, and azetidinyl rings are optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_1$ alkylcarbonyl, $C_{1-4}$ alkylsulfonyl, aminosulfonyl, $C_{1-4}$ hydroxyalkylcarbonyl, $C_{1-4}$ alkylaminocarbonyl, and $C_{1-4}$ haloalkylcarbonyl.

In another embodiment, the group $R^1$ is

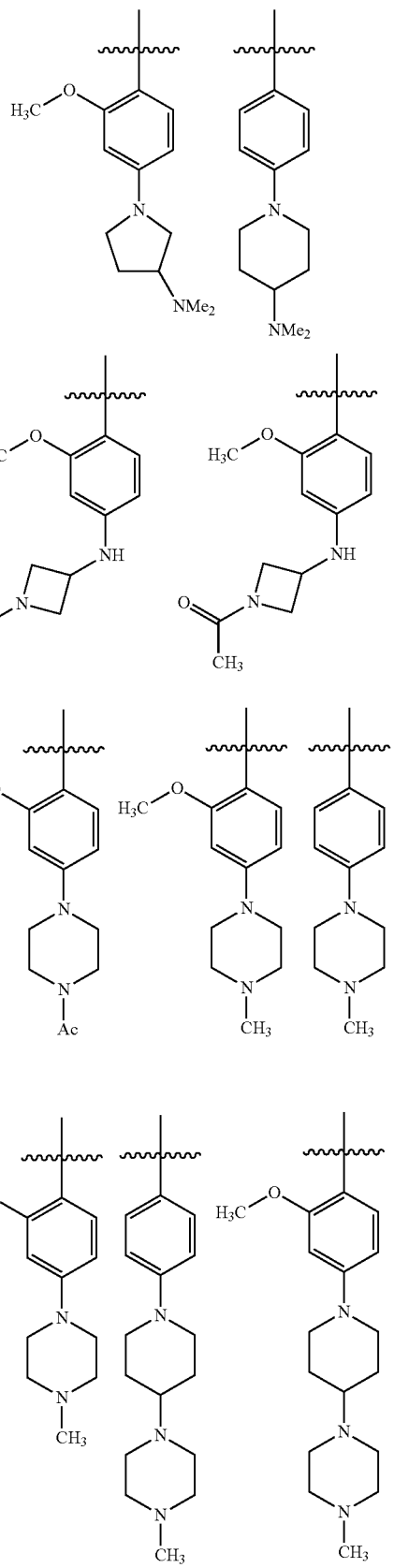

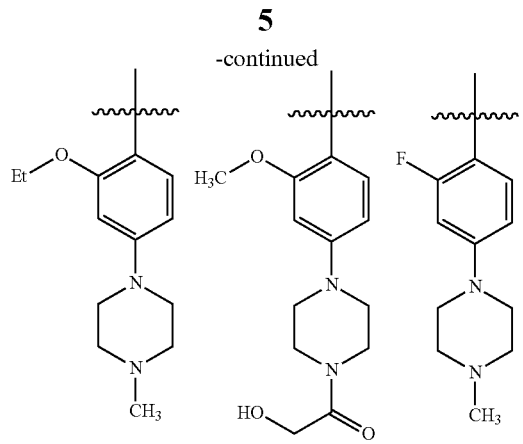
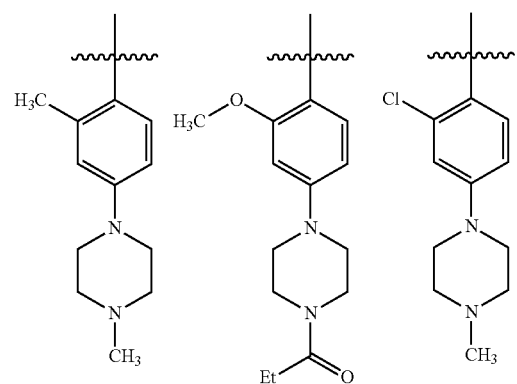
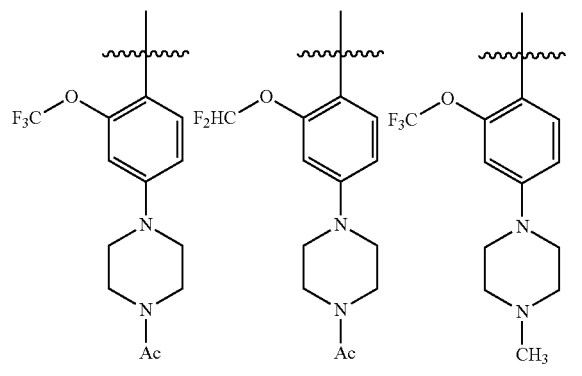
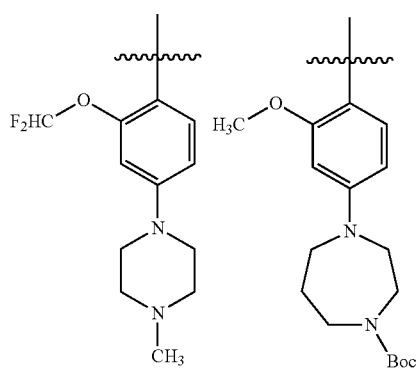
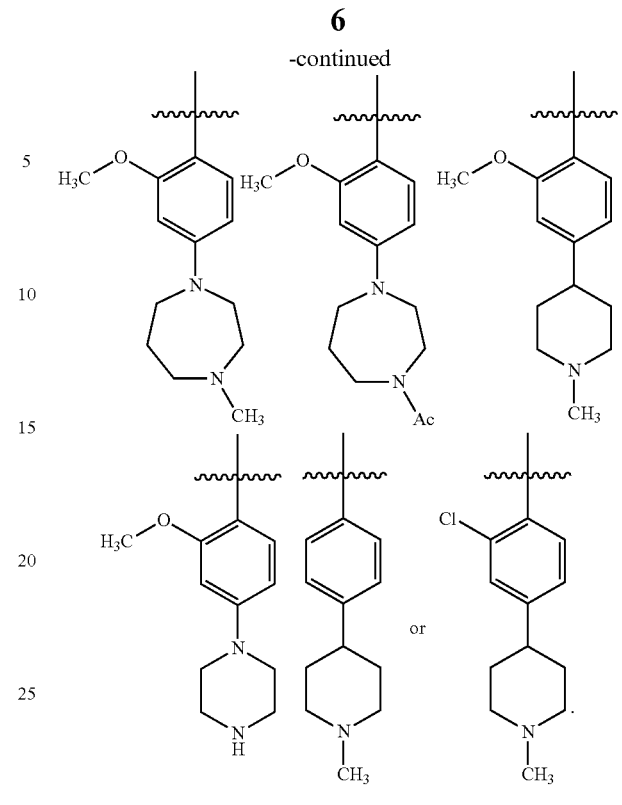

In another embodiment, $R^5$ is 1-fluoroethylazetidin-3-ylamino.

In another embodiment, $R^6$ is H, methoxy or chloro.

Another aspect of the current invention relates to compounds having the general structure of Formula II

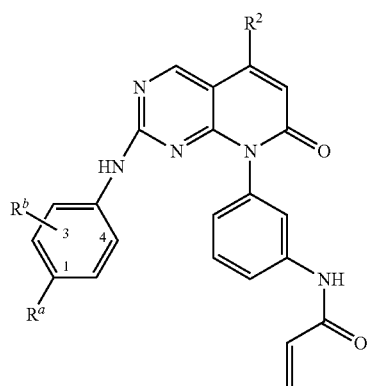

wherein $R^2$ is H or methyl;
wherein $R^a$ is optionally substituted piperazinyl, optionally substituted piperidinyl, optionally substituted pyrrolidinyl, optionally substituted diazepanyl, optionally or optionally substituted azetidinylamino; and
wherein $R^b$ is H or methoxy;
and pharmaceutically acceptable salts thereof.

In another embodiment, the group $R^2$ is methyl.

In another embodiment, the group $R^b$ is located at position 3 on the phenyl ring.

In another embodiment, the group IV is optionally substituted piperazinyl, optionally substituted piperidinyl, optionally substituted pyrrolidinyl, or optionally substituted diazepanyl; wherein the piperazinyl, piperidinyl, pyrrolidinyl and diazepanyl rings are optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_{1-4}$ alkylcarbonyl, $C_{1-4}$ alkylsulfonyl, aminosulfonyl, $C_{1-4}$ hydroxyalkylcarbonyl, $C_{1-4}$ alkylaminocarbonyl, and $C_{1-4}$ haloalkylcarbonyl.

In another embodiment, the group $R^a$ is azetidinylamino; wherein the azetindinyl is optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_{1-4}$ alkylcarbonyl, $C_{1-4}$ alkylsulfonyl, aminosulfonyl, hydroxyalkylcarbonyl, $C_{1-4}$ alkylaminocarbonyl, and $C_{1-4}$ haloalkylcarbonyl.

A family of specific compounds of particular interest within Formula 1 consists of compounds and pharmaceutically-acceptable derivatives thereof as follows:

N-(3-(2-((2-methoxy-4-(4-methyl-1-piperazinyl)phenyl)amino)-7-oxopyrido[2,3-d]pyrimidin-8(7H)-yl)phenyl)-2-propenamide;

(2E)-N-(3-(2-((2-methoxy-4-(4-methyl-1-piperazinyl)phenyl)amino)-7-oxopyrido[2,3-d]pyrimidin-8(7H)-yl)phenyl)-2-butenamide;

N-(3-(2-((4-(4-methyl-1-piperazinyl)phenyl)amino)-7-oxopyrido[2,3-d]pyrimidin-8(7H)-yl)phenyl)-2-propenamide;

N-(3-(2-((2-methoxy-4-(4-methyl-1-piperazinyl)phenyl)amino)-5-methyl-7-oxopyrido[2,3-d]pyrimidin-8(7H)-yl)phenyl)-2-propenamide;

N-(3-(6-ethyl-2-((2-methoxy-4-(4-methyl-1-piperazinyl)phenyl)amino)-7-oxopyrido[2,3-d]pyrimidin-8(7H)-yl)phenyl)-2-propenamide;

N-(3-(2-((4-methoxy-6-(4-methyl-1-piperazinyl)-3-pyridinyl)amino)-7-oxopyrido[2,3-d]pyrimidin-8(7H)-yl)phenyl)-2-propenamide;

(2E)-4-(dimethylamino)-N-(3-(24(2-methoxy-4-(4-methyl-1-piperazinyl)phenyl)amino)-7-oxopyrido[2,3-d]pyrimidin-8(7H)-yl)phenyl)-2-butenamide;

N-(4-fluoro-3-(2-((2-methoxy-4-(4-methyl-1-piperazinyl)phenyl)amino)-7-oxopyrido[2,3-d]pyrimidin-8(7H)-yl)phenyl)-2-propenamide;

N-(3-(2-((4-((1-(2-fluoroethyl)-3-azetidinyl)amino)-2-methoxyphenyl)amino)-7-oxopyrido[2,3-d]pyrimidin-8(7H)-yl)phenyl)-2-propenamide;

2-chloro-N-(3-(2-((2-methoxy-4-(4-methyl-1-piperazinyl)phenyl)amino)-7-oxopyrido[2,3-d]pyrimidin-8(7H)-yl)phenyl)acetamide;

3-(dimethylamino)-N-(3-(2-((2-methoxy-4-(4-methylpiperazin-1-yl)phenyl)amino)-7-oxopyrido[2,3-d]pyrimidin-8(7H)-yl)phenyl)propanamide;

N-(3-(2-((4-((1-acetylazetidin-3-yl)amino)-2-methoxyphenyl)amino)-7-oxopyrido[2,3-d]pyrimidin-8(7H)-yl)phenyl)acrylamide;

N-(3-(2-((2-chloro-4-(4-methyl-1-piperazinyl)phenyl)amino)-7-oxopyrido[2,3-d]pyrimidin-8(7H)-yl)phenyl)-2-propenamide;

N-(3-(2-((4-((1-(2-fluoroethyl)-3-azetidinyl)amino)-2-methoxyphenyl)amino)-5-methyl-7-oxopyrido[2,3-d]pyrimidin-8(7H)-yl)phenyl)-2-propenamide;

N-(3-(5-methyl-2-((4-(4-methylpiperazin-1-yl)phenyl)amino)-7-oxopyrido[2,3-d]pyrimidin-8(7H)-yl)phenyl)acrylamide;

N-(3-(2-((2-methoxy-4-(piperazin-1-yl)phenyl)amino)-5-methyl-7-oxopyrido[2,3-d]pyrimidin-8(7H)-yl)phenyl)acrylamide N-(3-(2-((2-methoxy-4-(1-methylpiperidin-4-yl)phenyl)amino)-5-methyl-7-oxopyrido[2,3-d]pyrimidin-8(7H)-yl)phenyl)acrylamide; and N-(3-(2-((4-(4-acetylpiperazin-1-yl)-2-methoxyphenyl)amino)-5-methyl-7-oxopyrido[2,3-d]pyrimidin-8(7H)-yl)phenyl)acrylamide.

As described in detail herein, infra, provided compounds are selective inhibitors of at least one mutation of EGFR. It has been surprisingly found that provided compounds are selective inhibitors of at least one mutation of EGFR as compared to wild-type ("WT") EGFR. In certain embodiments, the mutation of EGFR is T790M. In certain embodiments, the mutation of EGFR is a deletion mutation. In some embodiments, the mutation of EGFR is an activating mutation. In certain embodiments, a compound of the invention selectively inhibits at least one resistant mutation and at least one activating mutation as compared to WT EGFR. In some embodiments, a compound of the invention selectively inhibits at least one deletion mutation and/or at least one point mutation, and is sparing as to WT EGFR inhibition.

A mutation of EGFR can be selected from T790M (resistant or oncogenic), L858R (activating), delE746-A750 (activating), G719S (activating), or a combination thereof.

As used herein, the term "selectively inhibits," as used in comparison to inhibition of WT EGFR, means that a provided compound inhibits at least one mutation of EGFR (i.e., at least one deletion mutation, at least one activating mutation, at least one resistant mutation, or a combination of at least one deletion mutation and at least one point mutation) in at least one assay described herein (e.g., biochemical or cellular). In some embodiments, the term "selectively inhibits," as used in comparison to WT EGFR inhibition means that a provided compound is at least 50 times more potent, at least 45 times, at least 40, at least 35, at least 30, at least 25, or at least 20 times more potent as an inhibitor of at least one mutation of EGFR, as defined and described herein, as compared to WT EGFR.

As used herein, the term "sparing as to WT EGFR" means that a selective inhibitor of at least one mutation of EGFR, as defined and described above and herein, inhibits EGFR at the upper limit of detection of at least one assay as described herein (e.g., biochemical or cellular as described in detail in Examples 56-58). In some embodiments, the term "sparing as to WT EGFR" means that a provided compound inhibits WT EGFR with an IC50 of at least 10 μM, at least 9 μM, at least 8 μM, at least 7 μM, at least 6 μM, at least 5 μM, at least 3 μM, at least 2 μM or at least 1 μM.

In certain embodiments, a provided compound selectively inhibits (a) at least one activating mutation; and (b) T790M; and (c) is sparing as to WT. In some embodiments, the activating mutation is a deletion mutation. In some embodiments, and the activating mutation is a point mutation. In some embodiments, an activating mutation is delE746-A750. In some embodiments, an activating mutation is L858R. In some embodiments, an activating mutation is G719S.

In some embodiments, the at least one mutation of EGFR is L858R and/or T790M.

Without wishing to be bound by any particular theory, it is believed that administration of a provided compound to a patient having at least one activating mutation may preempt formation of the T790M resistance mutation. Thus, in certain embodiments, the present invention provides a method for inhibiting an activating mutation in a patient comprising administering to the patient a provided compound or composition thereof, as described herein.

One of ordinary skill in the art will appreciate that certain patients have an oncogenic form of the T790M mutation, i.e., the T790M mutation is present prior to administration to the patient any EGFR inhibitor and is therefore oncogenic. Accordingly, in some embodiments, the present invention provides a method for inhibiting oncogenic T790M in a patient comprising administering to the patient a provided compound or composition thereof, as described herein.

Indications

Compounds of the present invention would be useful for, but not limited to, the prevention or treatment of EGFR mutant-mediated diseases. The compounds of the invention have kinase inhibitory activity, such as T790M inhibitory activity.

Compounds of the invention are useful for the treatment of neoplasia including cancer and metastasis, including, but not limited to: carcinoma such as cancer of solid tumors, for example breast, lung, head and neck, bladder cancers.

Besides being useful for human treatment, these compounds are also useful for veterinary treatment of companion animals, exotic animals and farm animals, including mammals, rodents, and the like. More preferred animals include horses, dogs, and cats.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^{2}H$ and $^{3}H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

As used herein, the compounds of the present invention include the pharmaceutically acceptable derivatives thereof.

DEFINITIONS

The term "treatment" includes therapeutic treatment as well as prophylactic treatment (either preventing the onset of disorders altogether or delaying the onset of a preclinically evident stage of disorders in individuals).

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by being therapeutically effective in vivo.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

"Heterocycle" means a ring comprising at least one carbon atom and at least one other atom selected from N, O and S. Examples of heterocycles that may be found in the claims include, but are not limited to, the following:

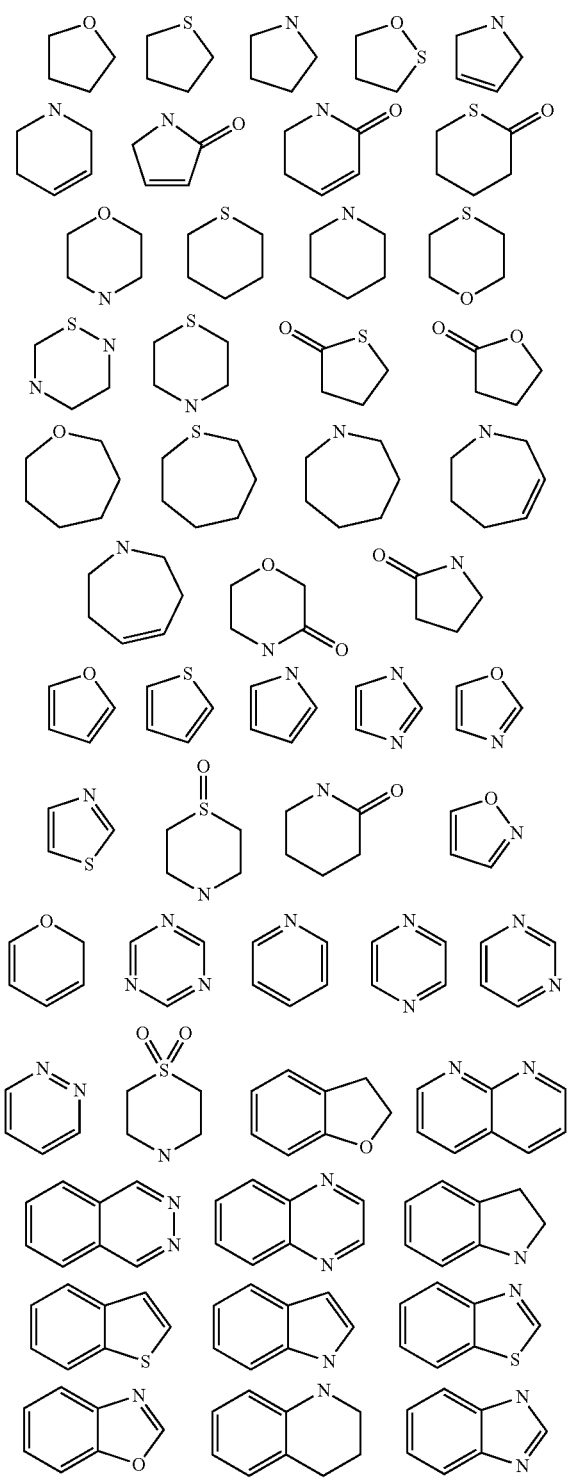

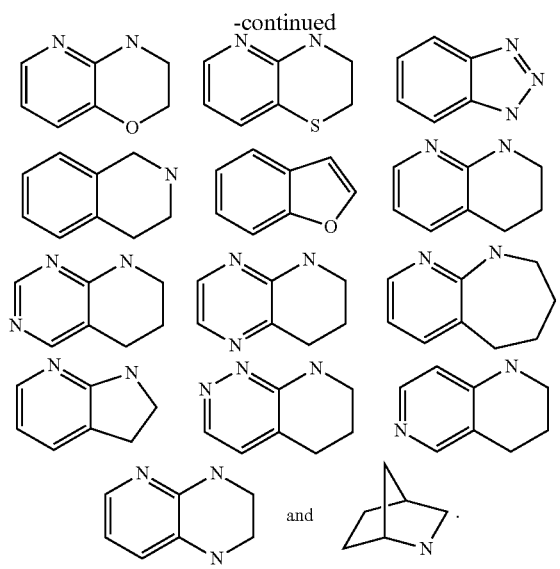

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "heterocyclylamino" embraces amino groups substituted with a heterocyclyl radical.

The term "alkylcarbonyl" denotes a carbonyl radical substituted with an alkyl group. Even more preferred are alkylcarbonyl radicals having alkyl lengths of one to four carbon atoms.

The term "alkoxycarbonyl" denotes an ester group, containing an alkoxy substituted carbonyl. Even more preferred are alkoxycarbonyl radicals having alkoxy lengths of one to four carbon atoms.

The term "haloalkylcarbonyl" denotes a carbonyl radical substituted with a haloalkyl group. Even more preferred are haloalkylcarbonyl radicals having haloalkyl lengths of one to four carbon atoms.

The term "hydroxyalkylcarbonyl" denotes a carbonyl radical substituted with an hydroxyalkyl group. Even more preferred are hydroxyalkylcarbonyl radicals having hydroxyalkyl lengths of one to four carbon atoms.

The term "alkylaminocarbonyl" denotes a carbonyl radical substituted with an alkylamino group. Even more preferred are alkylaminocarbonyl radicals having alkyl lengths of one to four carbon atoms.

The term "alkylsulfonyl" denotes a sulfonyl radical substituted with an alkyl group. Even more preferred are alkylsulfonyl radicals having alkyl lengths of one to four carbon atoms.

The term "aminosulfonyl" denotes a sulfonyl radical substituted with an amino group. This substituent is alternatively named sulfonamidyl or sulfamyl.

The term "oxo" represents the groups =O (as in carbonyl).

The term "comprising" is meant to be open ended, including the indicated component but not excluding other elements.

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tort-butyl, 4-methoxyphenylmethyl and the like, can be removed under hydrolysis and hydrogenolysis conditions well known to those skilled in the art.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of EGFR mutants.

The present invention comprises a pharmaceutical composition comprising a therapeutically-effective amount of a compound of Formulas I-II in association with a least one pharmaceutically-acceptable carrier, adjuvant or diluent.

The present invention also comprises a method of treating EGFR mutant related disorders, such as cancer in a subject, the method comprising treating the subject having or susceptible to such disorder with a therapeutically-effective amount of a compound of Formulas I-II. This includes first line therapies and second line therapies.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of Formula I may be administered either prior to, at the same time as, or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-21 I 4R, ITI E09, elmustine, Erbamont FCE-24517, estramustine phosphate sodium, fotemustine, Unimed G-6-M, Chinoin GYKI-17230, hepsul-fam, Ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, ellipticine acetate, Tsumura EPMTC, the epothilones, ergotamine, etoposide, etretinate, fenretinide, Fujisawa FR-57704, gallium nitrate, genkwadaphnin, Chugai GLA-43, Glaxo (3R-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemeitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors, TNF inhibitors, metallomatrix proteases inhibitors (MMP) and VEGFR inhibitors.

When the compositions of this invention comprise a combination of a kinase inhibitor of the Formulas described herein and one or more additional therapeutic or prophylactic agents, both the kinase inhibitor and the additional agent should be present at dosage levels of between about 10 to 100%, and more preferably between about 10 to 80% of the dosage normally administered in a monotherapy regimen. Such additional kinase inhibitory agents were those which may modulate, regulate or otherwise affect kinase enzyme activity. Such effects may lead to modulation of disease pathology and/or symptoms. Kinase inhibitory agents include, for example, small molecules, polypeptides, antibodies (including for example, monoclonals, chimeric, humanized, single chain, immunokines, etc.), and the like. Examples of additional kinase inhibitory small molecule agents include, but were not limited to, CDK inhibitors and p38 inhibitors, including SU-6668, SU-5416, ZD-4190, ZD-1839, STI-571, CP-358774, LY-333531 and the like.

The pharmaceutical compositions of this invention comprise an additional immunosuppression agent. Examples of additional immunosuppression agents include, but were not limited to, cyclosporin A, FK506, rapamycin, leflunomide, deoxyspergualin, prednisone, azathioprine, mycophenolate mofetil, OKT3, ATACj, interferon and mizoribine.

The pharmaceutical compositions of this invention may additionally comprise antibodies (including for example, monoclonals, chimeric, humanized, single chain, immunokines, etc.), cytotoxic or hormonal anti-cancer agents or combinations thereof.

The present invention comprises a process for the preparation of a compound of Formulas I-II.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Also included in the family of compounds of Formulas I-II are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane propionic, pantothenic, toluenesulfonic, salicylic, sulfanilic, stearic, succinic, tartaric, thiocyanic, and undecanoic.

Suitable pharmaceutically-acceptable base addition salts of compounds of Formulas I-II include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I-II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained. Additional examples of such salts can be found in Berge et al., J. Pharm. Sci., 66, 1 (1977).

The invention also relates to a method of making a compound of the formulas described herein, comprising synthesizing any one or more intermediates illustrated in the synthetic schemes herein and then converting that intermediate(s) to a compound of the formulas described herein. The invention also relates to a method of making a compound of the formulas described herein, comprising synthesizing any one or more intermediates illustrated in the examples herein and then converting that intermediate(s) to a compound of the formulas described herein.

GENERAL SYNTHETIC PROCEDURES

The compounds of the invention can be synthesized according to the following procedures of Scheme 1, wherein the substituents are as defined for Formulas I-II, above, except where further noted.

The following abbreviations are used:
RT—room temperature
MCPBA 3-chloroperoxybenzoic acid
DCM, $CH_2Cl_2$ dichloromethane
DIEA, $EtNiPr_2$—diisopropylethylamine, Hunig's base
DMF—dimethylformamide
DMSO dimethylsulfoxide
$K_2CO_3$—potassium carbonate
AcCN—acetonitrile
TFA—trifluoroacetic acid
HOAc, AcOH—acetic acid
$LiAlH_4$ lithium aluminum hydride
THF tetrahydrofuran
$CHCl_3$ Chloroform
$CDCl_3$ Deuterated chloroform
EtOAc ethyl acetate
$Na_2SO_4$—sodium sulfate
LiHMDS Lithium bis(trimethylsilyl)amide
mg—milligram
g—gram
ml—milliliter
h—hour
min—minutes
$Et_2O$—ethyl ether
$MgSO_4$—magnesium sulfate
$NH_4Cl$ ammonium chloride
$H_2O$—water
$NaHCO_3$—sodium bicarbonate
MeOH methanol
Boc—tert-butyloxycarbonyl
NaOH—sodium hydroxide
NaH—sodium hydride
CuI copper iodide
$NH_3$ ammonia
EtOH—ethanol
$Et_3N$—triethylamine
Pd/C—palladium on carbon
NMP N-methylpyrrolidinyl

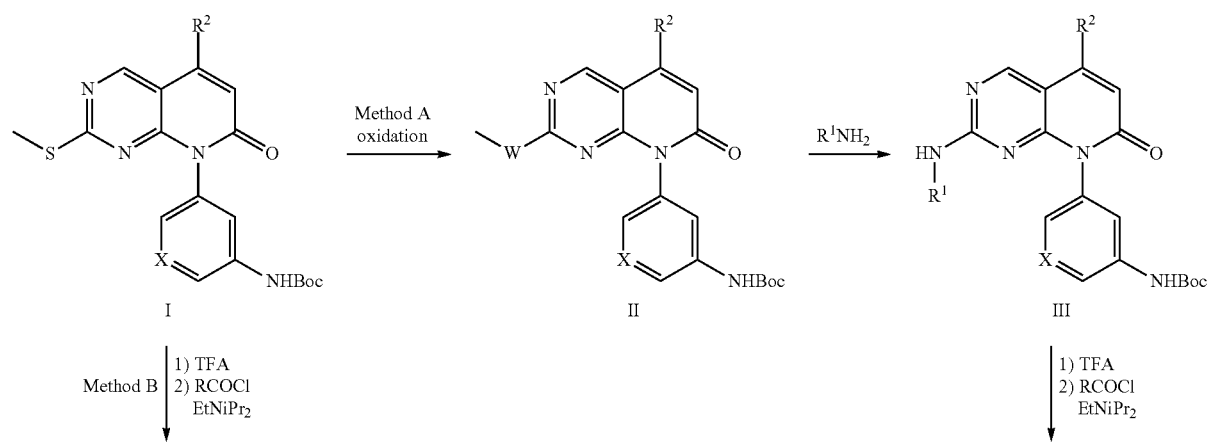

Scheme 1

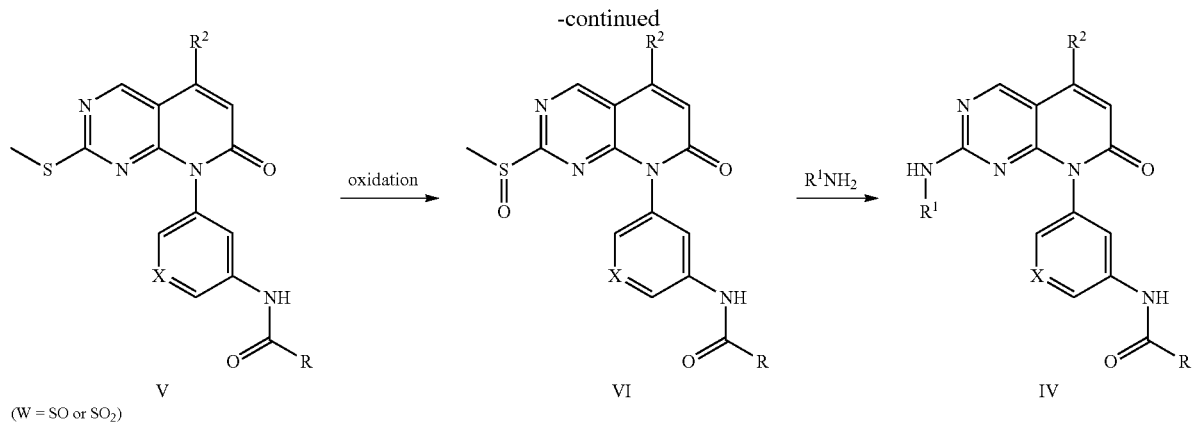

(W = SO or SO₂)

Acrylamide substituted 7-oxo-pyrido[2,3-d]pyrimidines can be prepared according to the methods set out in Scheme 1. 2-(Methylthio)-7-oxopyrido[2,3-c]pyrimidines (I) is treated with an oxidizing agent such as MCPBA, in an appropriate solvent such as in DCM, to furnish 2-(methylsulfonyl)-7-oxopyrido[2,3-d]pyrimidines (II). The 2-(methylsulfonyl)-7-oxopyrido[2,3-d]pyrimidines (II) is treated with a base, such as with DIEA, and heated at a temperature above RT, preferably above about 50° C., more preferably at about 80° C. to yield the amino substituted 7-oxopyrido[2,3-d]pyrimidines (III). Deprotection, such as with treatment with acid, followed by treatment with an unsaturated acid chloride, such as acryloyl chloride yields the desired product (IV).

Alternatively, the acrylamide (V) is formed from the starting material (I) by a method similar to that described above. The 2-(methylthio)-7-oxopyrido[2,3-d]pyrimidinyl acrylaminedes (V) can be oxidized, by a method similar to that described above followed by amination to yield the desired product (IV).

Scheme 2

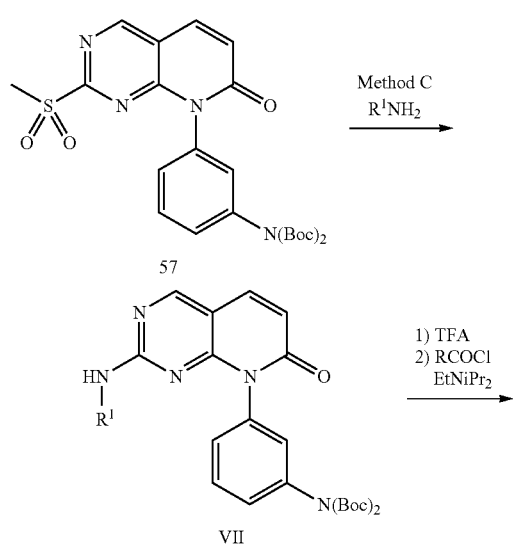

-continued

[structure IV]

Acrylamide substituted 7-oxo-pyrido[2,3-d]pyrimidines can be prepared from the di-Boc protected compound, according to the method set out in Scheme 2. The 2-(methylsulfonyl)-7-oxopyrido[2,3-d]pyrimidines (57) is treated with a base, such as with DIEA, and heated at a temperature above RT, preferably above about 50° C., more preferably at about 80° C. to yield the amino substituted 7-oxopyrido[2,3-d]pyrimidines (VII). Deprotection, such as with treatment with acid, followed by treatment with an unsaturated acid chloride, such as acryloyl chloride yields the desired product (IV).

The starting compounds defined in Schemes 1-2 may also be present with functional groups in protected form if necessary and/or in the form of salts, provided a salt-forming group is present and the reaction in salt form is possible. If so desired, one compound of formula I can be converted into another compound of formula I or a N-oxide thereof; a compound of formula I can be converted into a salt; a salt of a compound of formula I can be converted into the free compound or another salt; and/or a mixture of isomeric compounds of formula I can be separated into the individual isomers.

N-Oxides can be obtained in a known manner by reacting a compound of formula I with hydrogen peroxide or a peracid, e.g. 3-chloroperoxy-benzoic acid, in an inert solvent, e.g. $CH_2Cl_2$, at a temperature between about −10 to about 35° C., such as about 0° C. to about RT.

If one or more other functional groups, for example carboxy, hydroxy, amino, or mercapto, are or need to be protected in a compound of Formulas I-II, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically $K_2CO_3$ or NaOH.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80° C. to about 60° C., at RT, at about −20° C. to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

The solvents from which those can be selected which are suitable for the reaction in question include for example water, esters, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, IpOH or 1-propanol, nitriles, typically AcCN, halogenated hydrocarbons, typically $CH_2Cl_2$, amides, e.g. DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

A compound of any of the formulas delineated herein may be synthesized according to any of the processes delineated herein. In the processes delineated herein, the steps may be performed in an alternate order and May be preceded, or followed, by additional protection/deprotection steps as necessary. The processes may further comprise use of appropriate reaction conditions including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

The following examples contain detailed descriptions of the methods of preparation of compounds of Formulas I-II. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom (see below), whereby they are intended to be attached at any available atom that is not already substituted by an atom other than H.

Such heterocyclic ring systems may be attached through a carbon atom or a heteroatom in the ring system. In instances wherein a heterocyclic or heteroaryl ring system is stated to be attached at a heteroatom (e.g., nitrogen atom), this refers to the heterocyclic or heteroaryl ring system being attached to the designated functional group at said nitrogen heteroatom. Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

Analytical Methods:

Unless otherwise indicated all HPLC analyses were run on a HP-1050 system with an HP Zorbax SB—$C_{18}$ (5μ) reverse phase column (4.6×150 mm) run at 30° C. with a flow rate of 1.00 mL/min. The mobile phase used solvent A ($H_2O$/0.1% TFA) and solvent B (AcCN/0.1% TFA) with a 20 min gradient from 10% to 90% AcCN. The gradient was followed by a 2 min return to 10% AcCN and a 3 min flush.

LC-MS Method For:

Method A:
1. Samples were run on a HP-1100 MSD system with a HP Zorbax SB—$C_8$ (5μ) reverse phase column (4.6×50 mm) run at 30° C. with a flow rate of 0.75 ml/min.
2. The mobile phase used solvent A ($H_2O$/0.1% HOAc) and solvent B (AcCN/0.1% HOAc) with a 10 min gradient from 10% to 90% AcCN. The gradient was followed by a 1 min return to 10% AcCN and a 2 min flush.

Method B:
1. Samples were run on an HP-1100 system with an HP Zorbax SB—$C_8$ (5μ) reverse phase column (4.6×50 mm) run at 30° C. with a flow rate of 1.5 ml/min.
2. The mobile phase used solvent A ($H_2O$/0.1% HOAc) and solvent B (AcCN/0.1% HOAc) with a 5 min gradient from 10% to 90% AcCN. The gradient was followed by a 0.5 min return to 10% AcCN and a 1.5 min flush.

Preparative HPLC:

Where indicated, compounds of interest were purified via preparative HPLC using a Gilson workstation with a 20×50 mm column at 20 ml/min. The mobile phase used solvent A ($H_2O$/0.1% TFA) and solvent B (AcCN/0.1% TFA) with a 10 min gradient from 10% to 95% AcCN. The gradient was followed by a 2 min return to 20% AcCN.

Proton NMR Spectra:

Unless otherwise indicated, all $^1$H NMR spectra were run on a Bruker Advance 400 MHz instrument. All observed protons were reported as parts-per-million (ppm) downfield from tetramethylsilane (TMS) or other internal reference in the appropriate solvent indicated.

Intermediates

Preparation of tert-butyl (3-((5-formyl-2-(methylthio)pyrimidin-4-yl)amino)phenyl)carbamate (50)

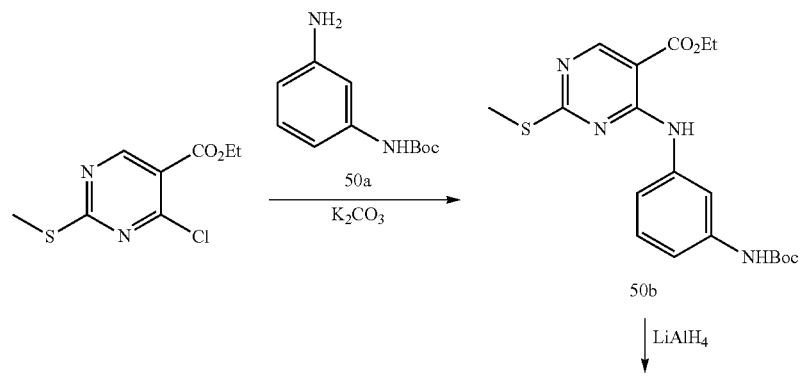

-continued

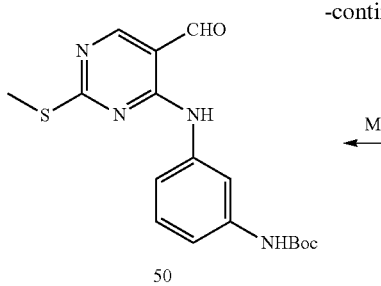
50

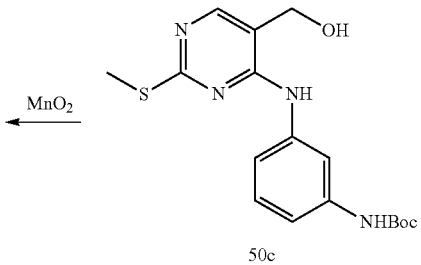
50c

Step 1. A mixture of N-Boc-m-phenylenediamine (50a, prepared according to the procedures reported in: Duceppe, J.-S. et al. *Org. Process. Res. Dev.* 2009, 13, 1156-1160) (280 g, 1.35 mol) and ethyl 4-chloro-2-(methylthio)pyrimidine-5-carboxylate (Sigma-Aldrich; 303.7 g, 1.32 mol) in DMF (200 mL) at RT was treated with $K_2CO_3$ (361 g, 2.6 mol). The mixture was stirred at 80° C. in an oil bath overnight. It was cooled to RT and treated with ice water. The resulting white suspension was filtered and washed with water. The white solid was collected and dried to afford crude ethyl 4-((3-((tert-butoxycarbonyl)amino)phenyl)amino)-2-(methylthio)pyrimidine-5-carboxylate (50c) (450 g, 84% yield). $^1$H NMR (400 MHz, DMSO-d6) δ 10.22 (s, 1H), 9.44 (s, 1H), 8.72 (s, 1H), 7.90 (s, 1H), 7.35-7.33 (m, 1H), 7.28-7.24 (m, 1H), 7.14-7.12 (m, 1H), 4.38-4.33 (q, 2H), 2.51 (s, 3H), 1.48 (s, 9H), 1.35 (t, 3H). m/z (ESI, +ve ion) 405.0 (M+1)$^-$.

Step 2. To a suspension of ethyl 4-((3-((tert-butoxycarbonyl)amino)phenyl)amino)-2-(methylthio)pyrimidine-5-carboxylate (50c) (340 g, 0.84 mol) in THF (200 mL) at −40° C. was added $LiAlH_4$ (2.57 L of 1.0 M solution in THF, 2.57 mol) dropwise. The reaction mixture was stirred at 0° C. for 13 h, then cooled to −20° C. and carefully quenched with solid $Na_2SO_4 \cdot 10H_2O$. The reaction mixture was filtered and rinsed with 2×150 mL of EtOAc. The filtrate was concentrated affording crude tert-butyl (3-((5-(hydroxymethyl)-2-(methylthio)pyrimidin-4-yl)amino)phenyl)carbamate (50d) (280 g, 92% yield). m/z (ESI, +ve ion) 363.0 (M+1)$^+$.

Step 3. At RT, manganese (IV) oxide (358 g, 4.1 mol) was added to a solution of tert-butyl (3-((5-(hydroxymethyl)-2-(methylthio)pyrimidin-4-yl)amino)phenyl)carbamate (50d) (140 g, 386.8 mmol) in $CHCl_3$. After 18 h, the reaction mixture was filtered through a pad of Celite washing with 3×100 mL of $CHCl_3$. The filtrate was concentrated and the residue was purified on a silica gel column (eluted with 15-65% EtOAc in hexanes) to give tert-butyl(3-((5-formyl-2-(methylthio)pyrimidin-4-yl)amino)phenyl)carbamate (60 g, 43% yield) as a yellow solid. $^1$H NMR (400 MHz, CDCl$_3$) δ ppm 10.61 (1H, br. s.), 9.77 (1H, s), 8.44 (1H, s), 7.99 (1H, br. s.), 7.33-7.39 (1H, m), 7.27-7.30 (1H, m), 7.00-7.06 (1H, m), 6.41-6.55 (1H, m), 2.59 (3H, s), 1.53 (9H, s). m/z (ESI, +ve ion) 361.1 (M+1)$^+$.

Preparation of tert-butyl (3-(2-(methylthio)-7-oxopyrido[2,3-d]pyrimidin-8(7H)-yl)phenyl)carbamate (51)

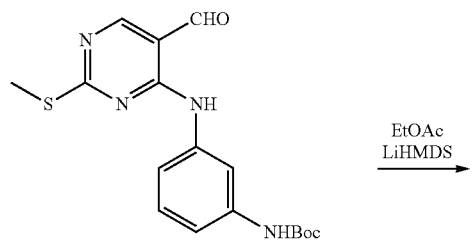
50

EtOAc
LiHMDS
→

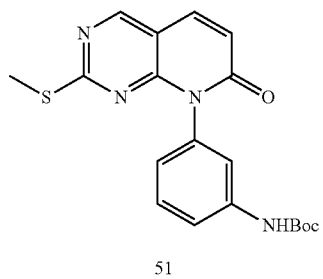
51

LiHMDS (41.6 mL of 1.0 M in THF solution, 41.6 mmol) was added to 2-MeTHF (70 mL) at −78° C. and treated with EtOAc (4.34 mL, 44.4 mmol). The solution was stirred at −78° C. for 10 min, then solid tert-butyl (3-((5-formyl-2-(methylthio)pyrimidin-4-yl)amino)phenyl)carbamate (50) (5.00 g, 13.87 mmol) was added in one portion and the solution was stirred at −78° C. for 10 min then removed from the cooling bath warmed to RT for 3 h. The reaction was cooled in an ice bath and quenched with a saturated solution of $NH_4Cl$ and extracted with EtOAc (2×100 mL), dried over $MgSO_4$, filtered and concentrated. The crude solid was suspended in $Et_2O$ (50 mL) and collected by filtration, washed with $Et_2O$ (2×15 mL) and dried under vacuum affording tert-butyl (3-(2-(methylthio)-7-oxopyrido[2,3-d]pyrimidin-8(7H)-yl)phenyl)carbamate (51) (4.24 g, 11.03 mmol, 80% yield) as a pale yellow solid. $^1$H NMR (400 MHz, CDCl$_3$) δ ppm 8.60-8.65 (1H, m), 7.64-7.71 (1H, m), 7.52 (1H, s), 7.39-7.47 (1H, m), 7.29 (2H, dd, J=8.3, 1.3 Hz), 6.89-6.95 (1H, m), 6.71 (1H, d, J=9.6 Hz), 6.56 (1H, s), 2.19 (3H, s), 1.50 (9H, s). m/z (ESI, +ve ion) 385.0 (M+1)$^+$.

Preparation of tert-butyl (3-(2-(methylsulfinyl)-7-oxopyrido[2,3-d]pyrimidin-8(7H)-yl)phenyl)carbamate (52)

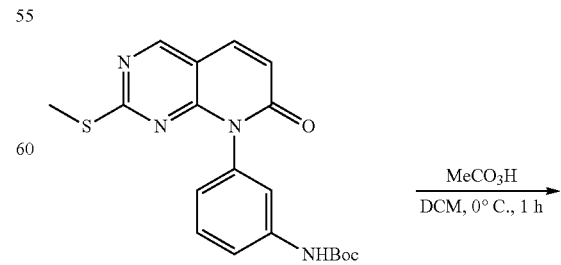
51

MeCO$_3$H
DCM, 0° C., 1 h
→

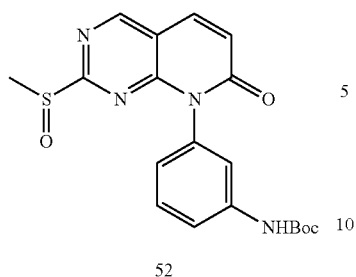

52

At 0° C., a suspension of tert-butyl (3-(2-(methylthio)-7-oxopyrido[2,3-d]pyrimidin-8(7H)-yl)phenyl)carbamate (51) (3.57 g, 9.29 mmol) in DCM (80 mL) was treated with peracetic acid (32 wt % in AcOH, 1.95 mL, 9.29 mmol) slowly dropwise. After 5-10 min, the reaction mixture became a homogeneous yellow solution, and after 20 min, it became a suspension again. After 1 h, the reaction mixture was treated with DCM (50 mL) followed by a solution of aqueous sodium thiosulfate and stirred at 0° C. for 5 min. It was then treated with a saturated solution of NaHCO$_3$, extracted with DCM (6×50 mL), dried over MgSO$_4$, filtered and concentrated affording tert-butyl (3-(2-(methylsulfinyl)-7-oxopyrido[2,3-d]pyrimidin-8(7H)-yl)phenyl)carbamate (52) (2.50 g, 9.70 mmol, 67% yield) as a light yellow crystalline solid. The crude material was used without further purification. $^1$H NMR (400 MHz, DMSO-d$_6$) δ ppm 9.58 (1H, s), 9.28 (1H, s), 8.18 (1H, d, J=9.6 Hz), 7.53 (1H, s), 7.37-7.47 (2H, m), 6.89-6.95 (2H, m), 2.71 (3H, s), 1.46 (9H, s). m/z (ESI, +ve ion) 422.9 (M+Na)$^+$.

Preparation of tert-butyl (3-((5-acetyl-2-(methylthio) pyrimidin-4-yl)amino)phenyl)carbamate (53)

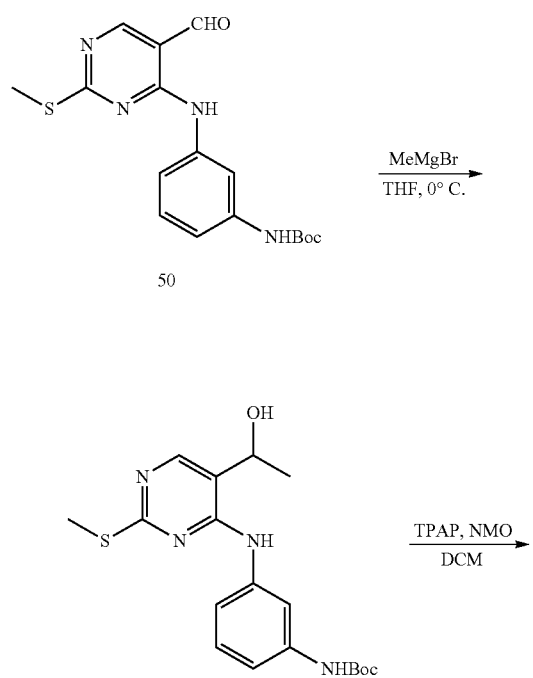

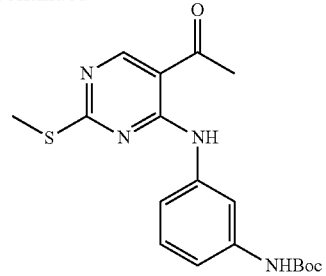

53

Step 1. A 3-necked 2 L RBF equipped with an addition funnel, temperature probe and nitrogen inlet was charged with tert-butyl (3-((5-formyl-2-(methylthio)pyrimidin-4-yl) amino)phenyl)carbamate (50) (25.0 g, 69.4 mmol) and THF (400 mL). The mixture was cooled to 0.5° C. using an ice water bath. Methylmagnesium bromide (3.0 M in Et$_2$O, 74.0 mL, 222 mmol) was added dropwise via an addition funnel over 35 min. The temperature was kept below 8° C. during the addition. The reaction mixture was stirred for 90 min at 0.5° C. and then saturated NH$_4$Cl (aq.) was added slowly via an addition funnel while cooling in ice. The mixture was stirred for 1 h then extracted with EtOAc (2×300 mL). The combined organic layers were washed with brine, dried over anhydrous MgSO$_4$, filtered and concentrated furnishing a yellow solid. The yellow solid was suspended in Et$_2$O (ca. 200 mL), filtered, washed with additional Et$_2$O (2×50 mL), and dried under vacuum overnight affording tert-butyl (3-((5-(1-hydroxyethyl)-2-(methylthio)pyrimidin-4-yl)amino)phenyl) carbamate (23.17 g, 61.5 mmol, 89% yield) as a light yellow solid. m/z (ESI, +ve ion) 377.0 (M+H)$^+$. $^1$H NMR (400 MHz, DMSO-d$_6$) δ ppm 9.34 (1H, s), 8.86 (1H, s), 8.07 (1H, s), 7.80 (1H, s), 7.32 (1H, dd, J=8.1, 1.1 Hz), 7.19 (1H, t, J=8.1 Hz), 6.95-7.07 (1H, m), 5.87 (1H, d, J=4.1 Hz), 4.93 (1H, dd, J=6.5, 4.3 Hz), 2.43 (3H, s), 1.47 (9H, s), 1.40 (3H, d, J=6.5 Hz).

Step 2. Tetrapropylammonium perruthenate (1.05 g, 2.99 mmol) was added to a heterogenous mixture of tert-butyl (3-((5-(1-hydroxyethyl)-2-(methylthio)pyrimidin-4-yl) amino)phenyl)carbamate (22.5 g, 59.8 mmol) and 4-methylmorpholine N-oxide (8.75 g, 74.7 mmol) in DCM (460 mL) at RT. The mixture was stirred at RT for 3 h and concentrated under reduced pressure. The dark solid was dissolved in 10% MeOH in DCM and the material was adsorbed on to silica gel. The material was purified by silica gel pad (2-L sintered medium frit filled halfway with silica gel) eluted with 10% EtOAc in DCM (2 L) followed by 20% EtOAc in DCM (2 L). The fractions containing the desired product was concentrated to afford a white solid. 1.2 L of 1/1 MeOH/EtOAc was added to the solid and the mixture was heated to reflux and cooled to RT slowly. The mixture sat at RT overnight. The white fluffy needles were collected by filtration and washed with EtOAc to afford tert-butyl (3-((5-acetyl-2-(methylthio) pyrimidin-4-yl)amino)phenyl)carbamate (53) (12.66 g, 33.8 mmol, 56% yield). The filtrate was concentrated and the residue was absorbed on to silica gel and the material was purified by silica gel pad (2 L sintered medium frit filled halfway with silica gel) eluted with 10% EtOAc in DCM (2 L) followed by 15% EtOAc in DCM (2 L) followed by 20% EtOAc in DCM. The fractions containing the desired product was concentrated to afford a white solid. 600 mL of 1/1 MeOH/EtOAc was added to the solid and the mixture was heated to reflux and cooled to RT slowly. The mixture was seeded with a small amount of the desired product when the mixture was at 60° C. The mixture sat at RT overnight. The white fluffy needles were collected by filtration and washed with EtOAc to afford additional tert-butyl (3-((5-acetyl-2-

(methylthio)pyrimidin-4-yl)amino)phenyl)carbamate (53) (4.20 g, 11.22 mmol, 18% yield). m/z (ESI, +ve ion) 374.9 (M+H)⁺. ¹H NMR (400 MHz, CDCl₃) δ ppm 11.30 (1H, s), 8.68-8.73 (1H, m), 7.91 (1H, s), 7.30-7.35 (1H, m), 7.05 (1H, dd, J=8.0, 1.0 Hz), 6.46 (1H, br. s.), 2.59 (3H, s), 2.56 (3H, s), 1.52 (9H, s).

Preparation of tert-butyl (3-(5-methyl-2-(methylthio)-7-oxopyrido[2,3-d]pyrimidin-8(7H)-yl)phenyl)carbamate (54)

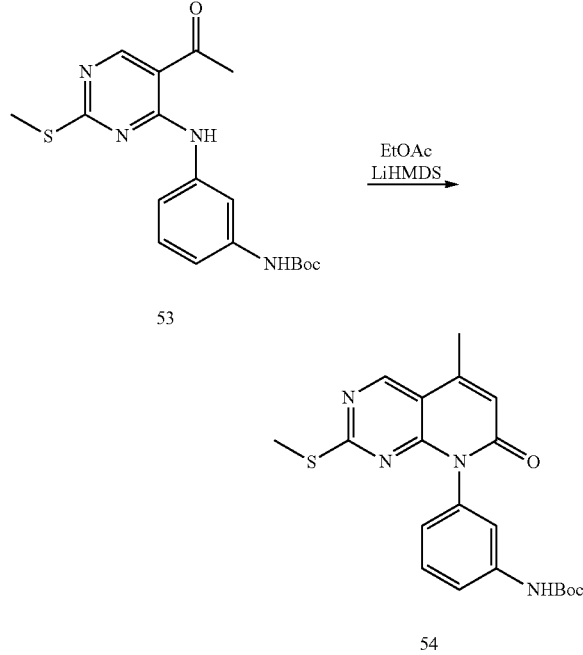

LiHMDS (1.0 M in THF, 27.3 mL, 27.3 mmol) was added to THF (100 mL) at −78° C. and treated with EtOAc (2.50 mL, 25.6 mmol) and stirred 15 min. tert-Butyl (3-((5-acetyl-2-(methylthio)pyrimidin-4-yl)amino)phenyl)carbamate (53) (3.19 g, 8.52 mmol) was added in one portion at −78° C. and the solution warmed to RT and stirred for 3 h. The reaction mixture was quenched with a saturated solution of NH₄Cl and extracted with EtOAc (150 mL), washed with brine and dried over MgSO₄, filtered and concentrated. Purification of the crude residue on silica gel column (10-90% EtOAc in hexanes) afforded the title compound (54) (2.49 g, 6.25 mmol, 73% yield) as a light yellow amorphous solid. m/z (ESI, +ve ion) 398.9 (M+H)⁺. ¹H NMR (400 MHz, CDCl₃) δ ppm 8.72 (1H, s), 7.46 (1H, br. s.), 7.42 (1H, t, J=8.0 Hz), 7.31 (1H, dd, J=8.2, 1.4 Hz), 6.87-6.94 (1H, m), 6.50-6.59 (2H, m), 2.50 (3H, d, J=1.0 Hz), 2.17 (3H, s), 1.50 (9H, s).

Preparation of tert-butyl (3-(6-ethyl-2-(methylthio)-7-oxopyrido[2,3-d]pyrimidin-8(7H)-yl)phenyl)carbamate (55)

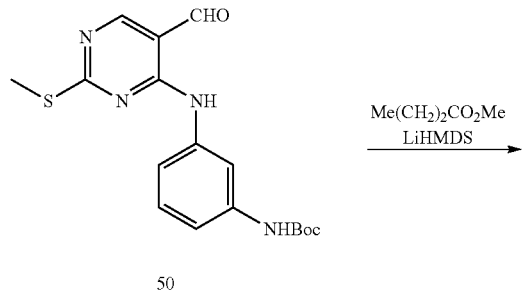

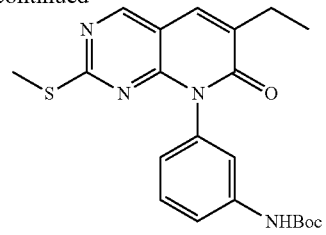

This compound (720 mg, 1.75 mmol, 31% yield) obtained as an off-white solid was prepared according to procedure described for Intermediate 51, using methyl butanoate (1.89 mL, 16.65 mmol) and tert-butyl (3-((5-formyl-2-(methylthio)pyrimidin-4-yl)amino)phenyl)carbamate (50) (2.00 g, 5.55 mmol) as the starting materials. m/z (ESI, +ve ion) 413.0 (M+1)⁺. ¹H NMR (400 MHz, CDCl₃) δ ppm 8.62 (1H, s), 7.47-7.55 (2H, m), 7.39-7.46 (1H, m), 7.29 (1H, d, J=1.4 Hz), 6.92 (1H, dd, J=7.8, 1.0 Hz), 6.57 (1H, br. s.), 2.66 (2H, q, J=7.4 Hz), 2.19 (3H, s), 1.50 (9H, s), 1.23-1.31 (3H, m).

Preparation of tert-butyl (3-(5-methyl-2-(methylsulfonyl)-7-oxopyrido[2,3-d]pyrimidin-8(7H)-yl)phenyl)carbamate (56)

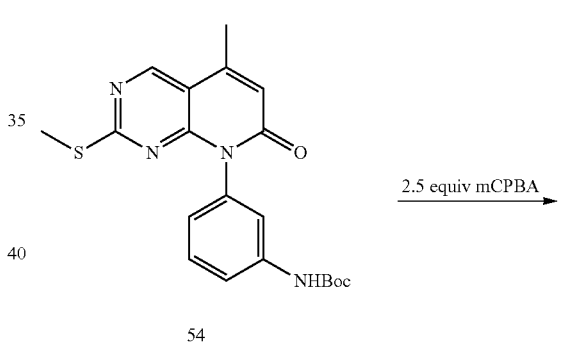

At RT, tert-butyl (3-(5-methyl-2-(methylthio)-7-oxopyrido[2,3-d]pyrimidin-8(7H)-yl)phenyl)carbamate (54) (440 mg, 1.10 mmol) in DCM (10 mL) was treated with MCPBA (75 wt. %, 681 mg, 2.76 mmol) and stirred for 90 min. The reaction mixture was diluted with DCM (25 mL), treated with ice and 1 N NaOH (30 mL). The DCM layer was separated and the aqueous layer was extracted with an additional amount of DCM (2×20 mL), dried over Na₂SO₄ and concentrated to furnish tert-butyl (3-(5-methyl-2-(methylsulfonyl)-7-oxopyrido[2,3-d]pyrimidin-8(7H)-yl)phenyl)carbamate (451 mg, 1.05 mmol, 95% yield) as an off-white foam. The crude material was used without purification. m/z (ESI, +ve ion) 453.0 (M+Na)⁺. ¹H NMR (400 MHz, CDCl₃) δ ppm 9.11 (1H, s), 7.60 (1H, br. s.), 7.45 (1H, t, J=8.0 Hz), 7.23 (1H, dt, J=8.2, 1.0 Hz), 6.91 (1H, ddd, J=7.9, 1.9, 0.8 Hz), 6.80 (1H, d, J=1.4 Hz), 6.60 (1H, s), 3.04 (3H, s), 2.60 (3H, d, J=1.2 Hz), 1.49 (9H, s).

Preparation of Intermediate 57

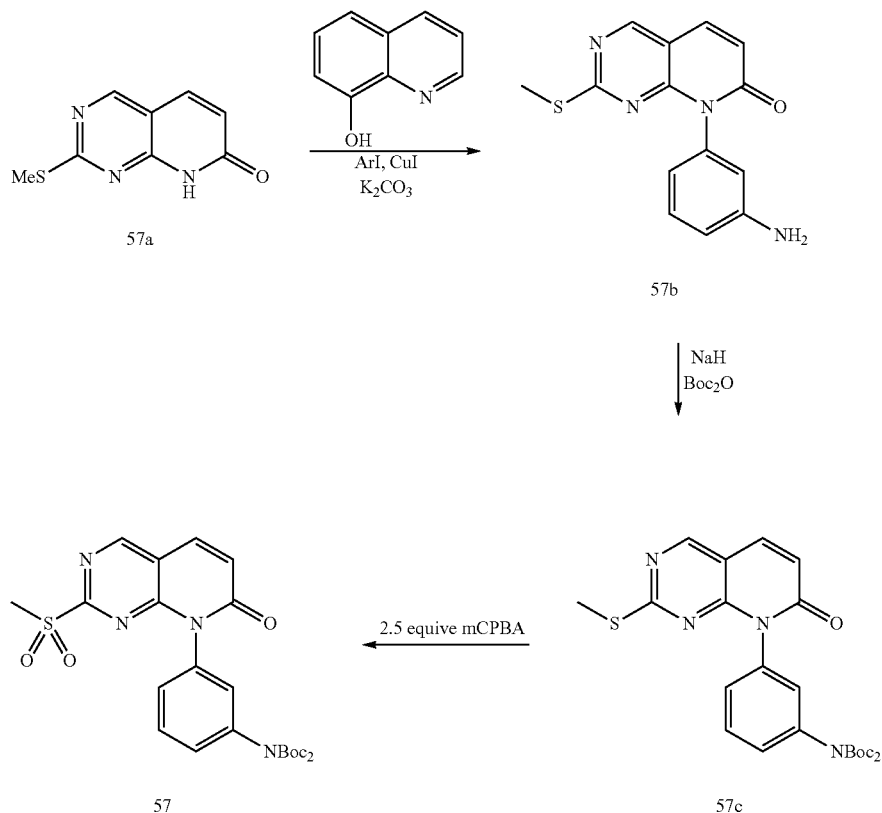

Step 1. In a 20 mL glass microwave tube, 2-(methylthio)pyrido[2,3-d]pyrimidin-7(8H)-one (57a, Matrix Scientific; 500 mg, 2.59 mmol) was treated with K₂CO₃ (715 mg, 5.18 mmol), CuI (99 mg, 0.52 mmol) and 4,7-dimethoxy-1,10-phenanthroline (Sigma Aldrich, 187 mg, 0.77 mmol) followed by purging with argon for 3 min. The solids were then treated with DMSO (6.0 mL) and 3-iodoaniline (0.31 mL, 2.59 mmol). The tube was sealed and heated to 110° C. for 20 h. The reaction mixture was treated with water and extracted with EtOAc (3×50 mL) and the suspension filtered through a pad of Celite. The crude material was purified on a silica gel column (1-20% MeOH in DCM) affording enriched product. It was then repurified on a Gilson preparatory HPLC (Silicycle Silichrome XT C₁₈ column; 30×150 mm, 5µ, 5-95% 0.1% TFA/CH₃CN in 0.1% TFA/water) affording 8-(3-aminophenyl)-2-(methylthio)pyrido[2,3-d]pyrimidin-7(8H)-one 2,2,2-trifluoroacetate (57b) (150 mg, 0.38 mmol, 14% yield) as a light yellow crystalline solid. m/z (ESI, +ve ion) 285.0 (M+1)⁺.

Step 2. At 0° C., 8-(3-aminophenyl)-2-(methylthio)pyrido[2,3-d]pyrimidin-7(8H)-one 2,2,2-trifluoroacetate (57b) (150 mg, 0.38 mmol) in THF (5.0 mL), and treated with NaH (60 wt. % dispersion in mineral oil, 60 mg, 1.51 mmol) in one portion. It was stirred at this temperature for 30 min then treated with di-1-butyldicarbonate (205 mg, 0.94 mmol) and heated to 70° C. for 6 h. The reaction mixture was cooled to RT, quenched with ice water and extracted with EtOAc (2×30 mL), dried over MgSO₄, concentrated and purified on silica gel column (10-90% EtOAc in hexanes) affording bis(tert-butyl(3-(2-(methylthio)-7-oxopyrido[2,3-d]pyrimidin-8(7H)-yl)phenyl)) carbamate (57c) (158 mg, 0.33 mmol, 87% yield) as a yellow film. m/z (ESI, +ve ion) 485.1 (M+1)⁺. ¹H NMR (400 MHz, CDCl₃) δ ppm 8.65 (1H, s), 7.69 (1H, d, J=9.6 Hz), 7.52 (1H, t, J=8.0 Hz), 7.24-7.29 (1H, m), 7.20 (1H, d, J=7.8 Hz), 7.07 (1H, t, J=1.8 Hz), 6.71 (1H, d, J=9.4 Hz), 2.22 (3H, s), 1.43 (18H, s).

Step 3. Bis(tert-butyl(3-(2-(methylthio)-7-oxopyrido[2,3-d]pyrimidin-8(7H)-yl)phenyl))carbamate (57c, 157 mg, 0.32 mmol) was treated with DCM (5.0 mL) followed by MCPBA, 75% max., 200 mg, 0.81 mmol) and stirred at RT for 1 h. LC-MS showed clean formation of the desired product m/z (ESI, +ve ion) 539.0 (M+Na)⁺. The reaction mixture was diluted with 100 mL of DCM, washed with 10 mL of sat. NaHCO₃ followed by 10 mL of brine. The organic solution was dried over Na₂SO₄, filtered and concentrated to give Intermediate 57 as an off white solid. The crude material was used without purification.

Preparation of tert-butyl (4-fluoro-3-((5-formyl-2-(methylthio)pyrimidin-4-yl)amino)phenyl)carbamate (58)

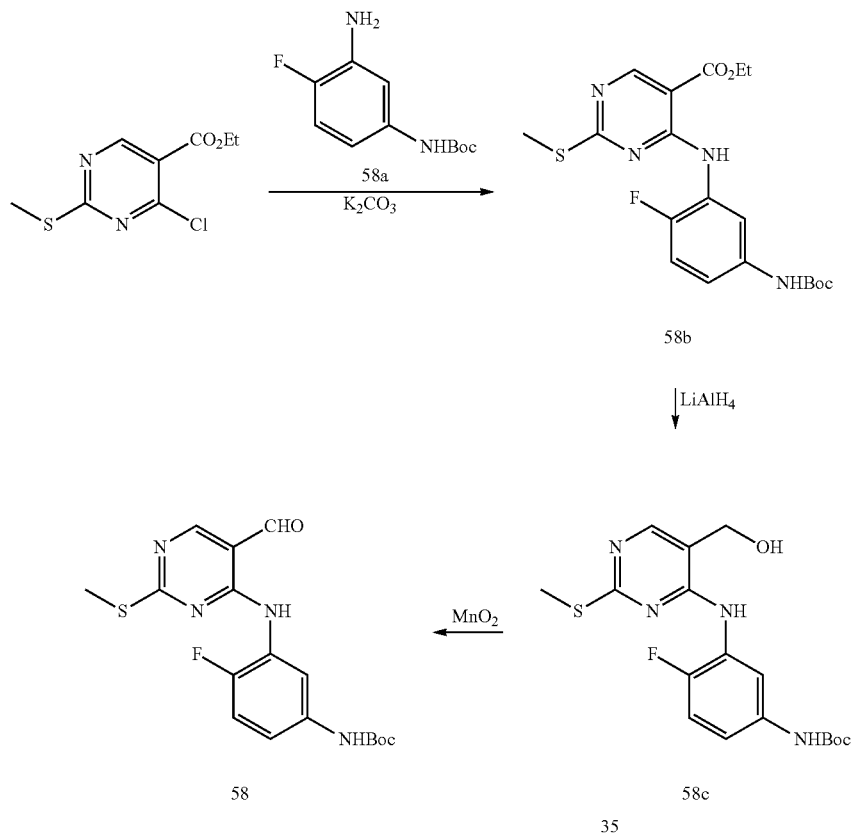

The title compound was prepared according to the procedures described for Intermediate 50, starting from tert-butyl (3-amino-4-fluorophenyl)carbamate (58a; prepared according to the reported protocol in Kuramoto, Y. et al. *J. Med. Chem.* 2003, 46, 1905-1917).

Ethyl 4-((5-(((tert-butoxycarbonyl)amino)-2-fluorophenyl)amino)-2-(methylthio)pyrimidine-5-carboxylate (58b): m/z (ESI, +ve ion) 422.9 (M+1)$^+$. $^1$H NMR (400 MHz, DMSO-d$_6$) δ ppm 10.36 (1H, s), 9.48 (1H, s), 8.76 (1H, s), 8.48 (1H, d, J=5.3 Hz), 7.19-7.28 (1H, m), 7.07-7.15 (1H, m), 4.37 (2H, q, J=7.2 Hz), 2.49 (3H, s), 1.45-1.51 (9H, s), 1.35 (3H, t, J=7.0 Hz). $^{19}$F NMR (376 MHz, DMSO-d$_6$) δ ppm-134.43 (1F, s).

tert-Butyl (4-fluoro-3-((5-(hydroxymethyl)-2-(methylthio)pyrimidin-4-yl)amino)phenyl)carbamatecarbamate (58c): m/z (ESI, +ve ion) 380.0 (M+1)$^+$. $^1$H NMR (400 MHz, CDCl$_3$) δ ppm 8.33 (1H, d, J=5.7 Hz), 7.75-7.81 (1H, m), 6.84-6.94 (2H, m), 4.50 (2H, s), 2.40-2.44 (3H, m), 1.39-1.43 (9H, s).

tert-Butyl(4-fluoro-34(5-formyl-2-(methylthio)pyrimidin-4-yl)amino)phenyl)carbamate (58): m/z (ESI, +ve ion) 379.0 (M+1)$^+$. $^1$H NMR (400 MHz, CDCl$_3$) δ ppm 10.78 (1H, br. s.), 9.81 (1H, s), 8.60 (1H, d, J=4.7 Hz), 8.48 (1H, s), 7.04-7.11 (1H, m), 6.97-7.03 (1H, m), 6.43 (1H, br. s.), 2.61 (3H, s), 1.52 (9H, s). $^{19}$F NMR (377 MHz, CDCl$_3$) δ ppm-133.41 (1F, s).

Preparation of tert-butyl (4-fluoro-3-(2-(methylthio)-7-oxopyrido[2,3-d]pyrimidin-8(7H)-yl)phenyl)carbamate (59)

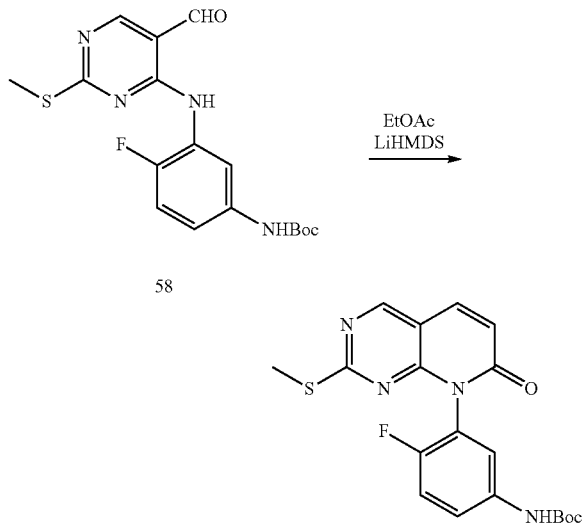

This compound (270 mg, 59% yield) as a light yellow crystalline solid was prepared according to the procedures described for Intermediate 51, using tert-butyl (4-fluoro-3-((5-formyl-2-(methylthio)pyrimidin-4-yl)amino)phenyl)carbamate (58) (430 mg, 1.14 mmol) as the starting material. m/z (ESI, +ve ion) 403.0 (M+1)+. $^1$H NMR (400 MHz, CDCl$_3$) δ ppm 8.64 (1H, s), 7.70 (1H, d, J=9.6 Hz), 7.55 (1H, br. s.), 7.28-7.35 (1H, m), 7.17 (1H, t, J=9.0 Hz), 6.72 (1H, d, J=9.6 Hz), 6.56 (1H, br. s.), 2.22 (3H, s), 1.49 (9H, s). $^{19}$F NMR (376 MHz, DMSO-d$_6$) δ ppm-126.87 (1F, s).

Preparation of tert-butyl (4-fluoro-3-(2-(methylsulfinyl)-7-oxopyrido[2,3-d]pyrimidin-8(7H)-yl)phenyl)carbamate (60)

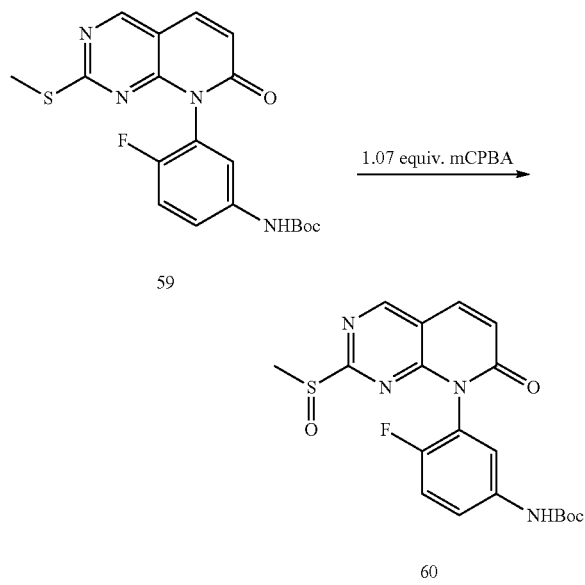

At 0° C., a suspension of tert-butyl (4-fluoro-3-(2-(methylthio)-7-oxopyrido[2,3-d]pyrimidin-8(7H)-yl)phenyl)carbamate (59) (270 mg, 0.67 mmol) in DCM (10 mL) was treated with MCPBA (77 wt. %, 161 mg, 0.72 mmol) in one portion and stirred at 0° C. for 1 h. The reaction mixture was diluted with DCM (50 mL), and treated with ice and water (30 mL) followed by 10% Na$_2$CO$_3$ (ca. 10 mL). The DCM layer was separated and the aqueous layer was extracted with an additional amount of DCM (2×50 mL), dried over Na$_2$SO$_4$ and concentrated to give crude tert-butyl (4-fluoro-3-(2-(methylsulfinyl)-7-oxopyrido[2,3-d]pyrimidin-8(7H)-yl)phenyl)carbamate (60) (369 mg) as a light yellow solid. m/z (ESI, +ve ion) 440.9 (M+Na)+. $^1$H NMR (400 MHz, DMSO-d$_6$) δ ppm 9.63 (1H, br. s.), 8.24 (1H, d, J=9.6 Hz), 7.68 (1H, d, J=3.5 Hz), 7.44-7.52 (1H, m), 7.33-7.41 (1H, m), 6.95-7.01 (1H, m), 5.76 (1H, s), 2.72-2.78 (3H, m), 1.47 (9H, s). $^{19}$F NMR (376 MHz, DMSO-d$_6$) δ ppm-129.58 (1F, s).

Example 1

N-(3-(2-((2-methoxy-4-(4-methyl-1-piperazinyl)phenyl)amino)-7-oxopyrido[2,3-d]pyrimidin-8(7H)-yl)phenyl)-2-propenamide

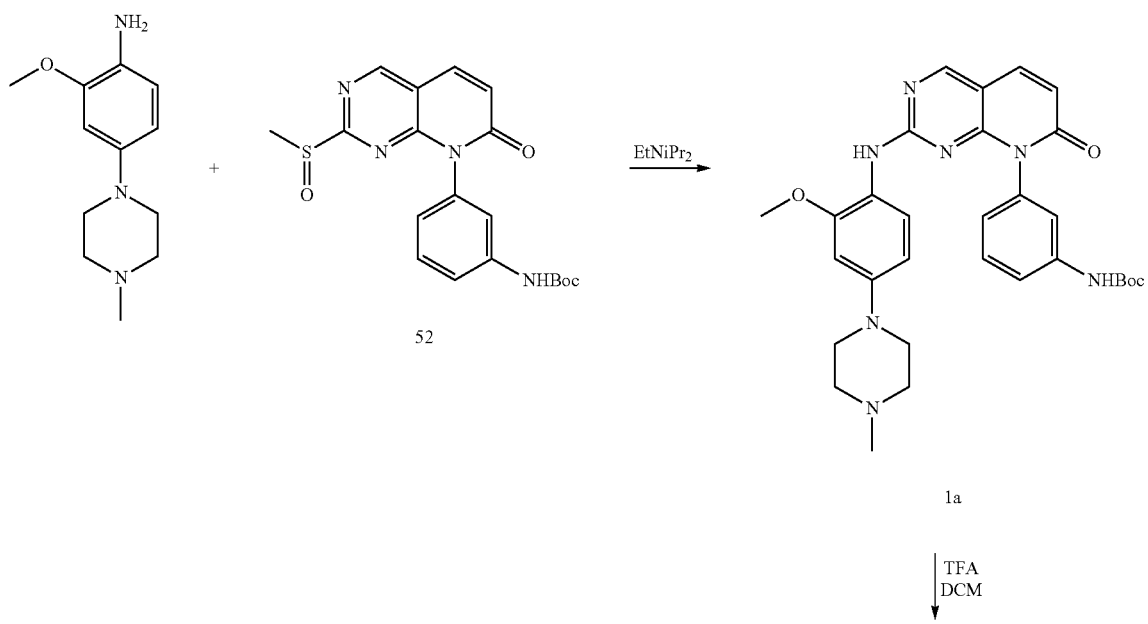

-continued

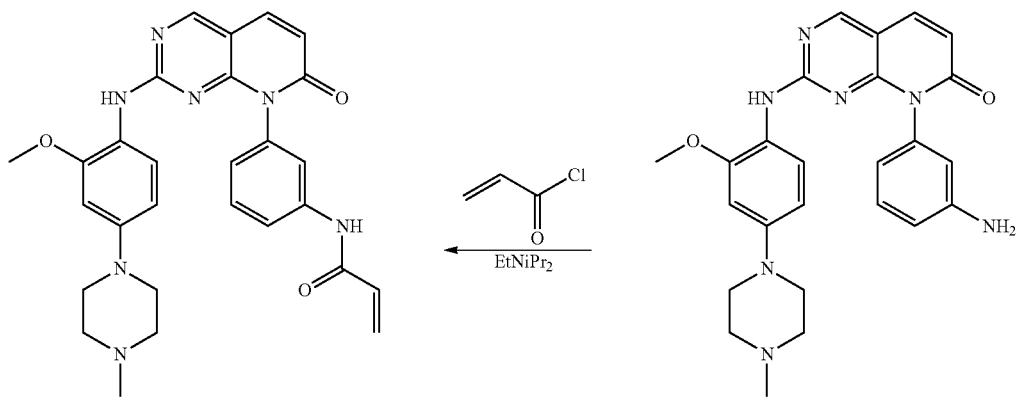

Step 1. To a mixture of 2-methoxy-4-(4-methylpiperazin-1-yl)aniline (Combi-Blocks Inc, Cat#: SS-3744; 342 mg, 1.55 mmol) and tert-butyl (3-(2-(methylsulfinyl)-7-oxopyrido[2,3-d]pyrimidin-8(7H)-yl)phenyl)carbamate (52) (521 mg, 1.30 mmol) in tert-butanol (10 mL, 105 mmol) was added DIEA (0.57 mL, 3.25 mmol). The reaction mixture was heated at 80° C. in an oil bath for 21 h. The resulting brown suspension was concentrated under reduced pressure and the crude solid was suspended in Et$_2$O (ca. 20 mL) and filtered affording the crude material of tert-butyl (3-(2-((2-methoxy-4-(4-methylpiperazin-1-yl)phenyl)amino)-7-oxopyrido[2,3-d]pyrimidin-8(7H)-yl)phenyl)carbamate (1a) as a green solid. m/z (ESI, +ve ion) 558.0 (M+H)$^+$. $^1$H NMR (400 MHz, DMSO-d$_6$) δ ppm 9.57 (1H, s), 8.73 (1H, s), 8.14 (1H, s), 7.89 (1H, d, J=9.4 Hz), 7.57 (1H, d, J=8.4 Hz), 7.42 (3H, t, J=8.0 Hz), 7.28 (1H, d, J=8.8 Hz), 6.87 (1H, d, J=8.6 Hz), 6.53 (1H, d, J=2.3 Hz), 6.43 (1H, d, J=9.4 Hz), 6.05 (1H, br. s.), 3.73-3.82 (3H, m), 3.06 (4H, br. s.), 2.36-2.47 (4H, 2.15-2.26 (3H, s), 1.45 (9H, s).

Step 2. The crude 1a from above was treated with DCM (20 mL) and TFA (20 mL) and stirred at RT for 30 min. The reaction mixture was concentrated under reduced pressure (rotary evaporator) and purified on a silica gel column (1-20% 2M NH$_3$/MeOH in DCM) affording 8-(3-aminophenyl)-2-((2-methoxy-4-(4-methylpiperazin-1-yl)phenyl)amino)pyrido[2,3-d]pyrimidin-7(8H)-one (1b) (470 mg, 1.03 mmol, 79% yield) as a brown amorphous solid. m/z (ESI, +ve ion) 458.0 (M+H)$^+$. $^1$H NMR (400 MHz, MeOH-d4) δ ppm 8.67 (1H, s), 7.88 (1H, d, J=9.4 Hz), 7.63 (1H, d, J=8.2 Hz), 7.32 (1H, t, J=8.0 Hz), 6.91 (1H, dd, J=8.1, 1.5 Hz), 6.59-6.65 (2H, m), 6.53-6.59 (1H, m), 6.46-6.52 (1H, m), 6.24 (1H, br. s.), 3.88 (3H, s), 3.21 (4H, br. s.), 2.84 (4H, br. s.), 2.53 (3H, s).

Step 3. 8-(3-Aminophenyl)-2-((2-methoxy-4-(4-methylpiperazin-1-yl)phenyl)amino)pyrido[2,3-d]pyrimidin-7(8H)-one (1b) (2.17 g, 4.74 mmol) in DCM (30 mL) and THF (30 mL) at 0° C. was treated with DIEA (1.66 mL, 9.49 mmol) and acryloyl chloride (0.46 mL, 5.69 mmol) dropwise over 15 min and stirred at 0° C. After 1.5 h, additional acryloyl chloride (0.20 mL) was added slowly over 10 min then the suspension was stirred at 0° C. for another 20 min. Additional acryloyl chloride (0.1 mL) was added and the reaction mixture stirred another 15 min. The reaction mixture was treated with a saturated solution of NaHCO$_3$, extracted with DCM (5×100 mL), dried over Na$_2$SO$_4$, filtered and concentrated. Purification of the crude residue on a silica gel column (1-20% MeOH in DCM) afforded the desired product as a yellow solid. This material was treated with 20 mL of EtOH and the slurry was filtered through a medium porosity sintered glass frit and washed with additional EtOH (10 mL) and Et$_2$O (3×10 mL) affording N-(3-(2-((2-methoxy-4-(4-methylpiperazin-1-yl)phenyl)amino)-7-oxopyrido[2,3-d]pyrimidin-8(7H)-yl)phenyl)acrylamide (1) (680 mg, 1.33 mmol, 28% yield) as a yellow solid after drying overnight at 36° C. in a vacuum oven. m/z (ESI, +ve ion) 512.0 (M+H)$^+$. $^1$H NMR (400 MHz, DMSO-d$_6$) δ ppm 10.35 (1H, s), 8.75 (1H, br. s.), 8.17 (1H, br. s.), 7.92 (2H, d, J=9.4 Hz), 7.59 (1H, br. s.), 7.52 (1H, t, 0.1=8.1 Hz), 7.29 (1H, d, J=9.0 Hz), 7.01 (1H, d, J=8.0 Hz), 6.54 (1H, br. s.), 6.37-6.50 (2H, m), 6.20-6.33 (1H, m), 6.03 (1H, br. s.), 5.77 (1H, d, J=10.0 Hz), 3.78 (3H, s), 3.07 (4H, br. s.), 2.43 (3H, s), 2.34 (4H, br. s.).

Example 2

N-(3-(2-((2-methoxy-4-(4-morpholinyl)phenyl)amino)-7-oxopyrido[2,3-d]pyrimidin-8(7H)-yl)phenyl)-2-propenamide

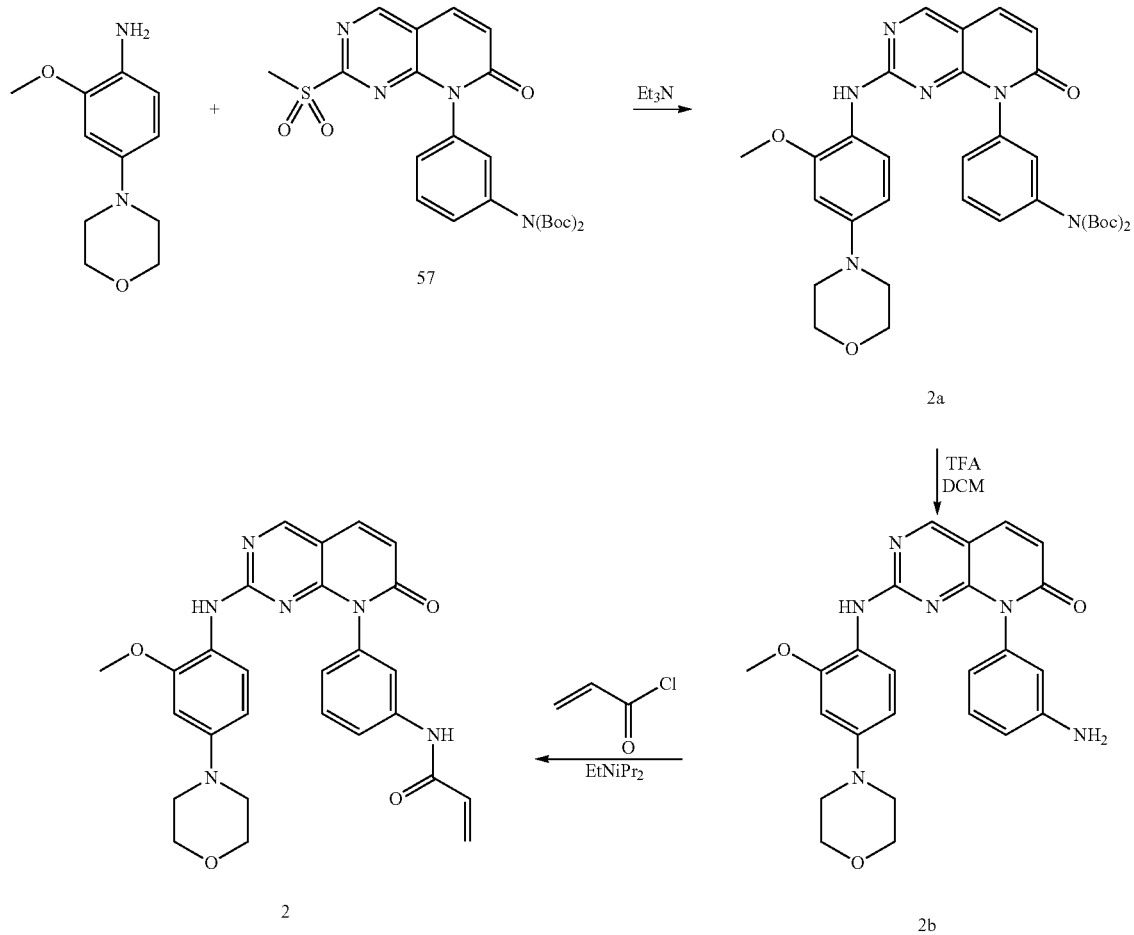

Step 1. 2-Methoxy-4-morpholinoaniline (Matrix Scientific, Columbia, S.C.; 135 mg, 0.65 mmol) and bis(tert-butyl (3-(2-(methylsulfonyl)-7-oxopyrido[2,3-d]pyrimidin-8 (7H)-yl)phenyl))carbamate (57) (167 mg, 0.32 mmol) were treated with tert-butanol (2.0 mL) and Et$_3$N (0.14 mL, 0.97 mmol) and heated to 110° C. for 75 min. The reaction mixture was concentrated and the crude bis(tert-butyl (3-(2-((2-methoxy-4-morpholinophenyl)amino)-7-oxopyrido[2,3-d]pyrimidin-8(7H)-yl)phenyl))carbamate (2a) was used in the next step without further purification. m/z (ESI, +ve ion) 668.1 (M+Na)$^+$.

Step 2. Crude bis(tert-butyl (3-(2-((2-methoxy-4-morpholinophenyl)amino)-7-oxopyrido[2,3-d]pyrimidin-8(7H)-yl)phenyl))carbamate (2a) was treated with DCM (5 mL) and TFA (3 mL) and stirred at RT for 15 min. The reaction mixture was concentrated and purified on a Gilson preparatory HPLC (Silicycle Silichrome XT C18 column; 30×150 mm, 5 u, 5-95% 0.1% TFA/CH$_3$CN in 0.1% TFA/water) affording 8-(3-aminophenyl)-2-((2-methoxy-4-morpholinophenyl)amino)pyrido[2,3-d]pyrimidin-7(8H)-one 2,2,2-trifluoroacetate (2b, 74 mg, 0.13 mmol, 41% yield) as a brown amorphous solid after drying in a genevac overnight. m/z (ESI, +ve ion) 446.1 (M+Na)$^+$. $^1$H NMR (400 MHz, MeOH-d4) δ ppm 8.86 (1H, s), 8.05 (1H, d, J=9.6 Hz), 7.51-7.58 (1H, m), 7.32 (1H, dt, J=7.6, 1.3 Hz), 7.15-7.21 (2H, m), 6.90 (1H, d, J=8.6 Hz), 6.71 (1H, d, J=9.6 Hz), 6.67 (1H, d, J=2.5 Hz), 6.53 (1H, dd, J=8.7, 2.6 Hz), 3.87-3.93 (5H, m), 3.68 (3H, s), 3.18-3.24 (4H, m).

Step 3. 8-(3-Aminophenyl)-2-((2-methoxy-4-morpholinophenyl)amino)pyrido[2,3-d]pyrimidin-7(8H)-one 2,2,2-trifluoroacetate (2b, 63 mg, 0.11 mmol) was treated with DCM (5.0 mL), cooled to 0° C. and treated with DIEA (0.06 mL, 0.34 mmol) and acryloyl chloride (9.16 μL, 0.113 mmol) and stirred at 0° C. for 40 min. The reaction mixture was treated with ice and water and then a saturated solution of NaHCO$_3$. It was extracted with DCM (3×25 mL), dried over Na$_2$SO$_4$, filtered and concentrated. The crude residue was purified on a Gilson prepatory HPLC (Silicycle Silichrome XT C18 column; 30×150 mm, 5μ, 20-95% 0.1% TFA/CH$_3$CN in 0.1% TFA/water) affording N-(3-(2-((2-methoxy-4-morpholinophenyl)amino)-7-oxopyrido[2,3-d]pyrimidin-8(7H)-yl)phenyl)acrylamide (2) (26 mg, 0.054 mmol, 47% yield) as a light orange amorphous solid after concentration of the sample containing fractions, treatment with a saturated solution of NaHCO$_3$, extraction with DCM (3×25 mL), drying over Na$_2$SO$_4$, filtration and drying under vacuum. m/z (ESI, +ve ion) 500.1 (M+H)$^+$. $^1$H NMR (400 MHz, DMSO-d$_6$) δ ppm 10.33 (1H, s), 8.88 (1H, s), 8.04 (1H, d, J=9.6 Hz), 7.66-7.70 (1H, m), 7.64 (1H, d, J=8.2 Hz), 7.45 (1H, t, J=8.0 Hz), 6.94-7.00 (1H, m), 6.90 (1H, d, J=8.6 Hz), 6.67 (1H, d, J=9.6 Hz), 6.59 (1H, d, J=2.5 Hz), 6.42-6.51 (1H, m), 6.40 (1H, dd, J=8.8, 2.5 Hz), 6.22-6.32 (1H, m), 5.77-5.82 (1H, m), 3.71-3.80 (4H, m), 3.63 (3H, s), 3.04-3.14 (4H, m).

Example 3

(2E)-N-(3-(2-((2-methoxy-4-(4-methyl-1-piperazinyl)phenyl)amino)-7-oxopyrido[2,3-d]pyrimidin-8(7H)-yl)phenyl)-2-butenamide

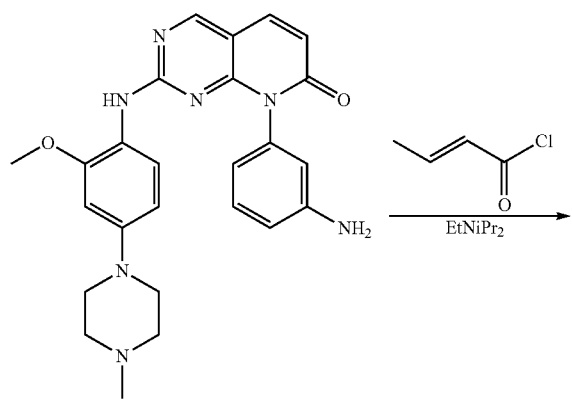

1b

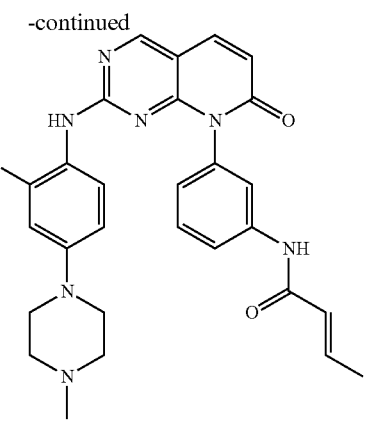

3

This compound (10 mg, 14% yield) as a yellow amorphous solid was prepared according to the procedures described for Example 1, using 8-(3-aminophenyl)-2-((2-methoxy-4-(4-methylpiperazin-1-yl)phenyl)amino)pyrido[2,3-d]pyrimidin-7(8H)-one 2,2,2-trifluoroacetate (1b, 78 mg, 0.14 mmol) and (E)-crotonoyl chloride (Sigma Aldrich, 0.013 mL, 0.14 mmol) as the starting materials. m/z (ESI, +ve ion) 526.3 (M+H)$^+$. $^1$H NMR (400 MHz, DMSO-d$_6$) δ ppm 10.17 (1H, s), 8.76 (1H, s), 8.17 (1H, br. s.), 7.92 (1H, d, J=9.4 Hz), 7.84 (1H, br. s.), 7.61 (1H, s), 7.50 (1H, t, J=8.0 Hz), 7.29 (1H, d, J=8.8 Hz), 6.99 (1H, d, J=7.6 Hz), 6.76-6.86 (1H, m), 6.54 (1H, s), 6.46 (1H, d, J=9.4 Hz), 6.14 (1H, d, J=15.1 Hz), 6.05 (1H, d, J=16.0 Hz), 3.79 (3H, s), 3.05 (4H, br. 2.45 (4H, d, J=4.5 Hz), 2.24 (3H, s), 1.85-1.91 (3H, m).

Example 4

N-(3-(2-((4-(4-methyl-1-piperazinyl)phenyl)amino)-7-oxopyrido[2,3-d]pyrimidin-8(7H)-yl)phenyl)-2-propenamide

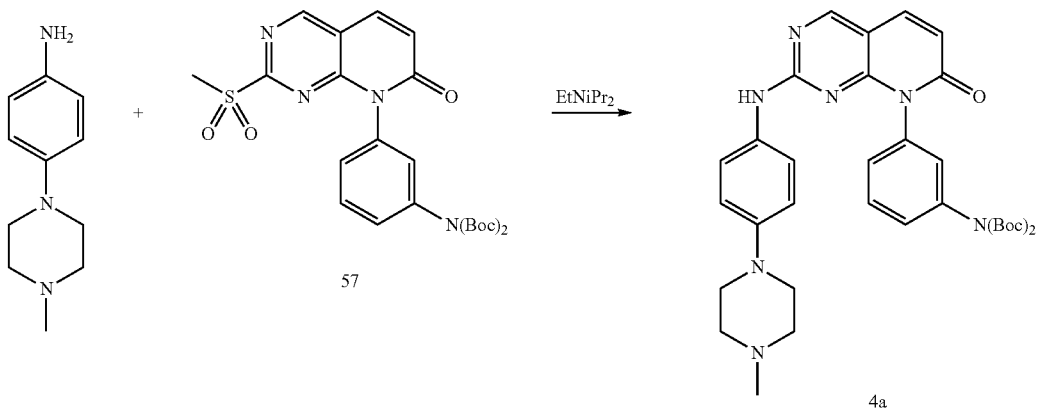

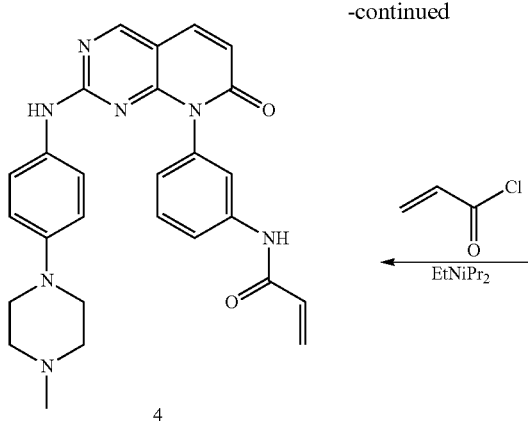

4

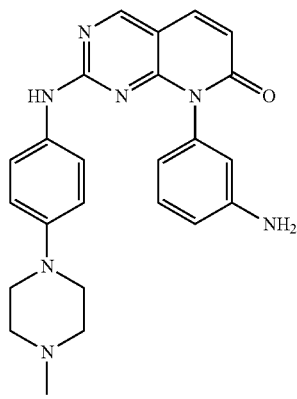

4b

This compound was isolated as an orange amorphous solid according to the procedures described for Example 2, using 8-(3-aminophenyl)-2-((2-methoxy-4-(4-methylpiperazin-1-yl)phenyl)amino)pyrido[2,3-d]pyrimidin-7(8H)-one 2,2,2-trifluoroacetate (57) and 4-(4-methylpiperazino)aniline (Maybridge, Cambridge, UK) as the starting materials. m/z (ESI, +ve ion) 482.1 (M+H)$^+$. $^1$H NMR (400 MHz, DMSO-d$_6$) δ ppm 10.40 (1H, s), 9.88 (1H, br. s.), 8.78 (1H, s), 7.92 (2H, d, J=9.4 Hz), 7.62 (1H, s), 7.56 (1H, t, J=8.1 Hz), 7.15-7.27 (2H, m), 7.00-7.07 (1H, m), 6.57 (2H, br. s.), 6.40-6.50 (2H, m), 6.22-6.31 (1H, m), 5.75-5.83 (1H, m), 2.98 (4H, m), 2.43 (4H, m), 2.23 (3H, s).

Example 5

N-(3-(2-(((2-methoxy-4-(4-methyl-1-piperazinyl)phenyl)amino)-5-methyl-7-oxopyrido[2,3-d]pyrimidin-8(7H)-yl)phenyl)-2-propenamide

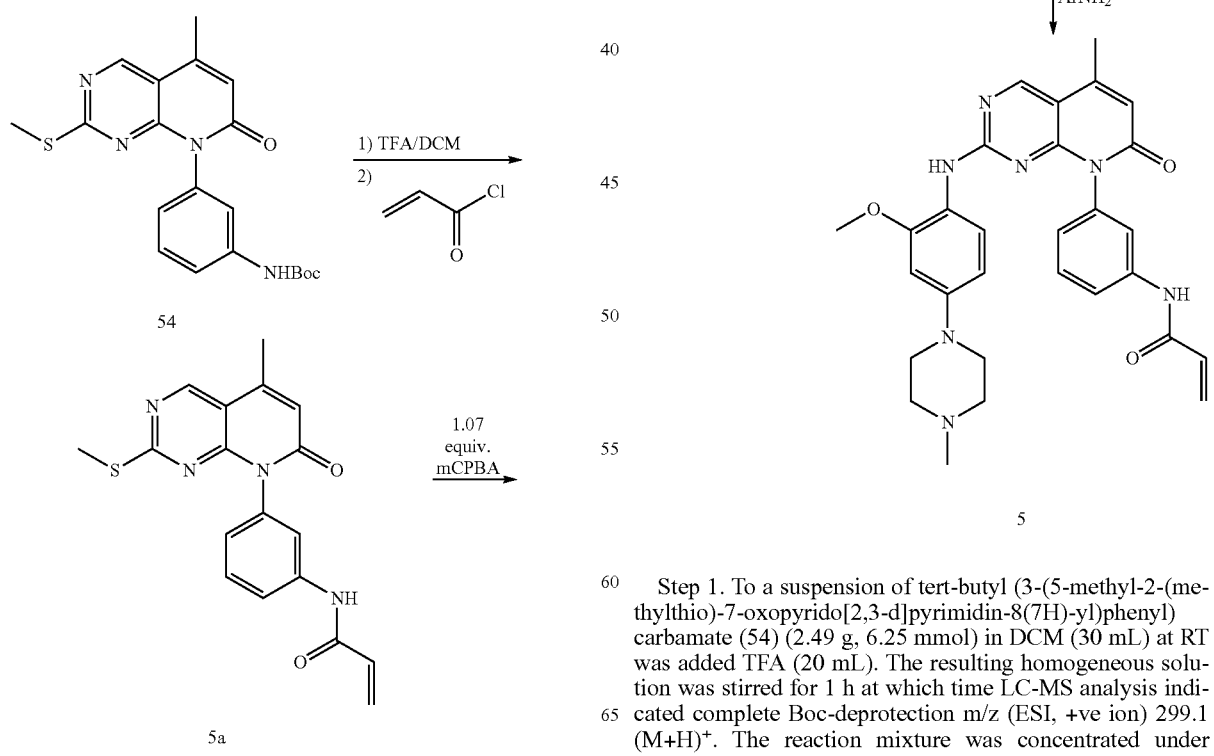

Step 1. To a suspension of tert-butyl (3-(5-methyl-2-(methylthio)-7-oxopyrido[2,3-d]pyrimidin-8(7H)-yl)phenyl)carbamate (54) (2.49 g, 6.25 mmol) in DCM (30 mL) at RT was added TFA (20 mL). The resulting homogeneous solution was stirred for 1 h at which time LC-MS analysis indicated complete Boc-deprotection m/z (ESI, +ve ion) 299.1 (M+H)$^+$. The reaction mixture was concentrated under reduced pressure (rotary evaporator). The residue was dissolved in DCM (50 mL), cooled to 0° C. and treated with DIEA (5.43 mL, 31.2 mmol) followed by acryloyl chloride (0.61 mL, 7.50 mmol). This resulted in a yellow suspension after stirring 25 min. LC-MS indicated clean conversion to the desired product m/z (ESI, +ve ion) 353.1 (M+H)'. The reaction mixture was quenched by the addition of an aqueous solution of 1.0 M $K_2CO_3$ and the resulting light yellow suspension was filtered through a medium porosity sintered glass frit washing with water and $Et_2O$ affording N-(3-(5-methyl-2-(methylthio)-7-oxopyrido[2,3-d]pyrimidin-8(7H)-yl)phenyl)acrylamide (5a; 2.17 g, 6.15 mmol, 98% yield) as a light yellow solid after drying under high vacuum. m/z (ESI, +ve ion) 353.1 (M+H)$^+$. $^1$H NMR (400 MHz, DMSO-$d_6$) δ ppm 10.31 (1H, s), 8.98 (1H, s), 7.64-7.71 (2H, m), 7.48 (1H, t, J=8.0 Hz), 7.01 (1H, d, J=8.2 Hz), 6.59 (1H, d, J=1.2 Hz), 6.44 (1H, dd, J=17.0, 10.2 Hz), 6.26 (1H, dd, J=16.8, 2.0 Hz), 5.71-5.81 (1H, m), 2.51 (3H, s), 2.20 (3H, s).

Steps 2 and 3. To a suspension of N-(3-(5-methyl-2-(methylthio)-7-oxopyrido[2,3-d]pyrimidin-8(7H)-yl)phenyl) acrylamide (5a; 5.15 g, 14.63 mmol) in DCM (100 mL) at 0° C. was added MCPBA (77 wt. %, 3.51 g, 15.65 mmol) in one portion. The resulting suspension was stirred at 0° C. for 1 h. The reaction mixture was diluted with DCM (100 mL) and treated with an ice cold solution of 1.0 M $K_2CO_3$. The aqueous layer was extracted with DCM (2×100 mL). The organic extracts were dried over $Na_2SO_4$, filtered and concentrated affording crude N-(3-(5-methyl-2-(methylsulfinyl)-7-oxopyrido[2,3-d]pyrimidin-8(7H)-yl)phenyl)acrylamide (5b; 1.09 g, 2.96 mmol, 20% yield) as a light yellow foam. The aqueous layer contained suspended material so it was filtered through a medium porosity sintered glass frit and washed with water and $Et_2O$ affording additional N-(3-(5-methyl-2-(methylsulfinyl)-7-oxopyrido[2,3-d]pyrimidin-8(7H)-yl)phenyl) acrylamide (5b; 4.59 g, 12.46 mmol, 85% yield) as a light yellow free-flowing solid after drying under vacuum. m/z (ESI, +ve ion) 369.1 (M+H)$^+$. $^1$H NMR (400 MHz, DMSO-$d_6$) δ ppm 10.33 (1H, s), 9.33 (1H, s), 7.69-7.76 (1H, m), 7.66 (1H, d, J=1.8 Hz), 7.43-7.52 (1H, m), 6.97-7.07 (1H, m), 6.81 (1H, d, J=1.4 Hz), 6.44 (1H, dd, J=16.9, 10.1 Hz), 6.25 (1H, dd, J=16.9, 1.9 Hz), 5.69-5.81 (1H, m), 2.71 (3H, s), 2.59 (3H, d, J=1.2 Hz).

Step 4. To a suspension of 2-methoxy-4-(4-methylpiperazin-1-yl)aniline (Green Chempharm; 3.45 g, 15.57 mmol) and N-(3-(5-methyl-2-(methylsulfinyl)-7-oxopyrido[2,3-d]pyrimidin-8(7H)-yl)phenyl)acrylamide (5b) (4.59 g, 12.46 mmol) in anhydrous tert-butanol (40 mL) and dioxane (5 mL) at RT was added DIEA (4.33 mL, 24.92 mmol). The mixture was heated at 100° C. for 40 h. The reaction mixture was concentrated under reduced pressure (rotary evaporator) to remove the volatiles and the resulting crude residue was suspended in $Et_2O$ and filtered. The greenish-brown amorphous solid was washed with $Et_2O$ (3×50 mL) and this removed most of the remaining aniline starting material. The crude material was dry-packed on silica gel and purified on a silica gel column (1-20% MeOH in DCM) affording N-(3-(2-((2-methoxy-4-(4-methylpiperazin-1-yl)phenyl)amino)-5-methyl-7-oxopyrido[2,3-d]pyrimidin-8(7H)-yl)phenyl)acrylamide (5) (2.03 g, 3.86 mmol, 31% yield) as a yellow amorphous solid. m/z (ESI, +ve ion) 526.2 (M+H)$^+$. $^1$H NMR (400 MHz, DMSO-$d_6$) δ ppm 10.33 (1H, s), 8.80 (1H, s), 8.09 (1H, s), 7.88 (1H, d, J=8.2 Hz), 7.56 (1H, J=1.9 Hz), 7.50 (1H, t, 1=8.1 Hz), 7.27 (1H, d, J=8.8 Hz), 6.97 (1H, dt, J=6.9, 1.0 Hz), 6.52 (1H, d, J=2.5 Hz), 6.37-6.48 (1H, m), 6.29-6.35 (1H, m), 6.19-6.29 (1H, m), 6.01 (1H, br. s.), 5.71-5.80 (1H, m), 3.78 (3H, s), 3.02 (4H, br. s.), 2.46 (3H, s), 2.43 (4H, t, J=4.9 Hz), 2.22 (3H, s).

Example 6

N-(3-(6-ethyl-2-((2-methoxy-4-(4-methyl-1-piperazinyl)phenyl)amino)-7-oxopyrido[2,3-d]pyrimidin-8(7H)-yl)phenyl)-2-propenamide

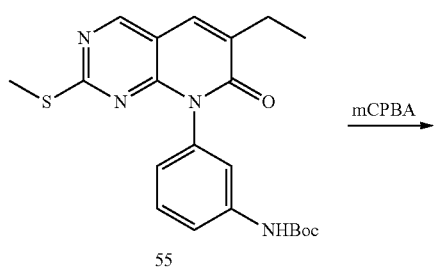

55 mCPBA →

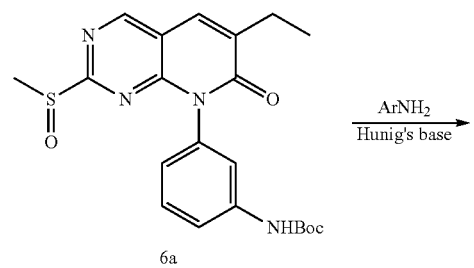

6a

ArNH$_2$ / Hunig's base →

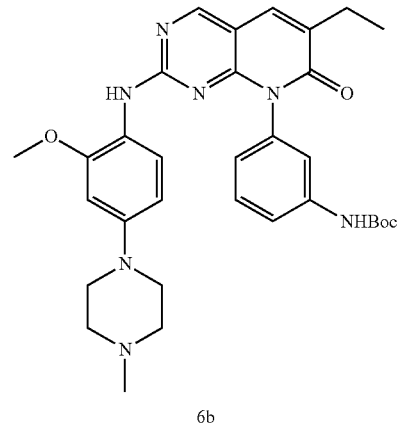

6b

1) TFA/DCM
2) 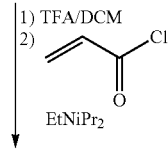

EtNiPr$_2$

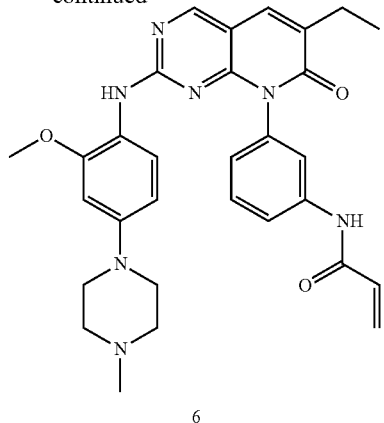

6

Step 1. At 0° C., a suspension of tert-butyl (3-(6-ethyl-2-(methylthio)-7-oxopyrido[2,3-d]pyrimidin-8(7H)-yl)phenyl)carbamate (55) (720 mg, 1.75 mmol) in DCM (15 mL) was treated with 3-chloroperoxybenzoic acid (70 wt. %, 460 mg, 1.87 mmol) in one portion and stirred at 0° C. for 1 h. The reaction mixture was diluted with DCM (15 mL), and treated with ice and a 10% solution of $Na_2CO_3$ (ca. 10 mL). The DCM layer was separated and the aqueous layer was extracted with an additional amount of DCM (2×50 mL), dried over sodium sulfate and concentrated to give tert-butyl (3-(6-ethyl-2-(methylsulfinyl)-7-oxopyrido[2,3-d]pyrimidin-8(7H)-yl)phenyl)carbamate (6a) (682 mg, 1.59 mmol, 91% yield) as a light yellow amorphous solid. m/z (ESI, +ve ion) 451.0 (M+Na)+. The crude material was used in the subsequent step without further purification.

Step 2. 2-Methoxy-4-(4-methylpiperazin-1-yl)aniline (Combi-Blocks Inc, San Diego, Calif., catalog #: SS-3744; 386 mg, 1.75 mmol), tert-butyl (3-(6-ethyl-2-(methylsulfinyl)-7-oxopyrido[2,3-d]pyrimidin-8(7H)-yl)phenyl)carbamate (6a) (680 mg, 1.59 mmol) were treated with tort-butanol (10 mL) and DIEA (0.69 mL, 3.97 mmol) and heated to 85° C. for 14 h in a 250 mL round-bottomed flask with a reflux condenser. The reaction mixture was concentrated under reduced pressure (rotary evaporator) and the crude solid was purified by chromatography on a silica gel column (1-20% MeOH in DCM) affording tert-butyl (3-(6-ethyl-2-((2-methoxy-4-(4-methylpiperazin-1-yl)phenyl)amino)-7-oxopyrido[2,3-d]pyrimidin-8(7H)-yl)phenyl)carbamate (6b; 717 mg, 1.23 mmol, 77% yield) as a light brown film. m/z (ESI, +ve ion) 585.9 (M+H)+.

Steps 3 and 4. tert-Butyl (3-(6-ethyl-2-((2-methoxy-4-(4-methylpiperazin-1-yl)phenyl)amino)-7-oxopyrido[2,3-d]pyrimidin-8(7H)-yl)phenyl)carbamate from above was treated with DCM (10 mL) and TFA (10 mL) and stirred at RT for 30 min. The reaction mixture was concentrated under reduced pressure (rotary evaporator) and purified on silica gel on an ISCO Combiflash RF (40 g Redisep column, 5-20% 2M $NH_3$/MeOH in DCM) affording 8-(3-aminophenyl)-6-ethyl-2-((2-methoxy-4-(4-methylpiperazin-1-yl)phenyl)amino)pyrido[2,3-d]pyrimidin-7(8H)-one (392 mg, 0.81 mmol, 51% yield) as a brown/yellow film. m/z (ESI, +ve ion) 486.0 (M+H)+. $^1$H NMR (400 MHz, MeOH-d4) δ ppm 8.67 (1H, s), 7.74 (1H, s), 7.68 (1H, d, J=8.6 Hz), 7.34 (1H, t, J=7.9 Hz), 6.92 (1H, dd, 1=8.1, 1.5 Hz), 6.61-6.67 (2H, m), 6.58 (1H, dd, J=7.6, 1.0 Hz), 6.26 (1H, d, J=7.2 Hz), 5.51 (2H, s), 3.90 (3H, s), 3.30 (4H, br. s), 3.18 (4H, br. s), 2.79 (3H, s), 2.63 (2H, q, J=7.4 Hz), 1.28 (3H, t, J=7.5 Hz). 8-(3-Aminophenyl)-6-ethyl-2-((2-methoxy-4-(4-methylpiperazin-1-yl)phenyl)amino)pyrido[2,3-d]pyrimidin-7(8H)-one (390 mg, 0.80 mmol) in a mixture of DCM (7 mL) and THF (7 mL) at 0° C. was treated with DIEA (0.35 mL, 2.01 mmol) followed by the slow dropwise addition of acryloyl chloride (0.078 mL, 0.964 mmol) over 5 min. The solution was stirred 0° C. for 15 min. LC-MS indicated ca. a 79:11 ratio of desired product m/z (ESI, +ve ion) 539.9 (M+H)+ and starting material m/z (ESI, +ve ion) 486.0 (M+H)+. 2 additional drops of acryloyl chloride were added and the mixture was stirred an additional 2 h at 0° C. The reaction mixture was treated with silica gel and concentrated on the rotovap to dryness. The material was purified on an ISCO Combiflash RF (40 g Redisep column, using a gradient of 0-20% MeOH in DCM) affording enriched product as a yellow powdery solid. It was repurified on a Gilson preparatory HPLC (Gemini Phenomenex; 30×150 mm, 5 u, 10-95% 0.1% TFA/$CH_3CN$ in 0.1% TFA/water), concentrated on the rotovap to remove the $CH_3CN$ and treated with 1N NaOH and extracted with $CHCl_3$ (3×50 mL), dried over $Na_2SO_4$, filtered and concentrated affording N-(3-(6-ethyl-2-((2-methoxy-4-(4-methylpiperazin-1-yl)phenyl)amino)-7-oxopyrido[2,3-d]pyrimidin-8(7H)-yl)phenyl)acrylamide (6) (154 mg, 0.29 mmol, 35% yield) as a bright yellow solid. m/z (ESI, +ve ion) 540.0 (M+H)+. $^1$H NMR (400 MHz, MeOH-d4) δ ppm 8.68 (1H, s), 8.04 (1H, d, J=7.2 Hz), 7.77 (1H, s), 7.58-7.65 (2H, m), 7.49 (1H, d, J=8.4 Hz), 7.08 (1H, d, J=8.0 Hz), 6.58 (1H, d, J=2.5 Hz), 6.34-6.51 (2H, m), 6.14 (1H, d, J=7.0 Hz), 5.80 (1H, dd, J=9.6, 2.2 Hz), 3.88 (3H, s), 3.13 (4H, d, J=3.9 Hz), 2.58-2.69 (6H, m), 2.38 (3H, s), 1.30 (3H, t, J=7.4 Hz).

Example 7

N-(3-(2-((2-methoxy-4-(4-morpholinyl)phenyl)amino)-5-methyl-7-oxopyrido[2,3-d]pyrimidin-8(7H)-yl)phenyl)-2-propenamide

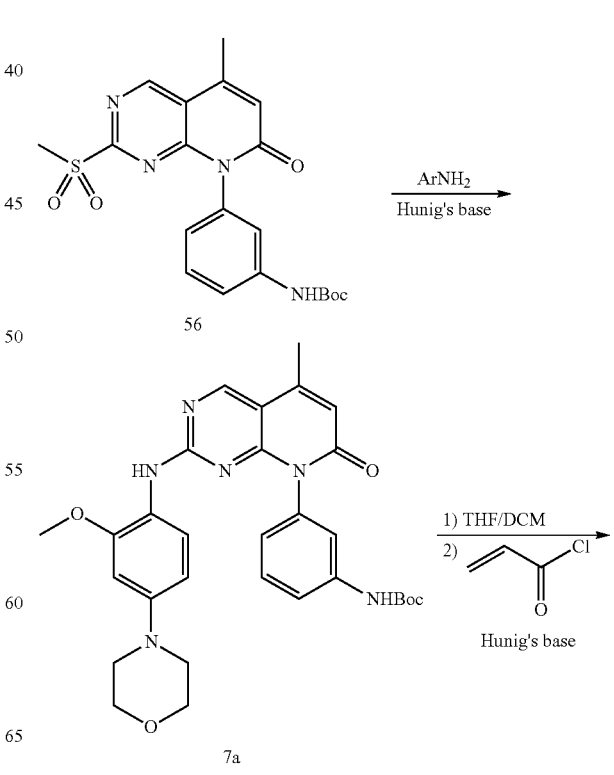

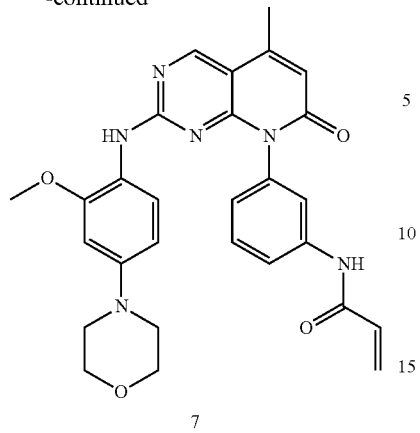

7

In a 5 mL glass microwave tube was weighed tert-butyl (3-(5-methyl-2-(methylsulfonyl)-7-oxopyrido[2,3-d]pyrimidin-8(7H)-yl)phenyl)carbamate (56) (150 mg, 0.35 mmol), 2-methoxy-4-morpholinoaniline (Matrix Scientific, Columbia, S.C., 54 mg, 0.26 mmol) followed by purging with argon. The solids were then treated with tert-butanol (2.0 mL) and DIEA (0.11 mL, 0.65 mmol). The tube was sealed and heated to 85° C. for 20 h. The crude reaction mixture was purified on silica gel on an ISCO Combiflash RF (40 g Thomson SingleStep column, using a gradient of 0-15% MeOH in DCM) affording tert-butyl (3-(5-methyl-2-(methylsulfonyl)-7-oxopyrido[2,3-d]pyrimidin-8(7H)-yl)phenyl)carbamate (7a; 150 mg, 0.35 mmol) as a brownish film. m/z (ESI, +ve ion) 560.0 (M+H)⁺.

N-(3-(2-((2-Methoxy-4-(4-morpholinyl)phenyl)amino)-5-methyl-7-oxopyrido[2,3-d]pyrimidin-8(7H)-yl)phenyl)-2-propenamide (7) (11 mg, 9% overall yield for 2 steps) as a yellow solid was prepared according to the procedures described for Example 6, using (3-(5-methyl-2-(methylsulfonyl)-7-oxopyrido[2,3-d]pyrimidin-8(7H)-yl)phenyl)carbamate (7a; 150 mg, 0.35 mmol) as the starting material. m/z (ESI, +ve ion) 514.0 (M+H)⁺. ¹H NMR (400 MHz, MeOH-d4) δ ppm 9.01 (1H, s), 7.66 (1H, d, J=7.6 Hz), 7.47-7.53 (1H, m), 7.33 (1H, t, J=8.0 Hz), 6.77-6.85 (2H, m), 6.56 (1H, s), 6.40-6.47 (3H, m), 6.36 (1H, dd, J=8.7, 2.4 Hz), 5.82 (1H, dd, J=9.6, 2.2 Hz), 3.82-3.92 (4H, m), 3.61 (3H, s), 3.05-3.14 (4H, m), 2.62 (3H, s).

Example 8

N-(3-(2-((4-methoxy-6-(4-methyl-1-piperazinyl)-3-pyridinyl)amino)-7-oxopyrido[2,3-d]pyrimidin-8(7H)-yl)phenyl)-2-propenamide

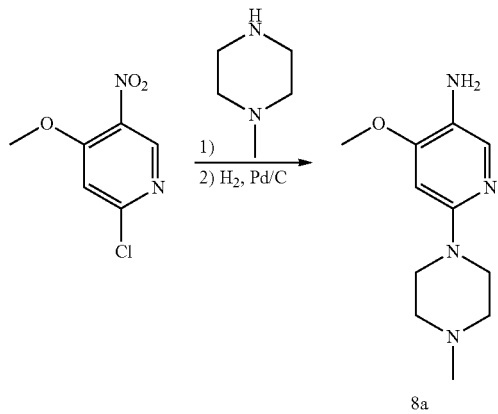

8a

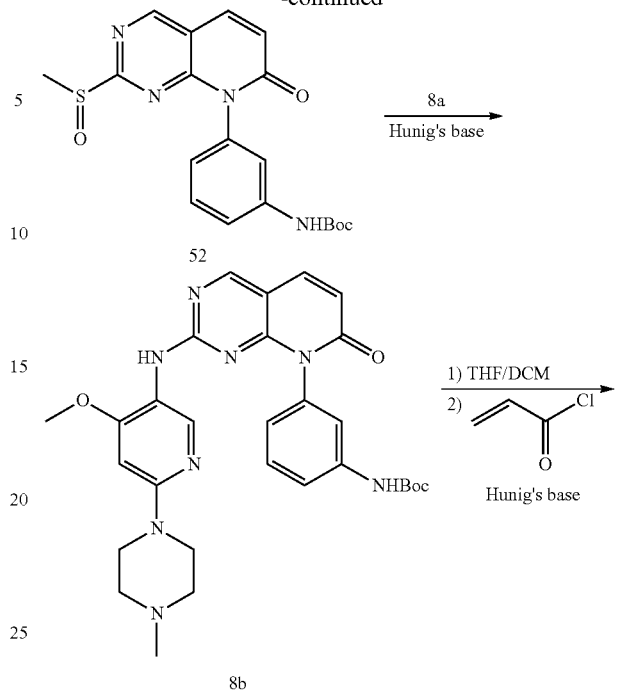

Preparation of 4-methoxy-6-(4-methylpiperazin-1-yl)pyridin-3-amine (8a). 2-Chloro-4-methoxy-5-nitropyridine (Frontier Scientific, Newark, Del.; 1.02 g, 5.40 mmol) and K₂CO₃ (895 mg, 6.48 mmol) were purged with argon, treated with DMF (10 mL) followed by 1-methylpiperazine (0.66 mL, 5.94 mmol). The reaction mixture was then heated to 60° C. for 3 h. The reaction mixture was cooled to RT and treated with water, extracted with EtOAc (2×100 mL), washed with brine (2×25 mL) and dried over MgSO₄, filtered and concentrated affording crude 1-(4-methoxy-5-nitropyridin-2-yl)-4-methylpiperazine (1.36 g, 5.39 mmol, 99% yield). m/z (ESI, +ve ion) 252.9 (M+H)⁺. ¹H NMR (400 MHz, CDCl₃) δ ppm 8.88 (1H, s), 5.97 (1H, s), 3.97 (3H, s), 3.70-3.78 (4H, m), 2.47-2.55 (4H, m), 2.36 (3H, s). Pd/C (10 wt. %, 586 mg, 0.55 mmol) and 1-(4-methoxy-5-nitropyridin-2-yl)-4-methylpiperazine (1.36 g, 5.39 mmol) were treated with EtOH (20 mL) and EtOAc (20 mL) and stirred at RT overnight (18 h) under an atmosphere of hydrogen (balloon). The reaction mixture was filtered through a pad of Celite, washed with MeOH, and concentrated to dryness affording 4-methoxy-6-(4-methylpiperazin-1-yl)pyridin-3-amine (8a) (1.22 g, 5.77 mmol, 99% yield) as a purple viscous oil. m/z (ESI, +ve ion) 223.1

(M+H)+. 1H NMR (400 MHz, CDCl3) δ ppm 7.67 (1H, s), 6.17 (1H, s), 3.87 (3H, s), 3.37-3.45 (4H, m), 3.32 (2H, br. s.), 2.51-2.60 (4H, m), 2.36 (3H, s).

Preparation of tert-butyl (3-(2-((4-methoxy-6-(4-methylpiperazin-1-yl)pyridin-3-yl)amino)-7-oxopyrido[2,3-d]pyrimidin-8(7H)-yl)phenyl)carbamate (8b). 4-Methoxy-6-(4-methylpiperazin-1-yl)pyridin-3-amine (8a; 1.22 g, 5.49 mmol), tert-butyl (3-(2-(methylsulfinyl)-7-oxopyrido[2,3-d]pyrimidin-8(7H)-yl)phenyl)carbamate (52; 1.40 g, 3.50 mmol) were treated with tert-butanol (20 mL) and DIEA (1.53 mL, 8.74 mmol) and heated to 85° C. overnight (20 h) in a 250 mL round-bottomed flask with a reflux condenser. The reaction mixture was concentrated on the rotovap and the crude solid was suspended in Et2O and filtered affording the crude tert-butyl (3-(2(4-methoxy-6-(4-methylpiperazin-1-yl)pyridin-3-yl)amino)-7-oxopyrido[2,3-d]pyrimidin-8 (7H)-yl)phenyl)carbamate (8b; 1.50 g, 2.69 mmol, 77% yield) as a brownish-yellow amorphous solid. m/z (ESI, +ve ion) 559.0 (M+H)+. 1H NMR (400 MHz, DMSO-d6) δ ppm 9.48 (1H, br. s.), 8.65 (1H, br. s.), 8.54 (1H, s), 7.86 (1H, d, J=9.4 Hz), 7.82 (1H, s), 7.43 (1H, d, J=8.0 Hz), 7.37 (2H, br. s.), 6.81 (1H, br. s.), 6.38 (1H, d, J=9.4 Hz), 6.29 (1H, br. s.), 3.73 (3H, s), 3.45 (4H, br. s.), 2.40 (4H, br. s.), 2.24 (3H, s), 1.47 (9H, s).

N-(3-(2-((4-Methoxy-6-(4-methyl-1-piperazinyl)-3-pyridinyl)amino)-7-oxopyrido[2,3-d]pyrimidin-8(7H)-yl)phenyl)-2-propenamide (8) (14% overall yield for 2 steps) as a yellow crystalline solid was prepared according to the procedures described for Example 6, using tert-butyl (3-(2-((4-methoxy-6-(4-methylpiperazin-1-yl)pyridin-3-yl)amino)-7-oxopyrido[2,3-d]pyrimidin-8(7H)-yl)phenyl)carbamate (8b) as the starting material. m/z (ESI, +ve ion) 512.9 (M+H)+. 1H NMR (400 MHz, DMSO-d6) δ ppm 10.26 (1H, br. s.), 8.67 (1H, br. s.), 8.55 (1H, s), 7.87 (1H, d, J=9.4 Hz), 7.82 (1H, s), 7.70 (1H, d, J=7.8 Hz), 7.57 (1H, br. s.), 7.34-7.48 (1H, m), 6.94 (1H, br. s.), 6.37-6.49 (2H, m), 6.20-6.32 (2H, m), 5.72-5.80 (1H, m), 3.72 (3H, s), 3.43 (4H, br. s.), 2.38 (4H, t, J=4.9 Hz), 2.22 (3H, s).

Example 9

(2E)-4-(dimethylamino)-N-(3-(2-((2-methoxy-4-(4-methyl-1-piperazinyl)phenyl)amino)-7-oxopyrido[2,3-d]pyrimidin-8(7H)-yl)phenyl)-2-butenamide

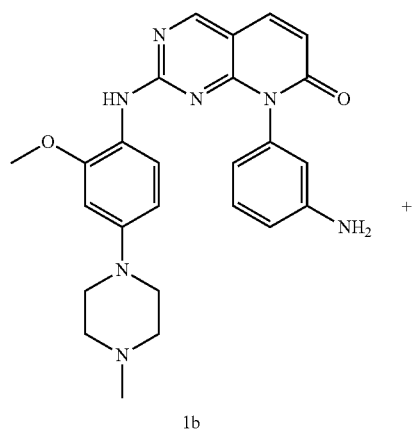

1b

+

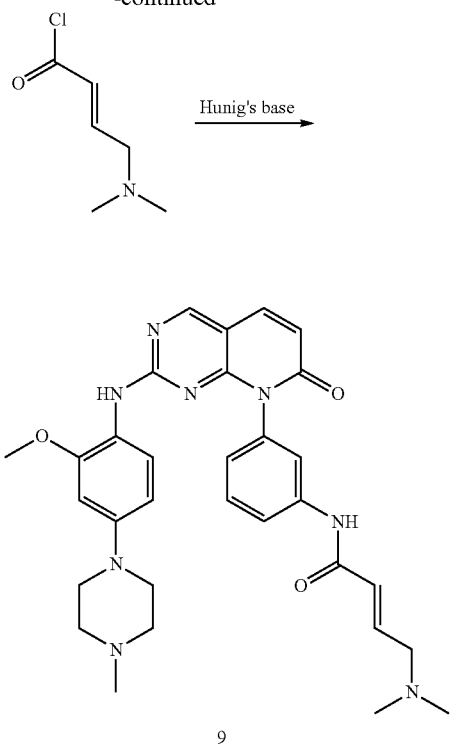

9

8-(3-Aminophenyl)-2-((2-methoxy-4-(4-methylpiperazin-1-yl)phenyl)amino)pyrido[2,3-d]pyrimidin-7(8H)-one (1b, 255 mg, 0.56 mmol) was added in one portion as a solid to a suspension of (E)-4-(dimethylamino)but-2-enoyl chloride hydrochloride (283 mg, 1.538 mmol) in THF (10 mL) at 0° C. The resulting orange suspension was treated with DIEA (0.39 mL, 2.23 mmol) slowly and stirred for 30 min at 0° C. The reaction mixture was removed from the ice bath and stirred at RT for 30 min. The reaction mixture was treated with silica gel, concentrated on the rotovap and purified on an ISCO Combiflash RF (40 g Redisep column, using a gradient of 0-20% MeOH in DCM) affording enriched product as a yellow solid. This sample was repurified on the Gilson preparatory HPLC (Gemini Phenomenex; 30×150 mm, 5 u, 10-95% 0.1% TFA/CH3CN in 0.1% TFA/water). The product containing fractions were concentrated in the genevac overnight and the resulting orange solid was then passed through a Silicycle SPE-R66030B-20× SiliaSep OT, 5 g/25 mL carbonate column using 10% MeOH/DCM then concentrated and dried again in the genevac for 3 h affording (E)-4-(dimethylamino)-N-(3-(2-((2-methoxy-4-(4-methylpiperazin-1-yl)phenyl)amino)-7-oxopyrido[2,3-d]pyrimidin-8(7H)-yl)phenyl)but-2-enamide (35 mg, 0.062 mmol, 11% yield) as an orange solid. m/z (ESI, +ve ion) 569.0 (M+H)+. 1H NMR (400 MHz, DMSO-d6) δ ppm 10.25 (1H, s), 8.74 (1H, s), 8.14 (1H, s), 7.90 (1H, d, J=9.4 Hz), 7.79-7.88 (1H, m), 7.59 (1H, s), 7.49 (1H, t, J=8.0 Hz), 7.27 (1H, d, J=9.0 Hz), 6.98 (1H, d, J=8.6 Hz), 6.73 (1H, dt, J=15.4, 5.8 Hz), 6.51 (1H, d, J=2.3 Hz), 6.44 (1H, Hz), 6.27 (1H, d, J=15.3 Hz), 6.02 (1H, br. s.), 3.77 (3H, s), 3.04 (6H, d, J=5.7 Hz), 2.36-2.46 (4H, m), 2.22 (3H, s), 2.16 (6H, s).

Example 10

N-(4-fluoro-3-(2-((2-methoxy-4-(4-methyl-1-piperazinyl)phenyl)amino)-7-oxopyrido[2,3]pyrimidin-8(7H)-yl)phenyl)-2-propenamide

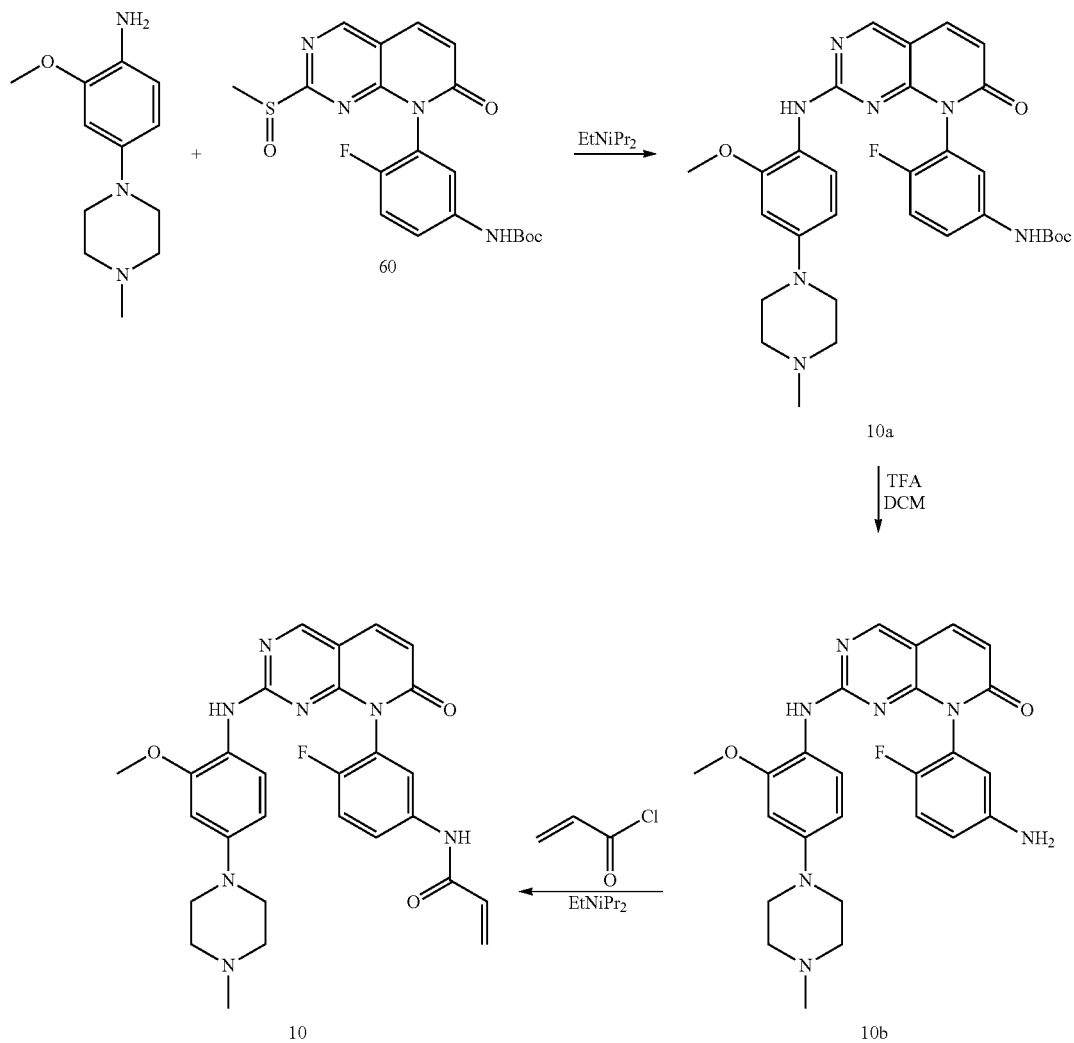

The title compound was prepared according to the procedures described for Example 1, starting from tert-butyl (4-fluoro-3-(2-(methylsulfinyl)-7-oxopyrido[2,3-d]pyrimidin-8(7H)-yl)phenyl)carbamate (60).

tert-Butyl (4-fluoro-3-(2-((2-methoxy-4-(4-methylpiperazin-1-yl)phenyl)amino)-7-oxopyrido[2,3-d]pyrimidin-8(7H)-yl)phenyl)carbamate (10a): m/z (ESI, +ve ion) 575.9 (M+H)+. $^{19}$F NMR (376 MHz, CDCl$_3$) δ ppm-127.13 (1F, s).

8-(5-Amino-2-fluorophenyl)-2-((2-methoxy-4-(4-methylpiperazin-1-yl)phenyl)amino)pyrido[2,3-d]pyrimidin-7(8H)-one (10b): m/z (ESI, +ve ion) 476.0 (M+H)+. $^1$H NMR (400 MHz, DMSO-d$_6$) δ ppm 8.73 (1H, s), 8.25 (1H, br. s.), 7.90 (1H, d, J=9.4 Hz), 7.39 (1H, d, J=8.6 Hz), 7.08 (1H, 1, 0.1=9.3 Hz), 6.67-6.73 (1H, m), 6.56 (1H, d, J=2.3 Hz), 6.50 (1H, dd, J=6.5, 2.7 Hz), 6.42 (1H, d, J=9.4 Hz), 6.20 (1H, br. s.), 5.14 (2H, s), 3.75-3.83 (3H, m), 3.12 (4H, br. s.), 2.58 (3H, br. s.), 2.21-2.40 (4H, m) $^{19}$F NMR (376 MHz, DMSO-d$_6$) δ ppm-139.03 (1F, s).

N-(4-Fluoro-3-(2-((2-methoxy-4-(4-methylpiperazin-1-yl)phenyl)amino)-7-oxopyrido[2,3-d]pyrimidin-8(7H)-yl)phenyl)acrylamide (10). m/z (ESI, +ve ion) 529.9 (M+H)+. $^1$H NMR (400 MHz, DMSO-d$_6$) δ ppm 10.42 (1H, s), 8.78 (1H, br. s.), 8.35 (1H, br. s.), 7.95 (1H, d, J=9.4 Hz), 7.88 (1H, br. s.), 7.74 (1H, dd, J=6.7, 2.5 Hz), 7.44 (1H, t, J=9.3 Hz), 7.24 (1H, d, J=8.8 Hz), 6.50-6.56 (1H, m), 6.38-6.50 (2H, m), 6.22-6.31 (1H, m), 6.03 (1H, br. s.), 5.74-5.83 (1H, m), 3.77 (3H, s), 3.05 (4H, br. s.), 2.44 (4H, t, J=4.8 Hz), 2.23 (3H, s). $^{19}$F NMR (376 MHz, DMSO-d$_6$) δ ppm-127.45 (1F, s).

Example 11

N-(3-(2-((4-((1-(2-fluoroethyl)-3-azetidinyl)amino)-2-methoxyphenyl)amino)-7-oxopyrido[2,3-d]pyrimidin-8(7H)-yl)phenyl)-2-propenamide

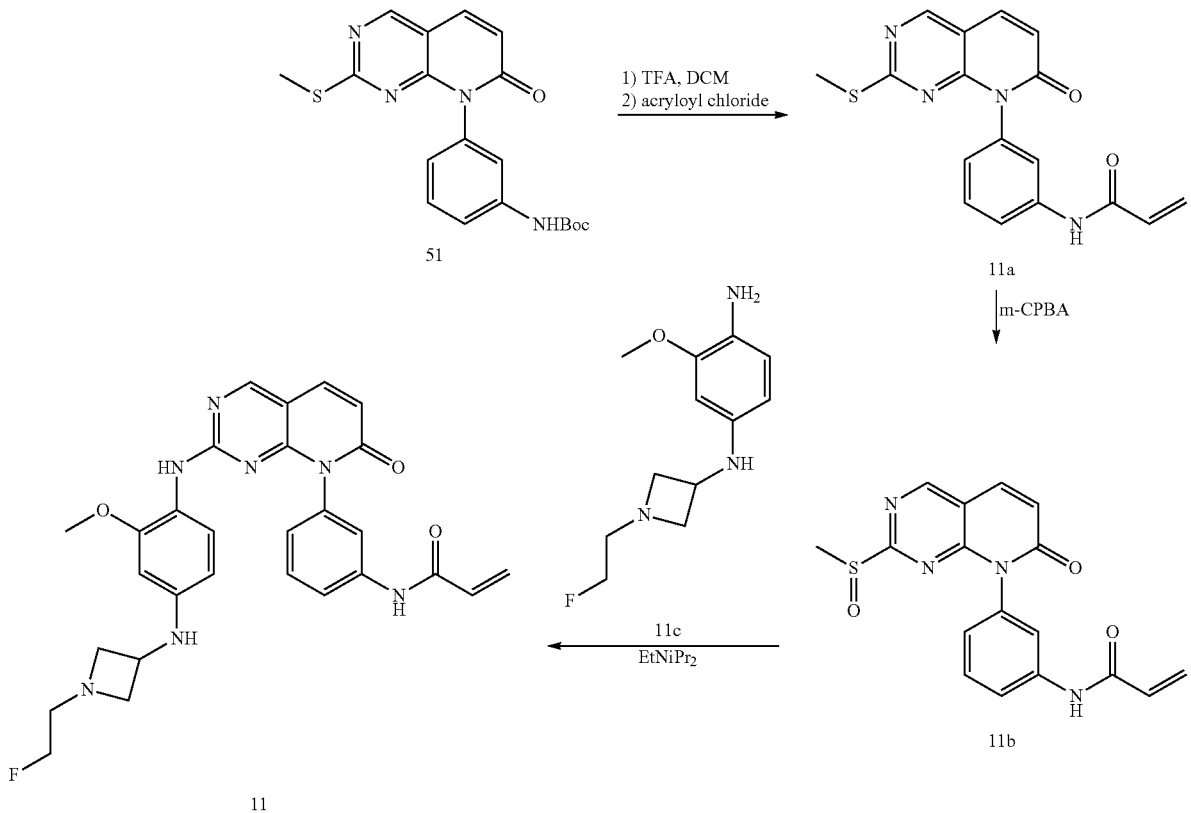

Preparation of N-(3-(2-(methylthio)-7-oxopyrido[2,3-d]pyrimidin-8(7H)-yl)phenyl)acrylamide (11a). To a suspension of tert-butyl (3-(2-(methylthio)-7-oxopyrido[2,3-d]pyrimidin-8(7H)-yl)phenyl)carbamate (51) (651 mg, 1.69 mmol) in 10 mL of DCM at RT was added 3 mL of TFA. The resulting homogeneous solution was stirred at RT for 1 h. It was concentrated under reduced pressure. The residue was in dissolved in 20 mL of DCM and cooled with an ice bath, then treated with DEIA (1.47 mL, 8.47 mmol) followed by acryloyl chloride (0.16 mL, 2.03 mmol). After 20 min at 0° C., additional acryloyl chloride (80 µL) was added in. The resulting mixture was stirred for 5 min, then quenched with 0.5 N NaOH (10 mL). The layers were separated and the water layer was extracted with 50 mL of DCM. The combined DCM extracts were washed with 2×5 mL of brine, dried over Na$_2$SO$_4$ and concentrated. The residue was stirred in 25 mL of EtOAc. The insoluble solid was filtered and dried to give 310 mg of N-(3-(2-(methylthio)-7-oxopyrido[2,3-d]pyrimidin-8(7H)-yl)phenyl)acrylamide (11a). The filtrate was concentrated and purified on a silica gel column (35-100% EtOAc in hexanes) to give 140 mg of N-(3-(2-(methylthio)-7-oxopyrido[2,3-d]pyrimidin-8(7H)-yl)phenyl)acrylamide (11a). m/z (ESI, +ve ion) 338.9 (M+H)$^+$. $^1$H NMR (400 MHz, DMSO-d$_6$) δ ppm 10.40 (1H, s), 8.95 (1H, s), 8.05 (1H, d, J=9.6 Hz), 7.68 (2H, m), 7.49 (1H, t, J=7.8 Hz), 7.04 (1H, d, J=8.2 Hz), 6.72 (1H, d, J=9.6 Hz), 6.46 (1H, dd, J=17.0, 10.2 Hz), 6.26 (1H, d, J=16.8 Hz), 5.78 (1H, d, J=9.6 Hz), 2.20 (3H, s).

Preparation of N-(3-(2-(methylsulfinyl)-7-oxopyrido[2,3-d]pyrimidin-8(7H)-yl)phenyl)acrylamide (11b). At 0° C., to a suspension of N-(3-(2-(methylthio)-7-oxopyrido[2,3-d]pyrimidin-8(7H)-yl)phenyl)acrylamide (11a) (450 mg, 1.33 mmol) in 25 mL of DCM was added MCPBA (319 mg of 77% max. from Aldrich, 1.42 mmol). After the reaction mixture was stirred at 0° C. for 35 min, it was diluted with 100 mL of DCM, washed with 20 mL of ice cold sat Na$_2$CO$_3$ solution. The DCM layer was dried over Na$_2$SO$_4$ and concentrated to give N-(3-(2-(methylsulfinyl)-7-oxopyrido[2,3-d]pyrimidin-8(7H)-yl)phenyl)acrylamide (11b) (398 mg, 84% yield) as an off white crystalline solid. The crude material was used in next step without further purification. m/z (ESI, +ve ion) 355.0 (M+H)$^+$. $^1$H NMR (400 MHz, DMSO-d6) δ ppm 10.36 (1H, s), 9.30 (1H, s), 8.20 (1H, d, J=9.6 Hz), 7.76 (1H, m), 7.69 (1H, m), 7.51 (1H, t, J=8.0 Hz), 7.06 (1H, d, J=7.6 Hz), 6.94 (1H, m), 6.45 (1H, dd, J=16.9, 10.1 Hz), 6.26 (1H, d, J=16.8 Hz), 5.79 (1H, m), 2.72 (3H, s)

N1-(1-(2-Fluoroethyl)azetidin-3-yl)-3-methoxybenzene-1,4-diamine (11c) was prepared according to the procedures described in WO 2012064706 A1 (April, 2012), Avila Therapeutics, Inc.

Preparation of N-(3-(2-((4-((1-(2-fluoroethyl)azetidin-3-yl)amino)-2-methoxyphenyl)amino)-7-oxopyrido[2,3-d]pyrimidin-8(7H)-yl)phenyl)acrylamide (11). To a suspension of N1-(1-(2-fluoroethyl)azetidin-3-yl)-3-methoxybenzene-1,4- diamine (11c) (135 mg, 0.56 mmol) and N-(3-(2-(methylsulfinyl)-7-oxopyrido[2,3-d]pyrimidin-8(7H)-yl)phenyl)acrylamide (11b) (230 ing, 0.65 mmol) in 1 mL of dioxane and 1 mL of tBuOH at RT was added DIEA (0.29 mL, 1.69 mmol). The mixture was heated in an oil bath at 85° C. for 3 h. It was concentrated under reduced pressure. The residue was purified on a silica gel column (5% MeOH in DCM followed by 2-6% of 2 M NH₃ in MeOH in DCM) to give a material that was about 95% pure. The material was dissolved in 10 mL of DMSO and purified on a reverse phase HPLC, using a gradient of 10-90% of (0.1% TFA in CH₃CN) in (0.1% TFA in water). Desired fractions were collected, lyophilized and the powdery residue was dissolved in 2 mL of MeOH, passed through a Silicycle (5 G) carbonate cartridge, rinsed with MeOH (20 mL). The fractions were collected and concentrated to give the title compound (95 mg, 31% yield) as a brown crystalline solid. m/z (ESI, +ve ion) 530.0 (M+H)⁺. ¹H NMR (400 MHz, DMSO-d6) δ ppm 10.40 (1H, br.), 8.73 (1H, br.), 8.10 (1H, br.), 7.90 (1H, d, J=9.4 Hz), 7.83 (1H, br.), 7.64 (1H, s), 7.51 (1H, t, J=8.0 Hz), 7.15 (1H, br.), 7.02 (1H, d, J=8.6 Hz), 6.44 (2H, m), 6.29 (1H, m), 6.16 (1H, d, J=2.0 Hz), 5.86 (1H, br.), 5.78 (1H, m), 5.57 (1H, br.), 4.49 (1H, t, J=4.8 Hz), 4.37 (1H, t, J=4.9 Hz), 3.90 (1H, br.), 3.72 (3H, s), 3.70 (2H, m), 2.83 (2H, m), 2.74 (1H, 1, J=4.8 Hz), 2.67 (1H, t, J=4.8 Hz).

Example 12

2-chloro-N-(3-(2-((2-methoxy-4-(4-methyl-1-piperazinyl)phenyl)amino)-7-oxopyrido[2,3-d]pyrimidin-8(7H)-yl)phenyl)acetamide

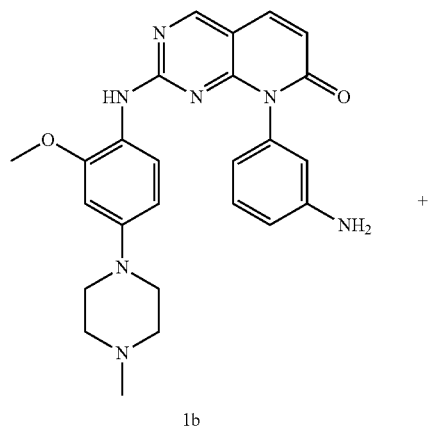

1b

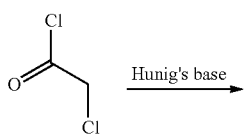

Hunig's base →

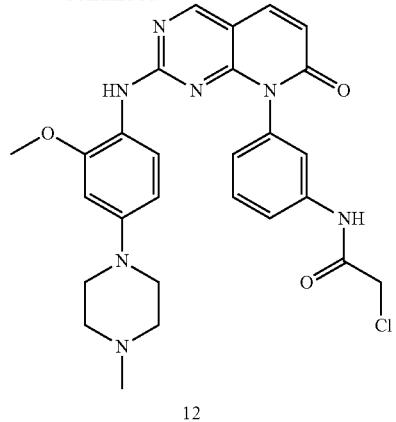

12

8-(3-Aminophenyl)-24(2-methoxy-4-(4-methylpiperazin-1-yl)phenyl)amino)pyrido[2,3-d]pyrimidin-7(8H)-one (1b, 131 mg, 0.29 mmol) in DCM (5 mL) at 0° C. was treated with DIEA (0.13 mL, 0.72 mmol) and cooled in an ice bath at 0° C. The solution was then treated with 2-chloroacetyl chloride (Sigma Aldrich; 0.027 mL, 0.344 mmol) slowly dropwise over 10 min and stirred at 0° C. for 30 min. LC-MS indicated only trace amounts of the desired product. The reaction mixture was sonicated for 10 min to help dissolve the substrate and another 2 drops of 2-chloroacetyl chloride was added. After 30 min, LC-MS indicated 74% conversion to the desired product m/z (ESI, +ve ion) 533.9 (M+H)⁺ along with unreacted starting material. 2 more drops of 2-chloroacetyl chloride was added and the solution stirred for another 75 min resulting in clean conversion to the desired product. The reaction mixture was concentrated, treated with DMSO (8 mL) and purified on a Gilson preparatory HPLC (Gemini Phenomenex; 30×150 mm, 5µ, 10-95% 0.1% TFA/CH₃CN in 0.1% TFA/water). The product containing fractions were concentrated under reduced pressure (rotary evaporator) and the resulting aqueous solution treated with a 10% aqueous solution of Na₂CO₃ and extracted with DCM (4×30 mL), dried over sodium sulfate and dried under vacuum overnight affording 2-chloro-N-(3-(2-((2-methoxy-4-(4-methylpiperazin-1-yl)phenyl)amino)-7-oxopyrido[2,3-d]pyrimidin-8(7H)-yl)phenyl)acetamide (53.4 mg, 0.100 mmol, 35% yield) as a yellow solid. m/z (ESI, +ve ion) 533.9 (M+H)⁺. ¹H NMR (400 MHz, DMSO-d₆) δ ppm 10.50 (1H, s), 8.75 (1H, s), 8.17 (1H, s), 7.91 (1H, d, J=9.4 Hz), 7.75 (1H, d, J=8.2 Hz), 7.49-7.57 (2H, m), 7.25 (1H, d, J=9.0 Hz), 7.04 (1H, d, J=7.8 Hz), 6.53 (1H, d, J=2.2 Hz), 6.44 (1H, d, J=9.4 Hz), 6.04 (1H, br. s.), 4.25 (2H, s), 3.78 (3H, s), 3.06 (4H, br. s.), 2.40-2.48 (4H, m), 2.23 (3H, s).

Example 13

3-(dimethylamino)-N-(3-(2-((2-methoxy-4-(4-methylpiperazin-1-yl)phenyl)amino)-7-oxopyrido[2,3-d]pyrimidin-8(7H)-yl)phenyl)propanamide

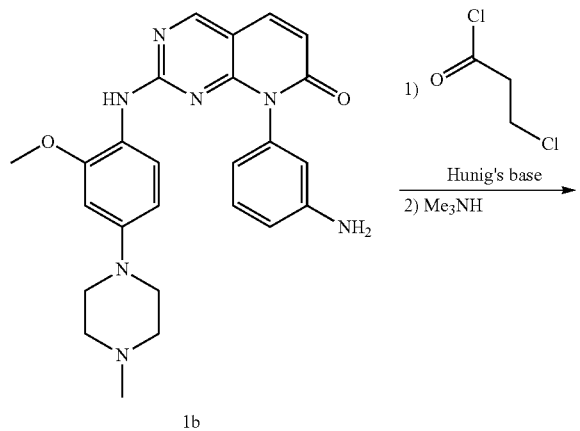

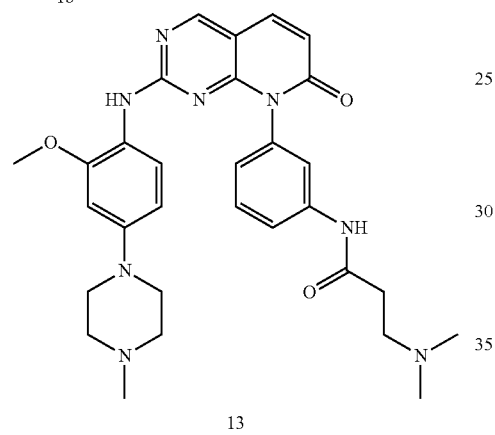

13

Step 1. 8-(3-Aminophenyl)-2-((2-methoxy-4-(4-methylpiperazin-1-yl)phenyl)amino)pyrido[2,3-d]pyrimidin-7(8H)-one (1b; 200 mg, 0.44 mmol) in DCM (5 mL) at 0° C. was treated with DIEA (0.19 mL, 1.09 mmol) and cooled in an ice bath at 0° C. The solution was then treated with 3-chloropropionyl chloride (Sigma Aldrich, St. Louis, Mo.; 0.042 mL, 0.44 mmol) dropwise over 10 min and stirred at 0° C. for 30 min then stirred at RT for 2 h. 3 more drops of 3-chloropropionyl chloride was added and the reaction stirred at RT overnight. The reaction mixture was then concentrated, treated with DMSO (8 mL) and purified on a Gilson preparatory HPLC (Gemini Phenomenex; 30×150 mm, 5μ, 10-95% 0.1% TFA/CH$_3$CN in 0.1% TFA/water). The product containing fractions were concentrated under reduced pressure (rotary evaporator) and the resulting aqueous solution treated with a 10% solution of Na$_2$CO$_3$ and extracted with DCM (4×30 mL), dried over Na$_2$SO$_4$ and concentrated under vacuum overnight affording 3-chloro-N-(3-(2-((2-methoxy-4-(4-methylpiperazin-1-yl)phenyl)amino)-7-oxopyrido[2,3-d]pyrimidin-8(7H)-yl)phenyl)propanamide (57 mg, 0.10 mmol, 23% yield) as a yellow solid. m/z (ESI, +ve ion) 548.0 (M+H)$^+$ in about 65% purity with the mass balance corresponding to the acrylamide. The material was used in the subsequent step without further purification.

Step 2. 3-Chloro-N-(3-(2-((2-methoxy-4-(4-methylpiperazin-1-yl)phenyl)amino)-7-oxopyrido[2,3-d]pyrimidin-8(7H)-yl)phenyl)propanamide (57 mg, 0.086 mmol) was treated with dimethylamine (2.0 M in THF, 2.00 mL, 4.00 mmol) and stirred at 50° C. for 90 min then stirred at RT for 72 h. The reaction mixture was then purified by chromatography on silica gel on an ISCO Combiflash RF (24 g Redisep HP (Gold), using a gradient of 0-20% 2M NH$_3$/MeOH in DCM) affording 3-(dimethylamino)-N-(3-(2-((2-methoxy-4-(4-methylpiperazin-1-yl)phenyl)amino)-7-oxopyrido[2,3-d]pyrimidin-8(7H)-yl)phenyl)propanamide (44.6 mg, 0.066 mmol, 76% yield) as a yellow-orange amorphous foam. m/z (ESI, +ve ion) 557.0 (M+H)$^+$. $^1$H NMR (400 MHz, MeOH-d4) δ ppm 8.71 (1H, s), 7.92 (1H, d, J=9.4 Hz), 7.57-7.61 (1H, m), 7.56 (1H, s), 7.44 (1H, d, J=7.8 Hz), 7.06 (1H, d, J=8.0 Hz), 6.58 (1H, d, J=2.5 Hz), 6.53 (1H, d, J=9.4 Hz): 6.12 (1H, br. s.), 3.88 (3H, s), 3.10-3.19 (4H, m), 2.77 (2H, q, J=6.7 Hz), 2.63-2.68 (4H, m), 2.57-2.62 (2H, m), 2.39 (3H, s), 2.33 (6H, s).

Example 14

N-(3-(2-((4-((1-acetylazetidin-3-yl)amino)-2-methoxyphenyl)amino)-7-oxopyrido[2,3-d]pyrimidin-8(7H)-yl)phenyl)acrylamide

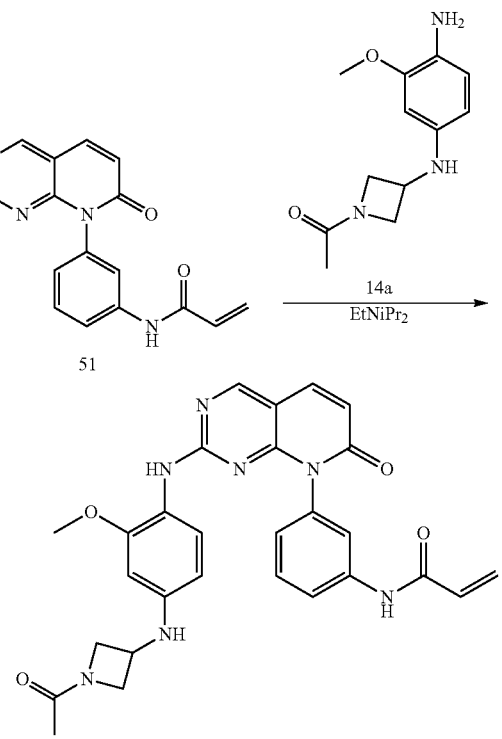

To a suspension of 1-(3-((4-amino-3-methoxyphenyl)amino)azetidin-1-yl)ethanone (14a, prepared according to the procedures described in WO 2012064706 A1 (April, 2012), Avila Therapeutics, Inc.) (120 mg, 0.51 mmol) and N-(3-(2-(methylsulfinyl)-7-oxopyrido[2,3-d]pyrimidin-8(7H)-yl)phenyl)acrylamide (51) (150 mg, 0.42 mmol) in 1 mL of dioxane and 1 mL of tBuOH at RT was added DIEA (0.22 mL, 1.27 mmol). The mixture was heated in an oil bath at 85° C. for 1 h. NMP (0.5 mL) was added to the reaction mixture and heating was continued for 3 h. It was concentrated under reduced pressure. The residue was purified on a silica gel column (5% MeOH in DCM followed by 2-6% of 2

M NH₃ in MeOH in DCM) to give a material that was about 90% pure. This material was dissolved in 10 mL of DMSO and purified on a reverse phase HPLC, using a gradient of 10-90% of (0.1% TFA in CH₃CN) in (0.1% TFA in water). Desired fractions were collected, lyophilized and the powdery residue was dissolved in MeOH, passed through a Silicycle (5 G) carbonate cartridge, rinsed with MeOH (20 mL). The fractions were collected and concentrated to give N-(3-(2-((4-(((1-acetylazetidin-3-yl)amino)-2-methoxyphenyl)amino)-7-oxopyrido[2,3-d]pyrimidin-8(7H)-yl)phenyl)acrylamide (14) (135 mg, 0.257 mmol, 60.7% yield) as a yellow crystalline solid. m/z (ESI, +ve ion) 526.0 (M+H)⁺. 1H NMR (400 MHz, DMSO-d6) δ ppm 10.42 (1H, br.), 8.74 (1H, s), 8.15 (1H, s), 7.91 (2H, d, J=9.4 Hz), 7.61 (1H, br.), 7.51 (1H, t, J=8.0 Hz), 7.18 (1H, br.), 7.02 (1H, d, J=8.0 Hz), 6.36-6.56 (2H, m), 6.23-6.36 (1H, m), 6.15 (2H, 5.71-5.87 (1H, m), 4.44 (1H, m), 4.18 (1H, 4.10 (1H, 3.75 (1H, m), 3.73 (3H, s), 3.58 (1H, m), 3.03 (1H, m), 1.80 (3H, s).

Example 15

N-(3-(2-((2-chloro-4-(4-methyl-1-piperazinyl)phenyl)amino)-7-oxopyrido[2,3-d]pyrimidin-8(7H)-yl)phenyl)-2-propenamide The title compound was prepared according to the procedures described for Example 1, starting from 2-chloro-4-(4-methylpiperazin-1-yl)aniline (Aurum Pharmatech LLC, Wowell, N.J.). tert-Butyl (3-(2-((2-chloro-4-(4-methylpiperazin-1-yl)phenyl)amino)-7-oxopyrido[2,3-d]pyrimidin-8 (7H)-yl)phenyl)carbamate (15a): m/z (ESI, +ve ion) 562.0 (M+H)⁺.

8-(3-Aminophenyl)-2-((2-chloro-4-(4-methylpiperazin-1-yl)phenyl)amino)pyrido[2,3-d]pyrimidin-7(8H)-one (15b): m/z (ESI, +ve ion) 461.9 (M+H)⁺.

N-(3-(2-((2-Chloro-4-(4-methylpiperazin-1-yl)phenyl)amino)-7-oxopyrido[2,3-d]pyrimidin-8(7H)-yl)phenyl)acrylamide (15): m/z (ESI, +ve ion) 515.9 (M+H)⁺. ¹H NMR (400 MHz, DMSO-d₆) δ ppm 10.35 (1H, s), 10.03 (1H, br. s.), 8.83 (1H, s), 7.94 (1H, d, J=9.4 Hz), 7.83 (1H, d, J=8.4 Hz), 7.69 (1H, s), 7.53 (1H, t, J=8.0 Hz), 7.41 (1H, br. s.), 7.28 (1H, d, J=7.2 Hz), 7.02 (1H, d, J=7.8 Hz), 6.78 (1H, br. s.), 6.50 (1H, d, J=9.4 Hz), 6.44 (1H, dd, J=17.0, 10.2 Hz), 6.25 (1H, dd, J=17.0, 2.0 Hz), 5.76 (1H, dd, J=10.2, 2.0 Hz), 2.83 (4H, br. s.), 2.44 (4H, br. s.), 2.23 (3H, s).

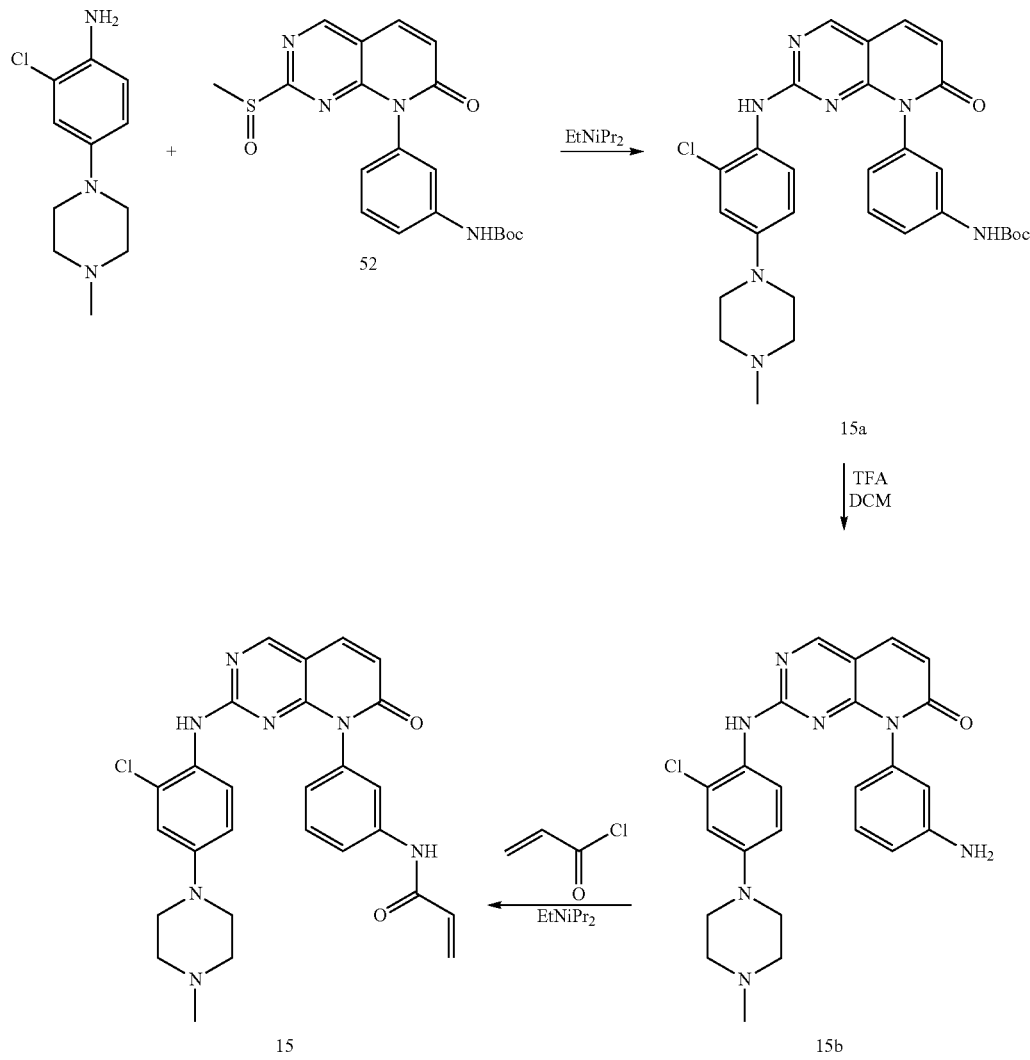

Example 16

N-(3-(2-((4-(((1-(2-fluoroethyl)-3-azetidinyl)amino)-2-methoxyphenyl)amino)-5-methyl-7-oxopyrido[2,3-d]pyrimidin-8(7H)-yl)phenyl)-2-propenamide

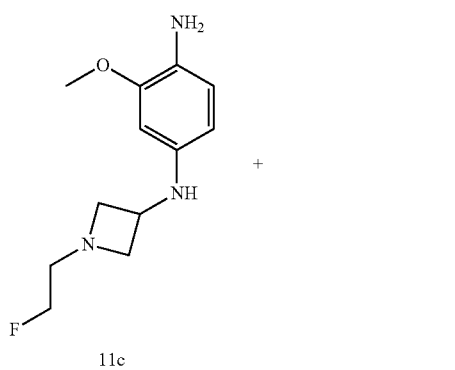

To a suspension of N1-(1-(2-fluoroethyl)azetidin-3-yl)-3-methoxybenzene-1,4-diamine (11c; 373 mg, 1.56 mmol) and N-(3-(5-methyl-2-(methylsulfinyl)-7-oxopyrido[2,3-d]pyrimidin-8(7H)-yl)phenyl)acrylamide (5b; 440 mg, 1.194 mmol) in tert-butanol (10 mL) was added DIEA (0.62 mL, 3.58 mmol). The mixture was heated in an oil bath at 80° C. for 1 h. The reaction mixture was concentrated to dryness under reduced pressure (rotary evaporator) and the crude residue was purified on silica gel on an ISCO Combiflash RF (40 g Redisep column, using a gradient of 5-10% 2M NH$_3$/ MeOH in DCM) affording enriched product. It was then repurified on a Gilson preparatory HPLC (Gemini Phenomenex; 30×150 mm, 5μ, 10-95% 0.1% TFA/CH$_3$CN in 0.1% TFA/water). The desired fractions were collected, and concentrated to dryness in a genevac overnight. The resulting solid was dissolved in 9:1=DCM:MeOH and was then passed through a Silicycle SPE-R66030B-20× SiliaSep OT, 5 g/25 mL carbonate column using 10% MeOH/DCM then concentrated and dried under vacuum affording N-(3-(2-((4-((1-(2-fluoroethyl)azetidin-3-yl)amino)-2-methoxyphenyl)amino)-5-methyl-7-oxopyrido[2,3-d]pyrimidin-8(7H)-yl)phenyl) acrylamide (317 mg, 0.58 mmol, 49% yield) as a yellow solid. m/z (ESI, +ve ion) 544.0 (M+H)$^+$. $^1$H NMR (400 MHz, DMSO-d$_6$) δ ppm 10.37 (1H, s), 8.78 (1H, br. s.), 8.05 (1H, br. s.), 7.84 (1H, d, J=7.0 Hz), 7.60 (1H, s), 7.50 (1H, t, J=8.0 Hz), 7.15 (1H, d, J=9.0 Hz), 6.99 (1H, d, J=9.0 Hz), 6.41-6.51 (1H, m), 6.23-6.34 (2H, m), 6.16 (1H, d, J=2.2 Hz), 5.85 (1H, br. s.), 5.73-5.81 (1H, m), 5.57 (1H, br. s.), 4.49 (1H, t, J=4.8 Hz), 4.37 (1H, t, 1=4.8 Hz), 3.90 (1H, br. s.), 3.73 (5H, br. s.), 2.76-2.88 (2H, m), 2.74 (1H, t, J=4.9 Hz), 2.63-2.71 (1H, m), 2.46 (3H, s).

Example 17

N-(3-(5-methyl-2-((4-(4-methylpiperazin-1-yl)phenyl)amino)-7-oxopyrido[2,3-d]pyrimidin-8(7H)-yl)phenyl)acrylamide

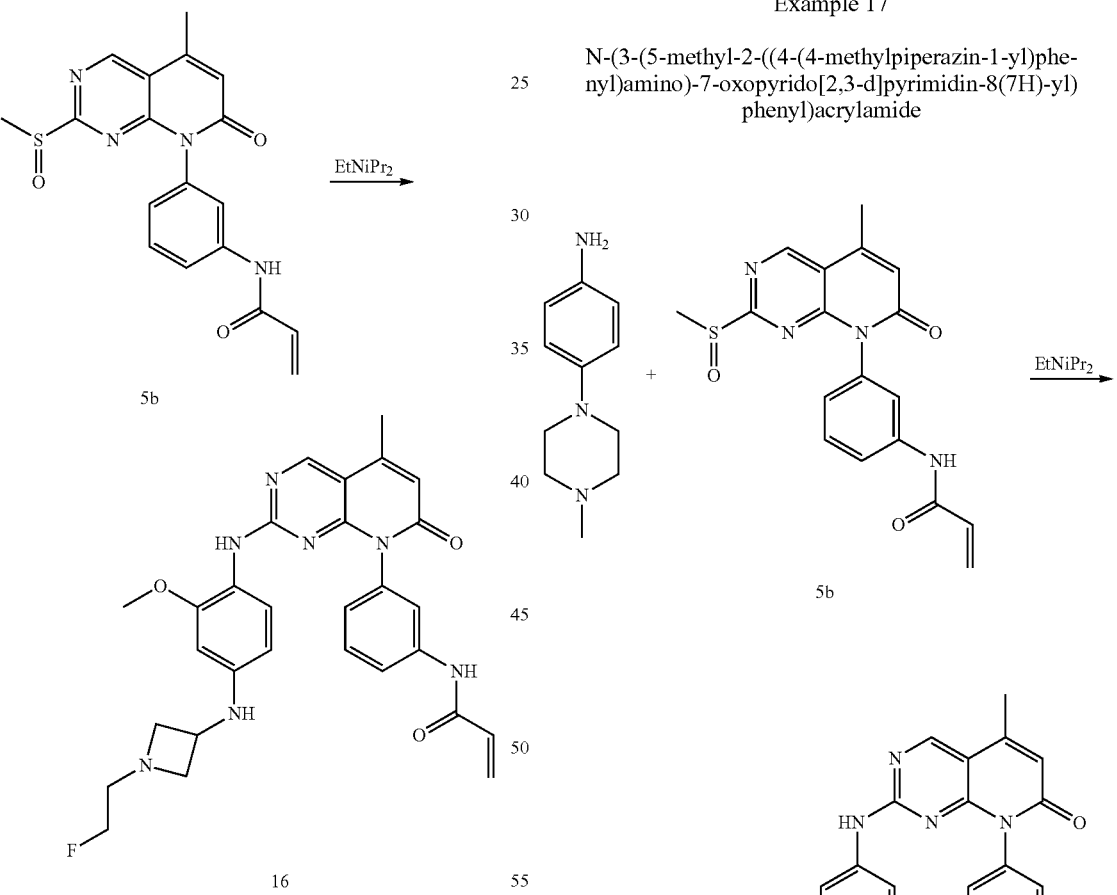

A microwave tube was charged with N-(3-(5-methyl-2-(methylsulfinyl)-7-oxopyrido[2,3-d]pyrimidin-8(7H)-yl)phenyl)acrylamide (5b; 210 mg, 0.57 mmol), 4-(4-methylpiperazino)aniline (136 mg, 0.71 mmol) and DIEA (0.20 mL, 1.14 mmol) in tert-butanol (5.5 mL). The tube was sealed and the mixture was heated to 100° C. for 3 d. The mixture was concentrated and then the brown solid was suspended in Et$_2$O and collected by filtration. The brown solid was washed with Et$_2$O to afford 270 mg of crude material. The crude material was absorbed onto a plug of silica gel and purified by chromatography through a Redi-Sep pre-packed silica gel column (12 g), eluting with a gradient of 0-20% MeOH in DCM. This enriched product was repurified on a Gilson preparatory HPLC (Gemini Phenomenex; 30×150 mm, 5μ, 10-95% 0.1% TFA/CH$_3$CN in 0.1% TFA/water). The product containing fractions were combined and concentrated. A saturated solution of aqueous NaHCO$_3$ was added and the mixture was extracted with 3:1 CHCl$_3$/IPA (3×30 mL). The combined organic layers were dried over anhydrous Na$_2$SO$_4$, filtered and concentrated to provide N-(3-(5-methyl-2-((4-(4-methylpiperazin-1-yl)phenyl)amino)-7-oxopyrido[2,3-d]pyrimidin-8(7H)-yl)phenyl)acrylamide (52 mg, 0.11 mmol, 18% yield) as a yellow solid. m/z (ESI, +ve ion) 496.1 (M+H)$^+$. NMR (400 MHz, DMSO-d$_6$) δ ppm 10.35 (1H, s), 8.82 (1H, s), 7.93 (1H, d, J=8.61 Hz), 7.57-7.56 (1H, m), 7.53 (1H, t, J=8.12 Hz), 7.17-7.19 (2H, m), 6.95-7.02 (1H, m), 6.53-6.56 (1H, m), 6.37-6.48 (1H, m), 6.31 (1H, d, J=0.39 Hz), 6.21-6.28 (1H, m), 5.72-5.80 (1H, m), 2.91-3.02 (4H, m), 2.46 (3H, s), 2.39-2.44 (4H, m) 2.21 (3H, s).

Example 18

N-(3-(2-((2-methoxy-4-(piperazin-1-yl)phenyl)amino)-5-methyl-7-oxopyrido[2,3-d]pyrimidin-8(7H)-yl)phenyl)acrylamide

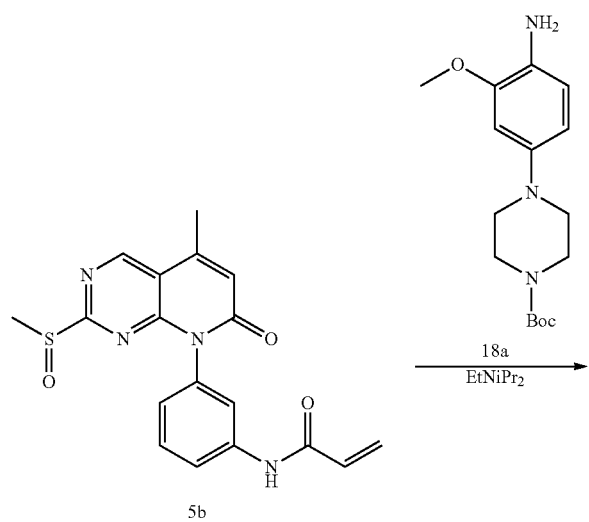

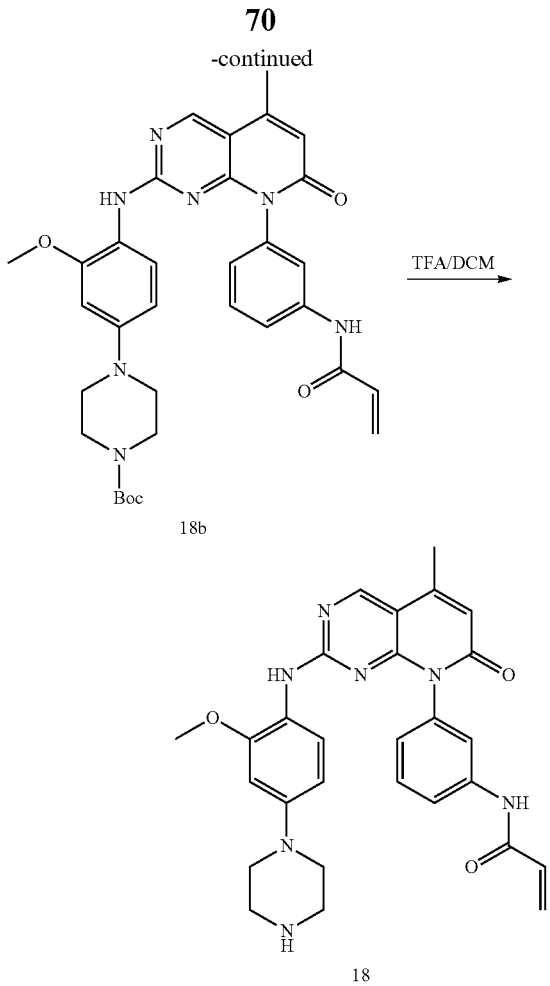

Preparation of tert-butyl 4-(4-amino-3-methoxyphenyl)piperazine-1-carboxylate (18a): A solution of 1-tert-butyl 1-piperazinecarboxylate (Sigma Aldrich, 3.37 g, 18.12 mmol), 5-fluoro-2-nitroanisole (Oakwood Products, West Columbia, S.C., 3.10 g, 18.12 mmol) and N-ethyl-N-isopropylpropan-2-amine (6.31 mL, 36.2 mmol) in DMSO (11 mL) in a 20 mL glass microwave tube was sealed and heated in a heating block at 95° C. overnight (20 h). Upon cooling, the reaction mixture crystallized to a yellow solid. It was diluted with 150 mL of EtOAc, washed sequentially with 20 mL of water, 20 mL of NaHCO$_3$ and brine (20 mL). The organic solution was dried over MgSO$_4$ and concentrated affording tert-butyl 4-(3-methoxy-4-nitrophenyl)piperazine-1-carboxylate (6.14 g, 18.20 mmol, 99% yield) as a yellow crystalline solid. m/z (ESI, +ve ion) 359.9 (M+Na)$^+$. $^1$H NMR (400 MHz, MeOH-d4) δ ppm 7.96 (1H, d, J=9.2 Hz), 6.59 (1H, dd, J=9.4, 2.5 Hz), 6.55 (1H, d, J=2.3 Hz), 3.97 (3H, s), 3.56-3.65 (4H, 3.45-3.52 (4H, m), 1.51 (9H, s). Pd/C (10 wt. %, dry basis, wet activated, 284 mm, 0.267 mmol) and tert-butyl 4-(3-methoxy-4-nitrophenyl)piperazine-1-carboxylate (600 mg, 1.78 mmol) were treated with EtOH (30 mL) and allowed to stir under an atmosphere of hydrogen (balloon) for 23 h. The reaction mixture was filtered through an acrodisc (0.20 um), the resulting purple solution was then concentrated on the rotovap and then under vacuum overnight affording tert-butyl 4-(4-amino-3-methoxyphenyl)piperazine-1-carboxylate (539 mg, 1.76 mmol, 99% yield) as a purple film. m/z (ESI, +ve ion) 307.0/309.0 (M+H)$^+$. $^1$H NMR (400 MHz, MeOH) δ ppm 6.71 (1H, d, J=8.4 Hz), 6.62 (1H, d, J=2.3 Hz), 6.46 (1H, dd, J=8.3, 2.4 Hz), 3.85 (3H, s), 3.51-3.61 (4H, m), 2.92-3.02 (4H, m), 1.47-1.52 (9H, s).

Preparation of N-(3-(2-((2-methoxy-4-(piperazin-1-yl)phenyl)amino)-5-methyl-7-oxopyrido[2,3-d]pyrimidin-8(7H)-yl)phenyl)acrylamide (18). To a suspension of tert-butyl 4-(4-amino-3-methoxyphenyl)piperazine-1-carboxylate (18a, 539 mg, 1.753 mmol) and N-(3-(5-methyl-2-(methylsulfinyl)-7-oxopyrido[2,3-d]pyrimidin-8(7H)-yl)phenyl)acrylamide (5b, 432 mg, 1.173 mmol) in tert-butanol (15 mL) at RT was added DIEA (0.61 mL, 3.52 mmol) followed by dioxane (6 mL). The reaction mixture was heated in a heating block at 90° C. for 20 h. LC-MS analysis indicated roughly 13% conversion to the desired product along with unreacted starting materials. The reaction mixture was concentrated on the rotovap and the crude residue was suspended in Et$_2$O and filtered. The greenish brown amorphous solid was washed with Et$_2$O (3×20 mL) and this removed most of the aniline starting material (18a). The crude material contained roughly 19% of the desired product (18b) along with recovered 5b. m/z (ESI, +ve ion) 611.9 (M+H)$^+$. The crude residue was used in the subsequent step without further purification.

Crude tert-butyl 4-(4-((8-(3-acrylamidophenyl)-5-methyl-7-oxo-7,8-dihydropyrido[2,3-d]pyrimidin-2-yl)amino)-3-methoxyphenyl)piperazine-1-carboxylate (18b) from the previous step was treated with DCM (5 mL) and TFA (5.0 mL, 64.9 mmol) and allowed to stir at RT for 30 min. The reaction mixture was concentrated and purified on the on an ISCO Combiflash RF (24 g Redisep Gold column, using a gradient of 5-20% 2 M NH$_3$/MeOH in DCM) affording enriched product. It was repurifed on a Gilson (Gemini Phenomenex; 30×150 mm, 5 u, 10-95% 0.1% TFA/CH$_3$CN in 0.1% TFA/water), concentrated in the genevac overnight and then passed through a Silicycle SPE-R66030B-20× SiliaSep OT, 5 g/25 mL carbonate column using 20% MeOH/DCM to remove any residual salt then dried under vacuum affording N-(3-(2-((2-methoxy-4-(piperazin-1-yl)phenyl)amino)-5-methyl-7-oxopyrido[2,3-d]pyrimidin-8(7H)-yl)phenyl)acrylamide (18) (20.6 mg, 0.040 mmol) as a bright yellow amorphous solid. m/z (ESI, +ve ion) 512.0 (M+H)$^+$. $^1$H NMR (400 MHz, DMSO-d$_6$) δ ppm 10.33 (1H, s), 8.80 (1H, s), 8.08 (1H, s), 7.87 (1H, d, J=8.2 Hz), 7.57 (1H, s), 7.50 (1H, t, J=8.0 Hz), 7.27 (1H, d, J=8.8 Hz), 6.97 (1H, d, J=8.6 Hz), 6.50 (1H, d, J=2.3 Hz), 6.38-6.48 (1H, m), 6.20-6.35 (2H, m), 5.99 (1H, br. s.), 5.76 (1H, dd, J=10.1, 1.9 Hz), 3.77 (3H, s), 2.87-2.99 (4H, m), 2.74-2.85 (4H, m), 2.46 (3H, s).

Example 19

N-(3-(2-((2-methoxy-4-(1-methylpiperidin-4-yl)phenyl)amino)-5-methyl-7-oxopyrido[2,3-d]pyrimidin-8(7H)-yl)phenyl)acrylamide

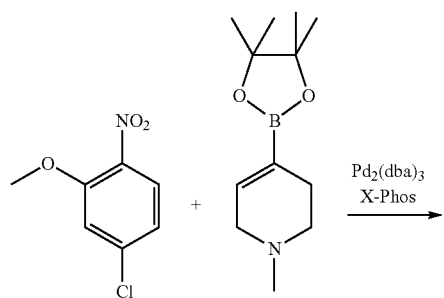

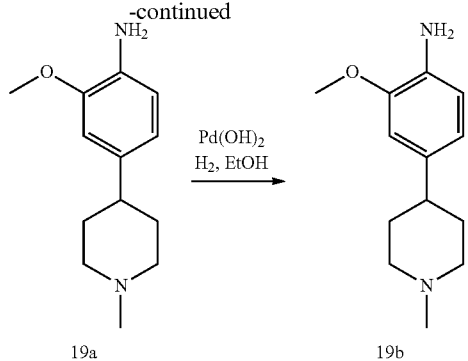

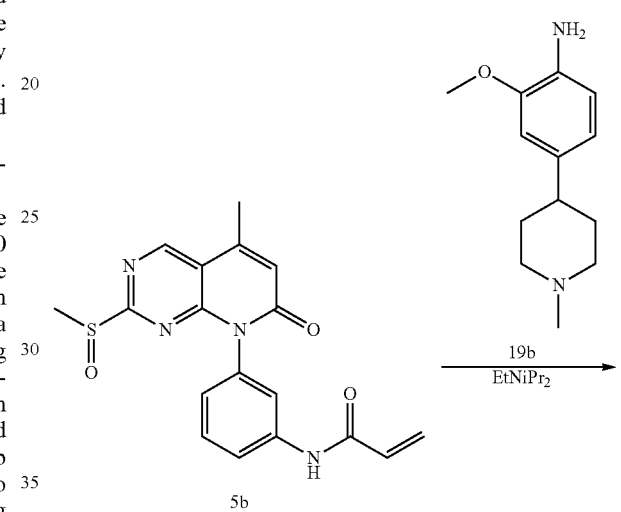

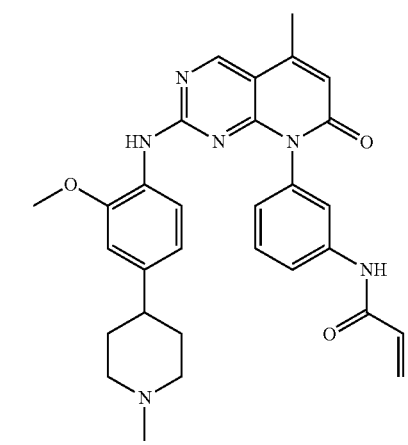

Preparation of 2-methoxy-4-(1-methylpiperidin-4-yl)aniline (19b): A 25 mL glass microwave tube was charged with potassium phosphate tribasic (3.00 g, 13.05 mmol), 2-(dicyclohexylphosphino)-2',4',6'-tri-isopropyl-1,1'-biphenyl (Strem Chemicals, Newburyport, Mass., 83 mg, 0.174 mmol), tris(dibenzylideneacetone)dipalladium (0) (Strem Chemicals, Newburyport, Mass., 80 mg, 0.087 mmol), 1-methyl-1,2,3,6-tetrahydropyridine-4-boronic acid pinacol ester (Acros Organics, New Jersey, 971 mg, 4.35 mmol) followed by 5-chloro-2-nitroanisole (Sigma Aldrich, 816 mg, 4.35 mmol). The solids were purged with argon and treated with 1,4-dioxane (12 mL) and water (4 mL), sealed and heated at 110° C. in a heating block for 1 h. The reaction mixture was treated with 1 N NaOH and extracted with EtOAc (3×30 mL), dried over MgSO$_4$, filtered and concentrated. The crude residue was purified on the ISCO Combiflash RF (80 g Thomson SingleStep column, using a gradient of 0-20% MeOH in DCM) affording 4-(3-methoxy-4-nitrophenyl)-1-methyl-1,2,3,6-tetrahydropyridine (19a; 970 mg, 3.91 mmol, 90% yield) as a rust-brown solid which crystallized upon standing. m/z (ESI, +ve ion) 249.1 (M+H)$^+$. $^1$H NMR (400 MHz, CDCl$_3$) δ ppm 7.86 (1H, d, J=8.4 Hz), 6.99-7.08 (2H, m), 6.17-6.24 (1H, m), 3.97 (3H, s), 3.15 (2H, q, J=2.8 Hz), 2.65-2.74 (2H, m), 2.53-2.62 (2H, m), 2.38-2.46 (3H, m). In a 50 mL glass reactor, 4-(3-methoxy-4-nitrophenyl)-1-methyl-1,2,3,6-tetrahydropyridine (940 mg, 3.79 mmol) was treated with palladium hydroxide (20 wt % Pd, dry basis, on wet carbon, degussa type e101 ne/w, 266 mg, 0.38 mmol) and anhydrous EtOH (20 mL). The reactor was purged with hydrogen (5×) and allowed to stir under 50 psi hydrogen at RT for 4 h. The reaction mixture was filtered through a 0.45 urn acrodisc to remove the catalyst residues washing with MeOH and concentrated to dryness under high vacuum affording 2-methoxy-4-(1-methylpiperidin-4-yl)aniline (19b; 830 mg, 3.77 mmol, 99% yield) as a yellow crystalline solid. m/z (ESI, +ve ion) 221.0 (M+H)$^+$. $^1$H NMR (400 MHz, CDCl$_3$) δ ppm 6.56-6.74 (3H, m), 3.76-3.89 (3H, m), 3.54-3.76 (2H, m), 2.97 (2H, d, J=11.2 Hz), 2.34-2.47 (1H, m), 2.23-2.34 (3H, m), 1.95-2.12 (2H, m), 1.70-1.90 (4H, m).

Preparation of N-(3-(2-((2-methoxy-4-(1-methylpiperidin-4-yl)phenyl)amino)-5-methyl-7-oxopyrido[2,3-d]pyrimidin-8(7H)-yl)phenyl)acrylamide (19): To a suspension of 2-methoxy-4-(1-methylpiperidin-4-yl)aniline (19b, 363 mg, 1.65 mmol) and N-(3-(5-methyl-2-(methylsulfinyl)-7-oxopyrido[2,3-d]pyrimidin-8(7H)-yl)phenyl)acrylamide (5b, 300 mg, 0.81 mmol) in tert-butanol (15 mL) at RT was added diisopropylethylamine (0.43 mL, 2.443 mmol). The mixture was heated at 100° C. for 48 h. The reaction mixture was concentrated on the rotovap and the crude residue was suspended in Et$_2$O and filtered. The resulting light yellow amorphous solid was washed with Et$_2$O (3×50 mL) and chromatographed on an ISCO Combiflash RF (40 g Thomson SingleStep column, using a gradient of 0-15% MeOH in DCM) affording enriched product. It was repurifed on a Gilson (Gemini Phenomenex; 30×150 mm, 5 u, 10-95% 0.1% TFA/CH$_3$CN in 0.1% TFA/water), concentrated in the genevac overnight and then passed through a Silicycle SPE-R66030B-20× SiliaSep OT, 5 g/25 mL carbonate column using 20% MeOH/DCM to remove any residual salt then dried under vacuum affording N-(3-(2-((2-methoxy-4-(1-methylpiperidin-4-yl)phenyl)amino)-5-methyl-7-oxopyrido[2,3-d]pyrimidin-8(7H)-yl)phenyl)acrylamide (22 mg) as a light yellow solid. m/z (ESI, +ve ion) 525.0 (M+H)$^+$. $^1$H NMR (400 MHz, DMSO$_6$) δ ppm 10.34 (1H, s), 8.85 (1H, s), 8.16 (1H, s), 7.85 (1H, d, J=9.2 Hz), 7.63 (1H, s), 7.48-7.56 (1H, m), 7.36 (1H, d, J=8.4 Hz), 7.00 (1H, d, J=7.8 Hz), 6.80 (1H, d, J=1.4 Hz), 6.38-6.47 (1H, In), 6.30-6.38 (2H, m), 6.19-6.29 (1H, m), 5.70-5.78 (1H, m), 3.80 (3H, s), 2.84 (2H, d, J=11.2 Hz), 2.47 (3H, s), 2.25-2.36 (1H, m), 2.19 (3H, s), 1.92 (2H, td, J=11.1, 3.7 Hz), 1.52-1.69 (4H, m).

Example 20

N-(3-(2-((4-(4-acetylpiperazin-1-yl)-2-methoxyphenyl)amino)-5-methyl-7-oxopyrido[2,3-d]pyrimidin-8(7H)-yl)phenyl)acrylamide

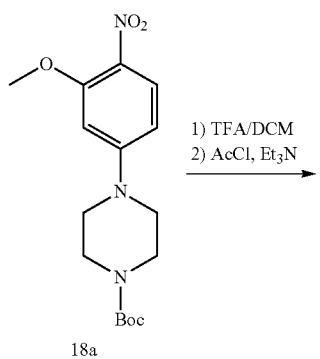

18a

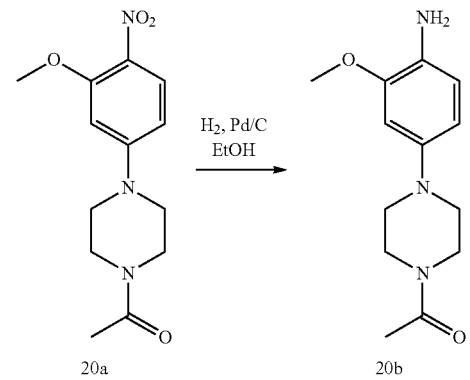

20a    20b

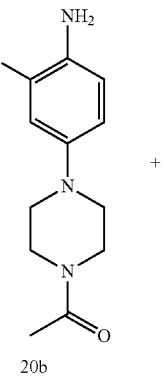

20b

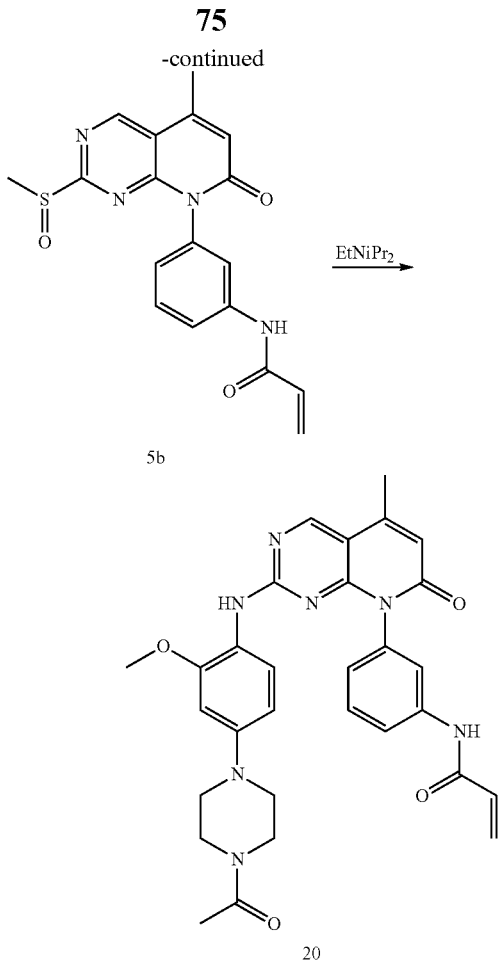

Preparation of 1-(4-(3-methoxy-4-nitrophenyl)piperazin-1-yl)ethanone (20a). To a solution of tert-butyl 4-(3-methoxy-4-nitrophenyl)piperazine-1-carboxylate (18a; 1.66 g, 4.92 mmol) in 5 mL of DCM at RT was added TFA (3.65 mL, 49.2 mmol) and the resulting mixture was stirred at RT for 2 h. It was concentrated under reduced pressure. The yellow residue was partitioned between 200 mL of EtOAc and 25 mL of 1 N NaOH. The layers were separated and the organic solution was washed with 25 mL of brine, dried over sodium sulfate and concentrated to give 1-(3-methoxy-4-nitrophenyl)piperazine, m/z (ESI, +ve ion) 238.1 (M+H)$^+$. The yellow residue was dissolved in 100 mL of DCM, cooled with and ice bath, treated with triethylamine (1.37 mL, 9.84 mmol) followed by acetyl chloride (0.38 mL, 5.41 mmol). After 1 h at 0° C., it was treated with 25 mL of 0.5 N NaOH. The layers were separated and the aqueous was extracted with 50 mL of DCM. The combined DCM solution was washed with 25 mL of brine, dried over Na$_2$SO$_4$ and concentrated to give 1-(4-(3-methoxy-4-nitrophenyl)piperazin-1-yl)ethanone (20a) as a yellow crystalline solid. Crude material was used in the next step. $^1$H NMR (400 MHz, DMSO-d$_6$) δ ppm 7.91 (1H, d, J=9.4 Hz), 6.59 (1H, dd, J=9.4, 2.3 Hz), 6.54 (1H, d12.3 Hz), 3.92 (3H, s), 3.59 (4H, d, J=2.7 Hz), 3.51-3.56 (2H, m), 3.43-3.50 (2H, m), 2.05 (3H, s).

Preparation of 1-(4-(4-amino-3-methoxyphenyl)piperazin-1-yl)ethanone (20b). A solution of 1-(4-(3-methoxy-4-nitrophenyl)piperazin-1-yl)ethanone (20a) in 10 mL of EtOH was hydrogenated with a balloon filled with hydrogen in the presence of palladium (10 wt. % on activated carbon, 0.61 g, 0.57 mmol) for 18 h at RT. It was filtered through a pad of Celite and rinsed with EtOAc (2×20 mL). The filtrate was concentrated. The brown residue was triturated with 10 mL of hexanes. The liquid was decanted. The solid was dried in a vacuum oven at 40° C. for 1 h to give 1-(4-(4-amino-3-methoxyphenyl)piperazin-1-yl)ethanone (20b; 1.42 g, 5.70 mmol, 99% yield) as a brown solid. Crude material used in the next step. $^1$H NMR (400 MHz, DMSO-d$_6$) δ ppm 6.54 (2H, m), 6.32 (1H, dd, J=8.3, 2.4 Hz), 4.63 (2H, br.), 3.76 (3H, s), 3.54 (4H, m), 2.95 (2H, m), 2.89 (2H, m), 2.02 (3H, s). m/z (ESI, +ve ion) 250.1 (M+H)$^+$.

Preparation of N-(3-(2-((4-(4-acetylpiperazin-1-yl)-2-methoxyphenyl)amino)-5-methyl-7-oxopyrido[2,3-d]pyrimidin-8(7H)-yl)phenyl)acrylamide (20). A suspension of 1-(4-(4-amino-3-methoxyphenyl)piperazin-1-yl)ethanone (20b; 351 mg, 1.40 mmol), diisopropylethylamine (0.41 mL, 2.34 mmol) and N-(3-(5-methyl-2-(methylsulfinyl)-7-oxopyrido[2,3-d]pyrimidin-8(7H)-yl)phenyl)acrylamide (5b; 288 mg, 0.78 mmol) in tert-butanol (2 mL) and dioxane (1 mL) in a sealed glass tube was heated in an oil bath at 110° C. for 72 h. It was concentrated under reduced pressure. The brown residue was stirred in 5 mL of ether for 10 min. The liquid was decanted; the remaining solid was loaded on a silica gel column and eluted with 2-10% MeOH in DCM followed by 5% 2 M NH$_3$ in MeOH in DCM to give the title compound (20) (150 mg, 34% yield) as a yellow crystalline solid. $^1$H NMR (400 MHz, DMSO-d$_6$) δ ppm 10.33 (1H, s), 8.81 (1H, s), 8.12 (1H, s), 7.88 (1H, d, J=8.0 Hz), 7.42-7.61 (2H, m), 7.28 (1H, d, J=9.0 Hz), 6.98 (1H, d, J=7.8 Hz), 6.56 (1H, m), 6.44 (1H, m), 6.33 (1H, s), 6.24 (1H, m), 6.04 (1H, br. s.), 5.75 (1H, m), 3.78 (3H, s), 3.56 (4H, m), 3.04 (2H, m), 2.97 (2H, m), 2.46 (3H, s), 2.03 (3H, s). m/z (ESI, +ve ion) 554.3 (M+H)$^+$.

Although the pharmacological properties of the compounds of Formula I vary with structural change, in general, activity possessed by compounds of Formula I may be demonstrated in vivo. The pharmacological properties of the compounds of this invention may be confirmed by a number of pharmacological in vitro assays. The exemplified pharmacological assays which follow have been carried out with the compounds according to the invention and their salts.

It has been surprisingly found that provided compounds selectively inhibit each of the EGFR activating and deletion mutations. Moreover, provided compounds are sparing for WT EGFR and associated dose-limiting toxicities. This stands in contrast to other known EGFR inhibitors (e.g., BIBW2992 and HKI-272) which are only somewhat effective against mutants but retain activity against WT EGFR and are therefore limited by toxicities associated with inhibition of WT EGFR.

BIOLOGICAL EVALUATION

Detection of pEGFR on NSCLC Cell Lines.

The effects of compounds on the phosphorylation of wild-type, T790M mutant, and Exon19 deletion (A746-750) EGFR were monitored using Mesoscalc™ multiplex assays (MSD), in which levels of phosphorylated EGFR protein were determined using total PRAS40 levels as a control. H1975 (T790M/L858R), HCC827 (Δ746-750) and A549 (wild-type EGFR) NSCLC cells were plated on 6-well tissue culture plates, serum starved for overnight and treated with 9 concentrations of compound starting at 2 µM (5-fold dilutions) for 60 min. Wild-type A549 cells were challenged with 100 ng/ml EGF for 15 min before collection. Cells were lysed according to manufacturer's instructions and lysates processed for analysis in the mg) multiplex plate reader.

Inhibition of Proliferation of NSCLC Cell Lines.

NSCLC cell lines H1975 (T790M/L858R), HCC827 (Δ746-750) and A549 (wild-type) were seeded in 96-well tissue culture plates (Corning, Lowell, Mass.) at 5,000 cells/well (H1975) and 4,000 cells/well (HCC827 and A549) in 95 µL of cell growth media overnight. Compounds starting at 10 mM concentration and diluted 8 times (4-fold dilutions) in DMSO were diluted 50 fold in RPM1 then 5 µL was added to cells. After 72 h, viable cell signal was quantified using Cell Titer Glow (Promega, Madison, Wis.) and a SpectraMax M5 plate reader (Molecular Devices, Sunnyvale, Calif.) per manufacturer's instructions. Final DMSO concentration in test and control wells was 0.1%. No DSMO effect was noted on cell growth.

Tumor Growth Inhibition of NSCLC Cell Lines.

Athymic nude mice (Harlan Labs, Indianapolis, Ind.) or SHO mice (Charles River, Wilmington, Mass.) were injected with 5 million H1975 cells in the right flank. Mice bearing established (~200 mm$^3$) xenografts were randomly assigned into four groups (10 mice/group) and treated orally (PO), daily (QD), with compound formulated in 15% HPbCD, 2% HPMC, 1% Pluronic F68, pH 4.5 w/HCl for the duration of the experiment. Tumor volumes and body weights were measured twice per week using calipers and an analytical scale, respectively. An Inhibitory Emax model was used to calculate the $ED_{50}$ based on tumor volumes at the end of the experiment using WinNonlin Version 5.1.1, Pharsight, (Mountain View, Calif.). Repeated measures ANOVA (RMANOVA) was used to calculate significant tumor growth inhibition versus the vehicle treated group.

| Example # | H1975 pEGFR IC50 (nM) | HCC827 pEGFR IC50 (nM) | A549 pEGFR IC50 (nM) | H1975 cell killing IC50 (nM) | HCC827 cell killing IC50 (nM) |
|---|---|---|---|---|---|
| 1 | 3.2 | 3.4 | 76 | 8 | 4 |
| 2 | NT | NT | NT | undefined | NT |
| 3 | NT | NT | NT | 326 | 126 |
| 4 | NT | NT | NT | 0.7 | 1 |
| 5 | 2.8 | 8 | 323 | 4 | 10 |
| 6 | 4.3 | NT | 8.2 | 12 | 1:7 |
| 7 | NT | NT | NT | undefined | 2.81 |
| 8 | NT | NT | NT | 92 | 21 |
| 9 | NT | NT | NT | 361 | 53 |
| 10 | 2 | NT | 84 | 4 | 4 |
| 11 | 6 | 5 | 155 | 9.6 | 3 |
| 12 | NT | NT | NT | 680 | 18 |
| 13 | NT | NT | NT | 128 | 76 |
| 14 | NT | NT | NT | 190 | 24 |
| 15 | NT | NT | NT | 11 | 3.5 |
| 16 | NT | NT | NT | 22 | 18 |
| 17 | NT | NT | NT | 3.6 | 7.3 |
| 18 | | | | | |
| 19 | | | | | |
| 20 | | | | | |

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but were not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which were commonly used include lactose and corn starch. Lubricating agents, such as magnesium stearate, were also typically added. For oral administration in a capsule form, useful diluents include lactose and dried corn starch. When aqueous suspensions and/or emulsions were administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques were known in the art.

The pharmaceutical compositions of this invention may be administered by nasal aerosol or inhalation. Such compositions were prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:
1. A compound of Formula I

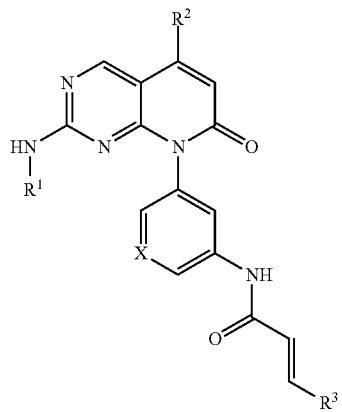

wherein $R^1$ is

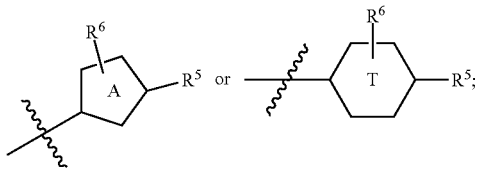

wherein Ring A is 5 membered heteroaryl;
wherein Ring T is phenyl or 6 membered heteroaryl;
wherein $R^2$ is H, F, Cl or methyl;
wherein $R^3$ is H, $C_1$-$C_6$ alkyl or $C_1$-$C_6$ dialkylamino-$C_1$-$C_6$ alkyl;
wherein $R^5$ is unsubstituted or substituted 5-6 membered saturated heterocyclyl or substituted 4-7 membered heterocyclylamino;
wherein $R^6$ is H, $C_1$-$C_6$ alkoxy, $C_1$-$C_6$ haloalkoxy or halo; and
wherein X is CH or N;
provided $R^5$ is not 4-morpholinyl;
and pharmaceutically acceptable salts thereof.

2. Compound of claim 1 wherein X is CH; and pharmaceutically acceptable salts thereof.

3. Compound of claim 1 wherein $R^3$ is H; and pharmaceutically acceptable salts thereof.

4. Compound of claim 1 wherein $R^2$ is H or methyl; and pharmaceutically acceptable salts thereof.

5. Compound of claim 1 wherein $R^2$ is methyl; and pharmaceutically acceptable salts thereof.

6. Compound of claim 1 wherein $R^1$ is substituted phenyl; and pharmaceutically acceptable salts thereof.

7. Compound of claim 1 wherein $R^1$ is substituted pyridyl or substituted pyrimidinyl; and pharmaceutically acceptable salts thereof.

8. Compound of claim 1 wherein $R^5$ is optionally substituted piperazinyl, optionally substituted piperidinyl, optionally substituted pyrrolidinyl, optionally substituted diazepanyl, or optionally substituted azetidinylamino; wherein the piperazinyl, piperidinyl, pyrrolidinyl, diazepanyl, and azetidinyl rings are optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_{1-4}$ alkylcarbonyl, $C_{1-4}$ alkylsulfonyl, aminosulfonyl, $C_{1-4}$ hydroxyalkylcarbonyl, $C_{1-4}$ alkylaminocarbonyl, and $C_{1-4}$ haloalkylcarbonyl and pharmaceutically acceptable salts thereof.

9. Compound of claim 1, and pharmaceutically acceptable salts thereof, wherein $R^1$ is

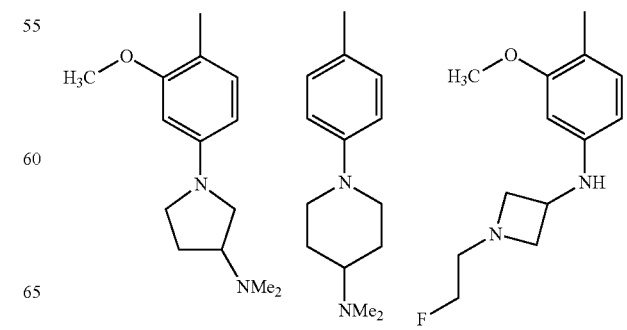

-continued
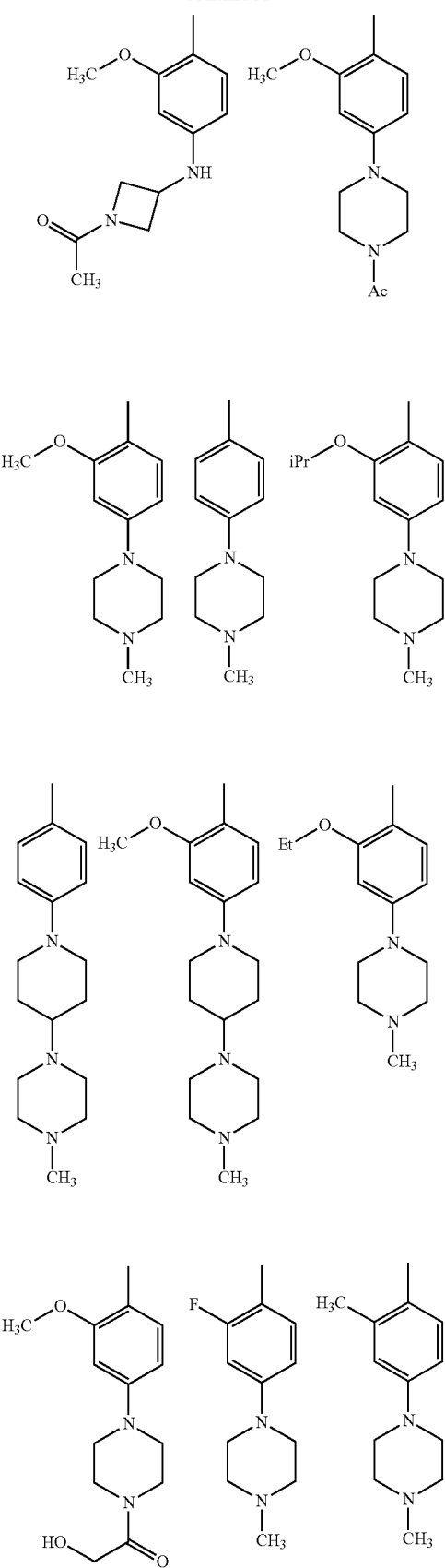
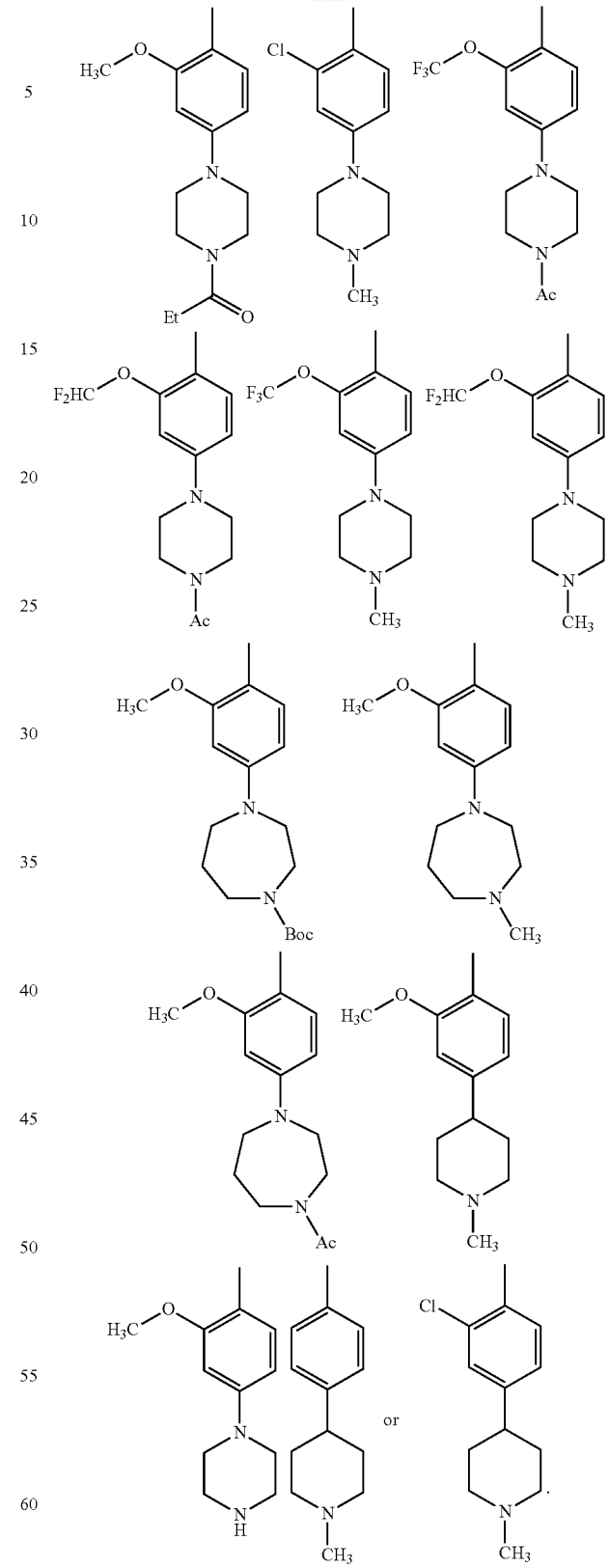
10. Compound of claim 1, and pharmaceutically acceptable salts thereof, wherein R⁵ is 1-fluoroethylazetidin-3-ylamino.

11. Compound of claim 1, and pharmaceutically acceptable salts thereof, wherein $R^6$ is H, methoxy or chloro.

12. Compound of claim 1, and pharmaceutically acceptable salts thereof, selected from
- N-(3-(2-((2-methoxy-4-(4-methyl-1-piperazinyl)phenyl)amino)-7-oxopyrido[2,3-d]pyrimidin-8(7H)-yl)phenyl)-2-prop enamide;
- (2E)-N-(3-(2-((2-methoxy-4-(4-methyl-1-piperazinyl)phenyl)amino)-7-oxopyrido[2,3-d]pyrimidin-8(7H)-yl)phenyl)-2-butenamide;
- N-(3-(2-((4-(4-methyl-1-piperazinyl)phenyl)amino)-7-oxopyrido[2,3-d]pyrimidin-8(7H)-yl)phenyl)-2-propenamide;
- N-(3-(2-((2-methoxy-4-(4-methyl-1-piperazinyl)phenyl)amino)-5-methyl-7-oxopyrido[2,3-d]pyrimidin-8(7H)-yl)phenyl)-2-propenamide;
- N-(3-(6-ethyl-2-((2-methoxy-4-(4-methyl-1-piperazinyl)phenyl)amino)-7-oxopyrido[2,3-d]pyrimidin-8(7H)-yl)phenyl)-2-prop enamide;
- N-(3-(2-((4-methoxy-6-(4-methyl-1-piperazinyl)-3-pyridinyl)amino)-7-oxopyrido[2,3-d]pyrimidin-8(7H)-yl)phenyl)-2-prop enamide;
- (2E)-4-(dimethylamino)-N-(3-(2-((2-methoxy-4-(4-methyl-1-piperazinyl)phenyl)amino)-7-oxopyrido[2,3-d]pyrimidin-8(7H)-yl)phenyl)-2-butenamide;
- N-(4-fluoro-3-(2-((2-methoxy-4-(4-methyl-1-piperazinyl)phenyl)amino)-7-oxopyrido[2,3-d]pyrimidin-8(7H)-yl)phenyl)-2-propenamide;
- N-(3-(2-((4-((1-(2-fluoroethyl)-3-azetidinyl)amino)-2-methoxyphenyl)amino)-7-oxopyrido[2,3-d]pyrimidin-8(7H)-yl)phenyl)-2-propenamide;
- 2-chloro-N-(3-(2-((2-methoxy-4-(4-methyl-1-piperazinyl)phenyl)amino)-7-oxopyrido[2,3-d]pyrimidin-8(7H)-yl)phenyl)acetamide;
- 3-(dimethylamino)-N-(3-(2-((2-methoxy-4-(4-methylpiperazin-1-yl)phenyl)amino)-7-oxopyrido[2,3-d]pyrimidin-8(7H)-yl)phenyl)propanamide;
- N-(3-(2-((4-((1-acetylazetidin-3-yl)amino)-2-methoxyphenyl)amino)-7-oxopyrido[2,3-d]pyrimidin-8(7H)-yl)phenyl)acrylamide;
- N-(3-(2-((2-chloro-4-(4-methyl-1-piperazinyl)phenyl)amino)-7-oxopyrido[2,3-d]pyrimidin-8(7H)-yl)phenyl)-2-propenamide;
- N-(3-(2-((4-((1-(2-fluoroethyl)-3-azetidinyl)amino)-2-methoxyphenyl)amino)-5-methyl-7-oxopyrido[2,3-d]pyrimidin-8(7H)-yl)phenyl)-2-propenamide;
- N-(3-(5-methyl-2-((4-(4-methylpiperazin-1-yl)phenyl)amino)-7-oxopyrido[2,3-d]pyrimidin-8(7H)-yl)phenyl)acrylamide;
- N-(3-(2-((2-methoxy-4-(piperazin-1-yl)phenyl)amino)-5-methyl-7-oxopyrido[2,3-d]pyrimidin-8(7H)-yl)phenyl)acrylamide
- N-(3-(2-((2-methoxy-4-(1-methylpiperidin-4-yl)phenyl)amino)-5-methyl-7-oxopyrido[2,3-d]pyrimidin-8(7H)-yl)phenyl)acrylamide; and
- N-(3-(2-((4-(4-acetylpiperazin-1-yl)-2-methoxyphenyl)amino)-5-methyl-7-oxopyrido[2,3-d]pyrimidin-8(7H)-yl)phenyl)acrylamide.

13. A compound of Formula II

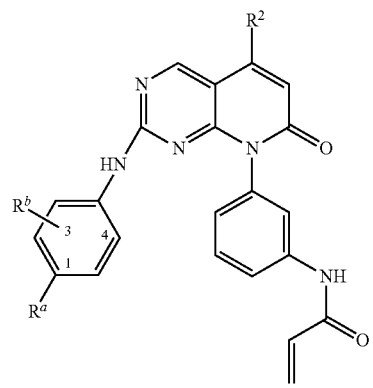

wherein $R^2$ is H or methyl;
wherein $R^a$ is optionally substituted piperazinyl, optionally substituted piperidinyl, optionally substituted pyrrolidinyl, optionally substituted diazepanyl, optionally or optionally substituted azetidinylamino; and
wherein $R^b$ is H or methoxy;
and pharmaceutically acceptable salts thereof.

14. Compound of claim 13 wherein $R^2$ is methyl; and pharmaceutically acceptable salts thereof.

15. Compound of claim 13 wherein $R^b$ is located at position 3 on the phenyl ring; and pharmaceutically acceptable salts thereof.

16. Compound of claim 13 wherein $R^a$ is optionally substituted piperazinyl, optionally substituted piperidinyl, optionally substituted pyrrolidinyl, or optionally substituted diazepanyl; wherein the piperazinyl, piperidinyl, pyrrolidinyl and diazepanyl rings are optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_{1-4}$ alkylcarbonyl, $C_{1-4}$ alkylsulfonyl, aminosulfonyl, $C_{1-4}$ hydroxyalkylcarbonyl, $C_{1-4}$ alkylaminocarbonyl, and $C_{1-4}$ haloalkylcarbonyl; and pharmaceutically acceptable salts thereof.

17. Compound of claim 13 wherein $R^a$ is azetidinylamino; wherein the azetindinyl is optionally substituted with one or more substituents selected from $C_{1-3}$ alkyl, $C_{1-3}$ haloalkyl, $C_{1-4}$ alkoxycarbonyl, $C_{1-3}$ alkylamino, optionally substituted 5-6 membered heterocyclyl, $C_{1-4}$ alkylcarbonyl, $C_{1-4}$ alkylsulfonyl, aminosulfonyl, $C_{1-4}$ hydroxyalkylcarbonyl, $C_{1-4}$ alkylaminocarbonyl, and $C_{1-4}$ haloalkylcarbonyl; and pharmaceutically acceptable salts thereof.

18. A pharmaceutical composition comprising a pharmaceutically-acceptable carrier and a compound of any of claims 1-17.

19. A method of treating breast, lung, head, neck or bladder cancer in a subject, said method comprising administering an effective amount of a compound of any of claims 1-17.

20. A method of treating EGFR/ErbB2 related disorders in a mammal, said method comprising administering an effective amount of a compound of any of claims 1-17.

21. A method of treating EGFR mutant related disease in a subject, said method comprising administering an effective amount of a compound of any of claims 1-17.

* * * * *